United States Patent
Yang et al.

(10) Patent No.: US 11,512,039 B2
(45) Date of Patent: Nov. 29, 2022

(54) AROMATIC AMINE DERIVATIVES, PREPARATION METHODS THEREFOR, AND USES THEREOF

(71) Applicant: GUANGZHOU CHINARAY OPTOELECTRONIC MATERIALS LTD., Guangdong (CN)

(72) Inventors: Xi Yang, Guangdong (CN); Junyou Pan, Guangdong (CN)

(73) Assignee: GUANGZHOU CHINARAY OPTOELECTRONIC MATERIALS LTD., Guangdong (CN)

(*) Notice: Subject to any disclaimer, the term of this patent is extended or adjusted under 35 U.S.C. 154(b) by 541 days.

(21) Appl. No.: 16/463,653

(22) PCT Filed: Nov. 23, 2017

(86) PCT No.: PCT/CN2017/112703
§ 371 (c)(1),
(2) Date: May 23, 2019

(87) PCT Pub. No.: WO2018/095382
PCT Pub. Date: May 31, 2018

(65) Prior Publication Data
US 2019/0315675 A1    Oct. 17, 2019

(30) Foreign Application Priority Data

Nov. 23, 2016 (CN) .......................... 201611048273.9

(51) Int. Cl.
*C07C 211/61*  (2006.01)
*C07D 401/12*  (2006.01)
(Continued)

(52) U.S. Cl.
CPC .......... *C07C 211/61* (2013.01); *C07D 401/12* (2013.01); *C07D 403/12* (2013.01);
(Continued)

(58) Field of Classification Search
None
See application file for complete search history.

(56) References Cited

U.S. PATENT DOCUMENTS 3,567,450 A    3/1971   Brantly et al.
3,615,404 A    10/1971  Price et al.
(Continued)

FOREIGN PATENT DOCUMENTS

CN         1583691      2/2005
CN       101747889      6/2010
(Continued)

OTHER PUBLICATIONS

Endo, A. et al., "Thermally Activated Delayed Fluorescence from Sn4p-Porphyrin Complexes and Their Application to Organic Light-Emitting Diodes—A Novel Mechanism for Electroluminescence," Adv. Mater., 21, 2009, 4802-4806.
(Continued)

*Primary Examiner* — Clinton A Brooks
(74) *Attorney, Agent, or Firm* — PV IP PC; Wei Te Chung; Ude Lu

(57) ABSTRACT

The present disclosure relates to an aromatic amine derivative represented by general formula (I).
(Continued)

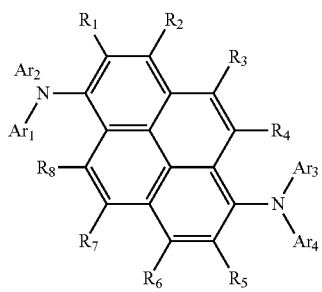

(I)

The aromatic amine derivative has fluorescence emission at a short light emission wavelength, and the light-emission spectrum of the aromatic amine derivative has a narrow half-peak width, and accordingly, the material has deep-blue fluorescence emission and has a very-high light emission efficiency. An organic electroluminescent component prepared by using the aromatic amine derivative has deep-blue color coordinates, a high light emission efficiency and a long life-span.

5 Claims, 1 Drawing Sheet

(51) Int. Cl.
  *C07D 403/12* (2006.01)
  *C07D 407/12* (2006.01)
  *C07D 409/14* (2006.01)
  *C07D 413/10* (2006.01)
  *H01L 51/00* (2006.01)
  *H01L 51/50* (2006.01)

(52) U.S. Cl.
  CPC ......... *C07D 407/12* (2013.01); *C07D 409/14* (2013.01); *C07D 413/10* (2013.01); *H01L 51/006* (2013.01); *H01L 51/0054* (2013.01); *H01L 51/0061* (2013.01); *H01L 51/0067* (2013.01); *H01L 51/0072* (2013.01); *H01L 51/0073* (2013.01); *H01L 51/0074* (2013.01); *H01L 51/50* (2013.01)

(56) References Cited

U.S. PATENT DOCUMENTS

| | | | |
|---|---|---|---|
| 4,720,432 | A | 1/1988 | Vanslyke et al. |
| 4,769,292 | A | 9/1988 | Tang et al. |
| 5,061,569 | A | 10/1991 | Vanslyke et al. |
| 5,121,029 | A | 6/1992 | Hosokawa et al. |
| 5,130,603 | A | 7/1992 | Tokailin et al. |
| 6,020,078 | A | 2/2000 | Chen et al. |
| 6,251,531 | B1 | 6/2001 | Enokida et al. |
| 7,233,019 | B2 | 6/2007 | Ionkin et al. |
| 7,250,532 | B2 | 7/2007 | Iwakuma et al. |
| 2006/0210830 | A1 | 9/2006 | Funahashi et al. |
| 2006/0222886 | A1 | 10/2006 | Kwong et al. |
| 2007/0092753 | A1 | 4/2007 | Begley et al. |
| 2007/0152565 | A1 | 7/2007 | Kubota et al. |
| 2007/0252517 | A1 | 11/2007 | Owczarczyk et al. |
| 2008/0048254 | A1 | 2/2008 | Saka |
| 2008/0113101 | A1 | 5/2008 | Inoue et al. |
| 2008/0297037 | A1 | 12/2008 | Vestweber et al. |
| 2009/0134784 | A1 | 5/2009 | Lin et al. |
| 2010/0141124 | A1 | 6/2010 | Lee et al. |
| 2012/0138914 | A1 | 6/2012 | Kawamura et al. |
| 2012/0217869 | A1 | 8/2012 | Adachi et al. |
| 2013/0153867 | A1 | 6/2013 | Seo et al. |
| 2013/0234118 | A1 | 9/2013 | Kwon et al. |
| 2014/0138669 | A1 | 5/2014 | Nakagawa et al. |
| 2014/0138670 | A1 | 5/2014 | Nakagawa et al. |
| 2015/0034915 | A1 | 2/2015 | Kim et al. |
| 2015/0041784 | A1 | 2/2015 | Shizu et al. |
| 2015/0141642 | A1 | 5/2015 | Adachi et al. |
| 2015/0287928 | A1 | 10/2015 | Kubota et al. |
| 2016/0104847 | A1 | 4/2016 | Xia et al. |
| 2016/0225992 | A1 | 8/2016 | Ito et al. |

FOREIGN PATENT DOCUMENTS

| | | |
|---|---|---|
| CN | 1914293 | 12/2010 |
| CN | 103165818 | 6/2013 |
| CN | 103304428 | 9/2013 |
| CN | 103483332 | 1/2014 |
| CN | 102448945 | 1/2016 |
| CN | 105359292 | 2/2016 |
| CN | 105514288 | 4/2016 |
| CN | 105810837 | 7/2016 |
| DE | 102005058557 | 6/2007 |
| JP | 2913116 | 6/1999 |
| JP | 2008053397 | 3/2008 |
| KR | 20060006760 | 1/2006 |
| TW | 201309696 | 3/2013 |
| TW | 201309778 | 3/2013 |
| TW | 201343874 | 11/2013 |
| TW | 201350558 | 12/2013 |
| WO | 0121729 | 3/2001 |
| WO | 2004013073 | 2/2004 |
| WO | 2004016575 | 2/2004 |
| WO | 2004018587 | 3/2004 |
| WO | 2006000388 | 1/2006 |
| WO | 2006000389 | 1/2006 |
| WO | 2006058737 | 6/2006 |
| WO | 2006122630 | 11/2006 |
| WO | 2007065549 | 6/2007 |
| WO | 2007065678 | 6/2007 |
| WO | 2007115610 | 10/2007 |
| WO | 2007140847 | 12/2007 |
| WO | 2008006449 | 1/2008 |
| WO | 2008136522 | 11/2008 |
| WO | 2009102026 | 8/2009 |
| WO | 2009102054 | 8/2009 |
| WO | 2010135519 | 11/2010 |
| WO | 2011110277 | 9/2011 |
| WO | 2013133359 | 9/2013 |
| WO | 2013154064 | 10/2013 |
| WO | 2015009076 | 1/2015 |

OTHER PUBLICATIONS

Endo, A. et al., "Efficient up-conversion of triplet excitons into a singlet state and its application for organic light emitting diodes," Appl. Phys. Lett., 98, 2011, pp. 083302-1-83302-3.
Lee, SY et al., "High-efficiency organic light-emitting diodes utilizing thermally activated delayed fluorescence from triazine-based donor-acceptor hybrid molecules," Appl. Phys. Lett., 101, 2012, pp. 093306-1-093306-4.
Tanaka, H. et al., "Efficient green thermally activated delayed fluorescence (TADF) from a phenoxazine-triphenyltriazine (PXZ-TRZ) derivative," Chem. Commun., 48, 2012, pp. 11392-11394.
Goushi, K. et al., "Organic light-emitting diodes employing efficient reverse intersystem crossing for triplet-to-singlet state conversion," Nature Photonics, 6, 2012, pp. 253-258.
Joyama, H. et al., "Highly efficient organic light-emitting diodes from delayed fluorescence," Nature, 492, 2012, pp. 234-238.
Zhang, Q. et al., "Design of Efficient Thermally Activated Delayed Fluorescence Materials for Pure Blue Organic Light Emitting Diodes," J. Am. Chem. Soc, 134, 2012, pp. 14706-14709.
Mehes, G. et al., "Enhanced Electroluminescence Efficiency in a Spiro-Acridine Derivative through Thermally Activated Delayed Fluorescence," Angew. Chem. Int. Ed., 51, 2012, pp. 11311-11315.
Nakagawa, T. et al., "Electroluminescence based on thermally activated delayed fluorescence generated by a spirobifluorene donor-acceptor structure," Chem. Commun., 48, 2012, pp. 9580-9582.

(56) References Cited

OTHER PUBLICATIONS

Nasu, K. et al., "A highly luminescent spiro-anthracenone-based organic light-emitting diode exhibiting thermally activated delayed fluorescence," Chem. Commun., 49, 2013, 3 pages.

Li, J. et al., "Highly Efficient Organic Light-Emitting Diode Based on a Hidden Thermally Activated Delayed Fluorescence Channel in a Heptazine Derivative," Adv. Mater., 25, 2013, 5 pages.

Dias, F. B. et al., "Triplet Harvesting with 100% Efficiency by Way of Thermally Activated Delayed Fluorescence in Charge Transfer OLED Emitters," Adv. Mater., 25, 2013, pp. 3707-3714.

Komino, T. et al., "Suppression of Efficiency Roll-Off Characteristics in Thermally Activated Delayed Fluorescence Based Organic Light-Emitting Diodes Using Randomly Oriented Host Molecules," Chem. Mater., 25, 2013, pp. 3038-3047.

Tanaka, H. et al., "Twisted Intramolecular Charge Transfer State for Long-Wavelength Thermally Activated Delayed Fluorescence," Chem. Mater., 25, 2013, pp. 3766-3771.

Lee, J. et al., "Oxadiazole- and triazole-based highly-efficient thermally activated delayed fluorescence emitters for organic light-emitting diodes," J. Mater. Chem. C, 1, 2013, 6 pages.

Ishimatsu, R. et al., "Solvent Effect on Thermally Activated Delayed Fluorescence by 1,2,3,5-Tetrakis(carbazol-9-yl)-4,6-dicyanobenzene," J. Phys. Chem. A, 117, 2013, pp. 5607-5612.

Kipphan, H., "Handbook of Print Media: Technologies and Production Methods," ISBN 3-540-67326-1, 2004, Chapter 1.3 pp. 40-67, Chapter 1.5 pp. 117-144, Chapters 5.5 pp. 711-730.

Bulovic, V. et al., "Transparent light-emitting devices," Nature, 380, 1996, p. 29.

Gu, G. et al., "Transparent organic light emitting devices," Appl. Phys. Lett., 68, 1996, pp. 2606-2608.

International Search Report issued for International Patent Application No. PCT/CN2017/112703, dated Jan. 30, 2018, 8 pages including English translation.

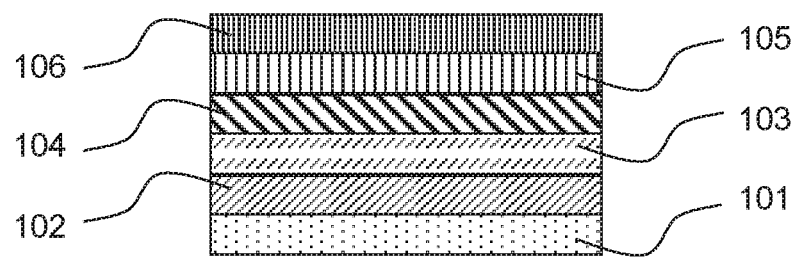

AROMATIC AMINE DERIVATIVES, PREPARATION METHODS THEREFOR, AND USES THEREOF

CROSS-REFERENCE TO RELATED APPLICATIONS

The present application is a national stage for International Application PCT/CN2017/112703, filed on Nov. 23, 2017, which claims priority benefit of Chinese Patent Application No. 201611048273.9, entitled "Aromatic amine derivatives and application thereof in organic electronic devices" and filed on Nov. 23, 2016, the entire content of both applications are incorporated herein for all purposes.

TECHNICAL FIELD

The present disclosure relates to the field of organic electroluminescence technology, and in particular to an aromatic amine derivative, mixture, formulation, and application thereof in the field of organic electroluminescence.

BACKGROUND

Organic light-emitting diodes (OLEDs) show great potential in the application of optoelectronic devices such as flat-panel display and lighting due to the diversity in synthesis, relatively low manufacturing costs, and excellent opto-electronic performance of organic semiconducting materials.

Organic electroluminescence refers to the phenomenon of converting electrical energy into light energy using organic semiconductors. An organic electroluminescent element utilizing the organic electroluminescence generally has a structure containing a positive electrode, a negative electrode and organic layers between them. In order to improve the efficiency and lifetime of the organic electroluminescent element, the organic layer has multilayer structure, and each layer contains different organic substance. Specifically, a hole injection layer, a hole transport layer, a light emitting layer, an electron transport layer, an electron injection layer, and the like can be included. In such electroluminescent element, if a voltage is applied between the two electrodes, holes are injected into the organic layer through the positive electrode, electrons are injected into the organic layer through the negative electrode. When the injected holes meet the electrons in light emitting layer, excitons are formed. The formed excitons emit light when they transition back to the ground state. This organic electroluminescent element has the property of self-luminescence, high luminance, high efficiency, low driving voltage, wide viewing angle, high contrast, high responsiveness and the like.

In order to improve the luminous efficiency of the organic electroluminescent element, various light-emitting materials based on fluorescence and phosphorescence have been developed. The development of excellent blue-light emitting material, whether fluorescent materials or phosphorescent materials, is, however, still a great challenge. In general, currently the organic light-emitting diodes using blue fluorescent materials are more reliable. However, most of the current blue fluorescent materials have too broad emission spectra and poor color purity, which is not conducive to high-end display. In addition, the synthesis of such fluorescent materials is also complicated winch is not conducive to mass production, and at the same time, the stability of the OLED of such blue fluorescent materials needs to be further improved. Therefore, the development of blue fluorescent material with narrow-band emission spectrum and good stability, on the one hand, is advantageous for obtaining a longer-life and higher-efficiency blue-emitting device, and on the other hand, is advantageous for the improvement of the color gamut, so as to improve the display effect.

The light emitting layer of the blue organic electroluminescent element of the prior art uses host-guest doping structure. The conventional blue-light emitting host material is usually anthracene-based fused ring derivative, as described in the patents CN1914293B, CN102448945B, US2015287928A1, etc. However, these compounds have problems of insufficient luminous efficiency and brightness, and poor lifetime of the device. As a blue-light emitting guest compound of the prior art, the aryl vinylamine compound can be used (WO 04/013073, WO 04/016575, WO 04/018587). However, these compounds have poor thermal stability and are easily decomposed, resulting in poor lifetime of the device, which is currently the most important shortcoming in the industry. Furthermore, these compounds have poor color purity and it is difficult to achieve deep blue luminescence. In addition, patents such as U.S. Pat. No. 7,233,019, KR 2006-0006760, and the like disclose organic electroluminescent devices using pyrene compound of amino substituents, but due to the low color purity of blue light, it is difficult to realize deep blue luminescence, and thus there is a problem with the full color display that reflects the natural colors.

Therefore, there is still a need for further improvements in materials, particularly in light emitting compounds, especially in blue luminescent compounds. To allow that the blue light-emitting materials have deep blue luminescence, and they are thermally stable, exhibit good efficiency and lifetime in the organic electroluminescent element, and they are easy to repeat in the manufacturing and operation of the device, and simple in material synthesis.

SUMMARY

An aromatic amine derivative as shown in general formula (I):

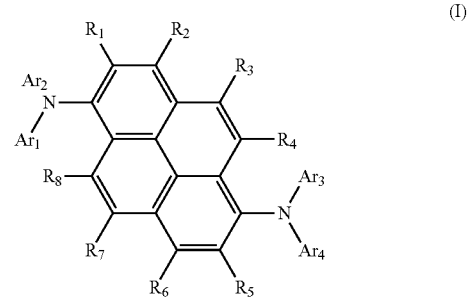

wherein, $R_1$, $R_2$, $R_3$, $R_4$, $R_5$, $R_6$, $R_7$ and $R_8$ are the same or different from each other, the $R_1$, $R_2$, $R_3$, $R_4$, $R_5$, $R_6$, $R_7$ and $R_8$ are each independently selected from the group consisting of: H, or a linear alkyl containing 1 to 20 C atoms, or an alkoxy containing 1 to 20 C atoms, or a thioalkoxy containing 1 to 20 C atoms, or a branched or cyclic alkyl containing 3 to 20 C atoms, or a substituted or unsubstituted silyl group, or a substituted keto group containing 1 to 20 C atoms, or an alkoxycarbonyl group containing 2 to 20 C atoms, or an aryloxycarbonyl group containing 7 to 20 C atom, a cyano group, a carbamoyl group, a haloformyl group, a formyl group, an isocyano group, isocyanate, thiocyanate or isothiocyanate, a hydroxyl group, a nitro group, $CF_3$, Cl, Br, F, a crosslinkable group, or a substituted or unsubstituted aromatic ring system containing 5 to 40 ring atoms or substituted or unsubstituted heteroaromatic ring system containing 5 to 40 ring atoms, or an aryloxy group containing 5 to 40 ring atoms or heteroaryloxy group containing 5 to 40 ring atoms;

one or more of the groups in the $R_3$, $R_2$, $R_3$, $R_4$, $R_5$, $R_6$, $R_7$ or $R_8$ may form monocyclic or polycyclic aliphatic or aromatic ring systems with each other and/or with a ring bonded to the group, one or more of the hydrogen atoms in the $R_4$, $R_2$, $R_3$, $R_4$, $R_5$, $R_6$, $R_7$ or $R_8$ are alternatively substituted by deuterium atoms.

$Ar_1$, $Ar_2$, $Ar_3$ and $Ar_4$ are the same or different from each other; at least one of the $Ar_1$, $Ar_2$, $Ar_3$ and $Ar_4$ are a group represented by the general formula (II), and the others are each independently selected from the group consisting of: a substituted or unsubstituted aromatic ring system containing 5 to 40 ring atoms or substituted or unsubstituted heteroaromatic ring system containing 5 to 40 ring atoms, or an aryloxy group containing from 5 to 40 ring atoms or heteroaryloxy group containing from 5 to 40 ring atoms;

wherein one or more of the groups in $Ar_1$, $Ar_2$, $Ar_3$ or $Ar_4$ may form polycyclic aliphatic or aromatic ring systems with each other and/or with a ring bonded to the group;

one or more of the hydrogen atoms in the $Ar_1$, $Ar_2$, $Ar_3$ or $Ar_4$ may be further alternatively substituted by deuterium atoms;

the structure of general formula (II) is:

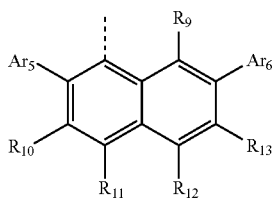

(II)

wherein $R_9$, $R_{10}$, $R_{11}$, $R_{12}$ and $R_{13}$ are the same or different from each other and the $R_9$, $R_{10}$, $R_{11}$, $R_{12}$ or $R_{13}$ are each independently selected from the group consisting of: H, or a linear alkyl containing 1 to 20 C atoms, or an alkoxy containing 1 to 20 C atoms, or a thioalkoxy containing 1 to 20 C atoms, or a branched or cyclic alkyl containing 3 to 20 C atoms, or a substituted or unsubstituted silyl group, or a substituted keto group containing 1 to 20 C atoms, or an alkoxycarbonyl group containing 2 to 20 C atoms, or an aryloxycarbonyl group containing 7 to 20 C atom, a cyano group, a carbamoyl group, a haloformyl group, a formyl group, an isocyano group, isocyanate, thiocyanate or isothiocyanate, a hydroxyl group, a nitro group, $CF_3$. Cl, Br, F, a crosslinkable group, or a substituted or unsubstituted aromatic ring system containing 5 to 40 ring atoms or substituted or unsubstituted heteroaromatic ring system containing 5 to 40 ring atoms, or an aryloxy group containing 5 to 40 ring atoms or heteroaryloxy group containing 5 to 40 ring atoms;

one or more of the groups in the $R_9$, $R_{10}$, $R_{11}$, $R_{12}$ or $R_{13}$ may form monocyclic or polycyclic aliphatic or aromatic ring systems with each other and/or with a ring bonded to the group;

$Ar_5$, $Ar_6$ are the same or different, and the $Ar_5$ or $Ar_6$ is each independently selected from the group consisting of: H, or a linear alkyl containing 1 to 20 C atoms, or an alkoxy containing 1 to 20 C atoms, or a thioalkoxy containing 1 to 20 C atoms, or a branched or cyclic alkyl containing 3 to 20 C atoms, or a substituted or unsubstituted silyl group, or a substituted keto group containing 1 to 20 C atoms, or an alkoxycarbonyl group containing 2 to 20 C atoms, or an aryloxycarbonyl group containing 7 to 20 C atom, a cyano group, a carbamoyl group, a haloformyl group, a formyl group, an isocyano group, isocyanate, thiocyanate or isothiocyanate, a hydroxyl group, a nitro group, $CF_3$, Cl, Br, F, a crosslinkable group, or a substituted or unsubstituted aromatic ring system containing 5 to 40 ring atoms or substituted or unsubstituted heteroaromatic ring system containing 5 to 40 ring atoms, or an aryloxy group containing 5 to 40 ring atoms or heteroaryloxy group containing 5 to 40 ring atoms;

one or more of the groups in $Ar_5$, $Ar_6$ may form polycyclic aliphatic or aromatic ring systems with each other and/or with a ring bonded to the group;

one or more of the hydrogen atoms in the $R_9$, $R_{10}$, $R_{11}$, $R_{12}$, $R_{13}$, $Ar_5$ or $Ar_6$ can be further alternatively substituted by deuterium atoms;

The dotted line indicates the single bond linked to the general formula (I).

A polymer comprises at least one repeating unit selected from the above aromatic amine derivative.

A formulation comprises the above aromatic amine derivative or the above polymer, and at least one organic solvent.

A mixture comprises the above aromatic amine derivative or the above polymer, and at least one organic functional material, the organic functional material may be selected from the group consisting of: hole (also called electron hole) injection or transport material (HIM/HTM), hole blocking material (HBM), electron injection or transport material (EIM/ETM), electron blocking material (EBM), organic matrix material (Host), singlet emitter (fluorescent emitter), triplet emitter (phosphorescent emitter), thermally activated delayed fluorescent material (TADF material) and organic dye.

Application of the aromatic amine derivative represented by the general formula (I) or the above polymer or the above formulation or the above mixture in organic electronic devices.

An organic electroluminescent device comprises a cathode, an anode and an organic layer, the organic layer is formed by the above aromatic amine derivative or the above polymer or the above formulation or the above mixture.

The above aromatic amine derivative has fluorescence emission at a short light emission wavelength, and the light-emission spectrum of the aromatic amine derivative has a narrow half-peak width, so that such substance has a deep blue fluorescence emission and has high luminous efficiency. The organic electroluminescent element prepared by such aromatic amine derivative has deep blue chromaticity coordinate, high luminous efficiency, and long device lifetime.

BRIEF DESCRIPTION OF THE DRAWINGS

FIG. 1 is a schematic diagram of an electronic device in an embodiment.

DETAILED DESCRIPTION OF THE INVENTION

In order to facilitate the understanding of the present disclosure, the present disclosure will be described more fully hereinafter with reference to the related accompanying drawings. Preferable embodiments are presented in the drawings. However, the present disclosure may be embodied in many different forms and is not limited to the embodiments described herein. Rather, these embodiments are provided so that the understanding of the disclosure of the present disclosure will be more thorough.

All technical and scientific terms used herein have the same meaning as commonly understood by skilled person in the art to which this disclosure belongs, unless otherwise defined. The terms used in the specification of the disclosure herein are for the purpose of describing specific embodiments only and are not intended to limit the present disclosure. The term "and/or" used herein includes any and all combinations of one or more of the associated listed items.

In the present disclosure, the host material and the matrix material have the same meaning and they are interchangeable.

In the present disclosure, the metal organic clathrate, the metal organic complexes, and organometallic complexes have the same meaning and are interchangeable.

In the present disclosure, formulation and printing ink, ink or inks, have the same meaning and can be used interchangeably.

In the present disclosure, "H" and hydrogen atom have the same meaning, and "D" and deuterium atom have the same meaning.

In the present disclosure, "alternatively substituted" has the same meaning as "may also be further substituted" and they are interchangeable, meaning that it may or may not be substituted, for example, one or more hydrogen atoms in $Ar_6$ are alternatively substituted by deuterium atoms means that one or more hydrogen atoms in $Ar_6$ may or may not be substituted by deuterium atoms.

An aromatic amine derivative is as shown in general formula (I).

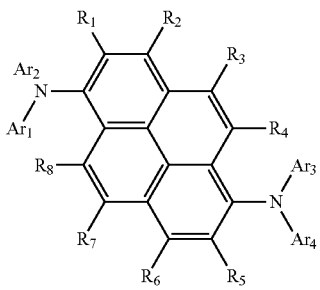

(I)

wherein $R_1$, $R_2$, $R_3$, $R_4$, $R_5$, $R_6$, $R_7$ and $R_8$ are the same or different from each other, the $R_1$, $R_2$, $R_3$, $R_4$, $R_5$, $R_6$, $R_7$ and $R_8$ are each independently selected from the group consisting of: H, or a linear alkyl containing 1 to 20 C atoms, or an alkoxy containing 1 to 20 C atoms, or a thioalkoxy containing 1 to 20 C atoms, or a branched or cyclic alkyl containing 3 to 20 C atoms, or a substituted or unsubstituted silyl group, or a substituted keto group containing 1 to 20 C atoms, or an alkoxycarbonyl group containing 2 to 20 C atoms, or an aryloxycarbonyl group containing 7 to 20 C atom, a cyano group (—CN), a carbamoyl group (—C(=O)NH$_2$), a haloformyl group (—C(=O)—X, wherein X represents halogen atom), a formyl group (—C(=O)—H), an isocyano group, isocyanate, thiocyanate or isothiocyanate, a hydroxyl group, a nitro group, $CF_3$, Cl, Br, F, a crosslinkable group, or a substituted or unsubstituted aromatic ring systems containing 5 to 40 ring atoms or substituted or unsubstituted heteroaromatic ring systems containing 5 to 40 ring atoms, or an aryloxy groups containing 5 to 40 ring atoms or heteroaryloxy groups containing 5 to 40 ring atoms;

one or more of the groups in the $R_1$, $R_2$, $R_3$, $R_4$, $R_5$, $R_6$, $R_7$ or $R_8$ may form monocyclic or polycyclic aliphatic or aromatic ring systems with each other and/or with a ring bonded to the group;

one or more of the hydrogen atoms in the $R_4$, $R_2$, $R_3$, $R_4$, $R_5$, $R_6$, $R_7$ or $R_8$ may be further alternatively substituted by deuterium atoms.

In one embodiment, $R_1$, $R_2$, $R_3$, $R_4$, $R_5$, $R_6$, $R_7$ and $R_8$ are the same or different from each other; the $R_1$, $R_2$, $R_3$, $R_4$, $R_5$, $R_6$, $R_7$ and $R_8$ are each independently selected from the group consisting of: H, or a linear alkyl containing 1 to 10 C atoms, or an alkoxy containing 1 to 10 C atoms, or a thioalkoxy containing 1 to 10 C atoms, or a branched or cyclic alkyl containing 3 to 10 C atoms, or a substituted or unsubstituted silyl group, or a substituted keto group containing 1 to 10 C atoms, or an alkoxycarbonyl group containing 2 to 10 C atoms, or an aryloxycarbonyl group containing 7 to 10 C atom, a cyano group (—CN), a carbamoyl group (—C(=O)NH$_2$), a haloformyl group (—C(=O)—X, wherein X represents halogen atom), a formyl group (—C(=O)—H), an isocyano group, isocyanate, thiocyanate or isothiocyanate, a hydroxyl group, a nitro group, $CF_3$, Cl, Br, F, a crosslinkable group, or a substituted or unsubstituted aromatic ring system containing 5 to 20 ring atoms or substituted or unsubstituted heteroaromatic ring system containing 5 to 20 ring atoms, or an aryloxy group containing 5 to 20 ring atoms or heteroaryloxy group containing 5 to 20 ring atoms; one or more of the groups in the $R_1$, $R_2$, $R_3$, $R_4$, $R_5$, $R_6$, $R_7$ or $R_8$ may form monocyclic or polycyclic aliphatic or aromatic ring systems with each other and/or with a ring bonded to the group. One or more of the hydrogen atoms in the $R_1$, $R_2$, $R_3$, $R_4$, $R_5$, $R_6$, $R_7$ or $R_8$ are alternatively substituted by deuterium atoms.

$Ar_1$, $Ar_2$, $Ar_3$ and $Ar_4$ are the same or different from each other; at least one of the $Ar_3$, $Ar_2$, $Ar_3$ and $Ar_4$ are a group represented by the general formula (II), and the others are each independently selected from the group consisting of: a substituted or unsubstituted aromatic ring system containing 5 to 40 ring atoms or substituted or unsubstituted heteroaromatic ring system containing to 40 ring atoms, or an aryloxy group containing 5 to 40 ring atoms or heteroaryl oxy group containing 5 to 40 ring atoms; wherein one or more of the groups may form polycyclic aliphatic or aromatic ring systems with each other and/or with a ring bonded to the group. One or more of the hydrogen atoms in the $Ar_3$, $Ar_2$, $Ar_3$ or $Ar_4$ may be further alternatively substituted by deuterium atoms.

In one embodiment, the $Ar_1$, $Ar_2$, $Ar_3$ and $Ar_4$ are the same or different from each other; at least one of the $Ar_1$, $Ar_2$, $Ar_3$ and $Ar_4$ are a group represented by the general formula (II), and the others are each independently selected from the group consisting of: a substituted or unsubstituted aromatic ring system containing 5 to 30 ring atoms or substituted or unsubstituted heteroaromatic ring system containing 5 to 30 ring atoms, or an aryloxy group containing 5 to 30 ring atoms or heteroaryl oxy group containing 5 to 30 ring atoms; wherein one or more of the groups may form polycyclic aliphatic or aromatic ring systems with each other and/or with a ring bonded to the group. One or more of the hydrogen atoms in the $Ar_f$, $Ar_2$, $Ar_3$ or $Ar_4$ may be further alternatively substituted by deuterium atoms.

In one embodiment, the $Ar_1$, $Ar_2$, $Ar_3$ and $Ar_4$ are the same or different from each other, at least one of the $Ar_1$, $Ar_2$, $Ar_3$ and $Ar_4$ are a group represented by the general formula (II), and the others are each independently selected from the group consisting of: a substituted or unsubstituted aromatic ring system containing 10 to 25 ring atoms or substituted or unsubstituted heteroaromatic ring system containing 10 to 25 ring atoms, or an aryloxy group containing 10 to 25 ring atoms or heteroaryl oxy group containing 10 to 25 ring atoms, wherein one or more of the groups may form monocyclic or polycyclic aliphatic or aromatic ring systems with each other and/or with a ring bonded to the group. One or more of the hydrogen atoms in the $Ar_1$, $Ar_2$, $Ar_3$ or $Ar_4$ may be further alternatively substituted by deuterium atoms.

In one embodiment, the original nucleus structure (ring system) of aromatic ring system in substituted or unsubstituted aryl group contains 5 to 15 carbon atoms; in one embodiment, the original nucleus structure (ring system) of aromatic ring system in substituted or unsubstituted aryl or heteroaryl group contains 5 to 10 carbon atoms.

The total number of carbon atoms and heteroatoms in the original nucleus structure of heteroaromatic ring systems in substituted or unsubstituted heteroaryl groups is at least 4. In one embodiment, the original nucleus structure (ring system) of heteroaromatic ring system in substituted or unsubstituted heteroaryl group contains 2 to 15 carbon atoms and at least one heteroatom; in one embodiment, the original nucleus structure (ring system) of heteroaromatic ring system in substituted or unsubstituted heteroaryl group contains 2 to 10 carbon atoms and at least one heteroatom. Wherein, the heteroatom may be Si, N, P, O, S, and/or Ge; in one embodiment, the heteroatom is selected from Si, N, P, O, and/or S; in one embodiment, the heteroatom is selected from N, O or S.

The aromatic ring system or aromatic group described above refers to hydrocarbyl comprising at least one aromatic ring, including monocyclic group and polycyclic ring system. The heteroaromatic ring system or heteroaromatic group described above refers to hydrocarbyl (containing heteroatoms) comprising at least one heteroaromatic ring, including monocyclic group and polycyclic ring system. Such polycyclic rings may have two or more rings, wherein two carbon atoms are shared by two adjacent rings, i.e., fused ring. At least one of such polycyclic rings is aromatic or heteroaromatic. In addition, the aromatic or heteroaromatic ring system includes not only aromatic or heteroaromatic systems, but also systems in which a plurality of aryl or heteroaryl groups may be interrupted by short non-aromatic units (<10% non-H atoms, further less than 5% non-H atoms, such as C, N or O atoms). Therefore, systems such as 9,9'-spirobifluorene, 9,9-diarylfluorene, triarylamine, diaryl ether and the like are also considered to be aromatic ring systems.

In one embodiment, the aromatic group is selected from the group consisting of: benzene, naphthalene, anthracene, phenanthrene, perylene, tetraeene, pyrene, benzopyrene, triphenylene, acenaphthene, fluorene, spirofluorene and derivatives thereof.

In one embodiment, the heteroaromatic group is selected from the group consisting of: furan, benzofuran, dibenzofuran, thiophene, benzothiophene, dibenzothiophene, pyrrole, pyrazole, triazole, imidazole, oxazole, oxadiazole, thiazole, tetrazole, indole, carbazole, pyrroloimidazole, pyrrolopyrrole, thienopyrrole, thienothiophene, furopyrrole, furofuran, thienofuran, benzi sox azole, benzisothiazole, benzimidazole, pyridine, pyrazine, pyridazine, pyrimidine, triazine, quinoline, isoquinoline, cinnoline, quinoxaline, phenanthridine, perimidine, quinazoline, quinazolinone, and derivatives thereof.

The structure of the general formula (II) is:

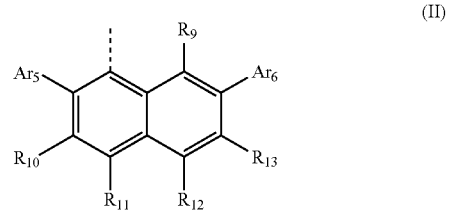

wherein
$R_9$, $R_{10}$, $R_{11}$, $R_{12}$ and $R_{13}$ are the same or different from each other, the $R_9$, $R_{10}$, $R_{11}$, $R_{12}$ and $R_{13}$ are each independently selected from the group consisting of: H, or a linear alkyl containing 1 to 20 C atoms, or an alkoxy containing 1 to 20 C atoms, or a thioalkoxy containing 1 to 20 C atoms, or a branched or cyclic alkyl containing 3 to 20 C atoms, or a substituted or unsubstituted silyl group, or a substituted keto group containing 1 to 20 C atoms, or an alkoxycarbonyl group containing 2 to 20 C atoms, or an aryloxycarbonyl group containing 7 to 20 C atom, a cyano group (—CN), a carbamoyl group (—C(=O)NH$_2$), a haloformyl group (—C(=O)—X, wherein X represents halogen atom), a formyl group (—C(=O)—H), an isocyano group, isocyanate, thiocyanate or isothiocyanate, a hydroxyl group, a nitro group, CF$_3$, Cl, Br, F, a crosslinkable group, or a substituted or unsubstituted aromatic ring system containing 5 to 40 ring atoms or substituted or unsubstituted heteroaromatic ring system containing 5 to 40 ring atoms, or an aryloxy group containing 5 to 40 ring atoms or heteroaryloxy group containing 5 to 40 ring atoms, wherein one or more of the groups may form monocyclic or polycyclic aliphatic or aromatic ring systems with each other and/or with the ring bonded to said groups. One or more of the hydrogen atoms in various groups described above may also be further substituted by D.

In one embodiment, $R_9$, $R_{10}$, $R_{11}$, $R_{12}$ and $R_{13}$ are the same or different from each other, the $R_9$, $R_{10}$, $R_{11}$, $R_{12}$ and $R_{13}$ are each independently selected from the group consisting of: H, or a linear alkyl containing 1 to 10 C atoms, or an alkoxy containing 1 to 10 C atoms, or a thioalkoxy containing 1 to 10 C atoms, or a branched or cyclic alkyl containing 3 to 10 C atoms, or a substituted or unsubstituted silyl group, or a substituted keto group containing 1 to 10 C atoms, or an alkoxycarbonyl group containing 2 to 10 C atoms, or an aryloxycarbonyl group containing 7 to 10 C atom, a cyano group (—CN), a carbamoyl group (—C(=O)NH$_2$), a haloformyl group (—C(=O)—X, wherein X represents halogen atom), a formyl group (—C(=O)—H), an isocyano group, isocyanate, thiocyanate or isothiocyanate, a hydroxyl group, a nitro group, CF$_3$, Cl, Br; F, a crosslinkable group, or a substituted or unsubstituted aromatic ring system containing 5 to 20 ring atoms or substituted or unsubstituted heteroaromatic ring system containing 5 to 20 ring atoms, or an aryloxy group containing 5 to 20 ring atoms or heteroaryloxy group containing 5 to 20 ring atoms, wherein one or more of the groups may form monocyclic or polycyclic aliphatic or aromatic ring systems with each other and/or with the ring bonded to the groups. One or more of the hydrogen atoms in various groups described above may be further substituted by D.

Ar$_5$ and Ar$_6$ are the same or different, and the Ar$_5$ or Ar$_6$ is each independently selected from the group consisting of: H, or a linear alkyl containing 1 to 20 C atoms, or a alkoxy containing 1 to 20 C atoms, or a thioalkoxy containing 1 to 20 C atoms, or a branched or cyclic alkyl containing 3 to 20 C atoms, or a substituted or unsubstituted silyl group, or a substituted keto group containing 1 to 20 C atoms, or an alkoxycarbonyl group containing 2 to 20 C atoms, or an aryloxycarbonyl group containing 7 to 20 C atom, a cyano group (—CN), a carbamoyl group (—C(=O)NH$_2$), a haloformyl group (—C(=O)—X, wherein X represents halogen atom), a formyl group (—C(=O)—H), a isocyano group, isocyanate, thiocyanate or isothiocyanate, a hydroxyl group, a nitro group, CF$_3$, Cl, Br, F, a crosslinkable group, or a substituted or unsubstituted aromatic ring system containing 5 to 40 ring atoms or substituted or unsubstituted heteroaromatic ring system containing 5 to 40 ring atoms, or an aryloxy group containing 5 to 40 ring atoms or heteroaryloxy group containing 5 to 40 ring atoms, wherein one or more of the groups may form polycyclic aliphatic or aromatic ring systems with each other and/or with the ring bonded to the groups. One or more of the hydrogen atoms in various groups described above may also be further alternatively substituted by D.

In one embodiment, Ar$_5$ and Ar$_6$ are the same or different, and the Ar$_5$ or Ar$_6$ is each independently selected from the group consisting of: H, or a linear alkyl containing 1 to 10 C atoms, or an alkoxy containing 1 to 10 C atoms, or a thioalkoxy containing 1 to 10 C atoms, or a branched or cyclic alkyl containing 3 to 10 C atoms, or a substituted or unsubstituted silyl group, or a substituted keto group containing 1 to 10 C atoms, or an alkoxycarbonyl group containing 2 to 10 C atoms, or an aryloxycarbonyl group containing 7 to 10 C atom, a cyano group (—CN), a carbamoyl group (—C(=O)NH$_2$), a haloformyl group (—C(=O)—X, wherein X represents halogen atom), a formyl group (—C(=O)—H), a isocyano group, isocyanate, thiocyanate or isothiocyanate, a hydroxyl group, nitro group, CF$_3$, Cl, Br, F, a crosslinkable group, or a substituted or unsubstituted aromatic ring system containing 5 to 20 ring atoms or substituted or unsubstituted heteroaromatic ring system containing 5 to 20 ring atoms, or an aryloxy group containing 5 to 20 ring atoms or heteroaryloxy group containing 5 to 20 ring atoms, wherein one or more of the groups may form polycyclic aliphatic or aromatic ring systems with each other and/or with the ring bonded to the groups. One or more of the hydrogen atoms in various groups described above may be also further alternatively substituted by D.

In one embodiment, the Ar$_5$, Ar$_6$ are the same or different, and the Ar$_5$ or Ar$_6$ is each independently selected from the group consisting of: a linear alkyl containing 1 to 20 carbon atoms, a branched or cyclic alkyl containing 3 to 20 carbon atoms, and a substituted or unsubstituted aromatic ring system containing 5 to 40 ring atoms or substituted or unsubstituted heteroaromatic ring system containing 5 to 40 ring atoms.

In one embodiment, the Ar$_5$, Ar$_6$ are the same, and the Ar$_5$ or Ar$_6$ is each independently selected from the group consisting of: a linear alkyl containing 1 to 20 carbon atoms, and a branched or cyclic alkyl containing 3 to 20 carbon atoms.

The dotted line represents the single bond linked to the general formula (I).

In one embodiment, Ar$_1$—Ar$_4$ may be further alternatively selected from the structures as follows:

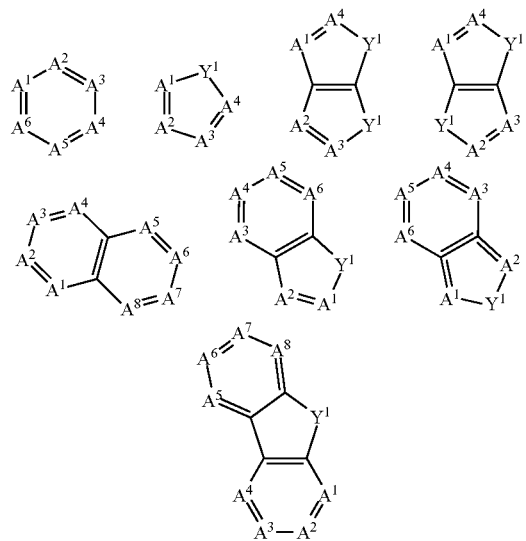

wherein
A$^1$, A$^2$, A$^3$, A$^4$, A$^5$, A$^6$, A$^7$, A$^8$ independently represent CR$^3$ or N;
Y$^1$ is selected from CR$^4$R$^5$, SiR$^4$R$^5$, NR$^3$, C(=O), S or O:
R$^3$, R$^4$ and R$^5$ are H, or a linear alkyl containing 1 to 20 C atoms, or an alkoxy containing 1 to 20 C atoms, or a thioalkoxy containing 1 to 20 C atoms, or a branched or cyclic alkyl containing 3 to 20 C atoms, or a silyl group, or a substituted keto group containing 1 to 20 C atoms, or a alkoxycarbonyl group containing 2 to 20 C atoms, or an aryloxycarbonyl group containing 7 to 20 C atom, a cyano group (—CN), a carbamoyl group (—C(=O)NH$_2$), a haloformyl group (—C(=O)—X, wherein X represents halogen atom), a formyl group (—C(=O)—H), an isocyano group, isocyanate, thiocyanate or isothiocyanate, a hydroxyl group, a nitro group, CF$_3$, Cl, Br, F, a crosslinkable group, or a substituted or unsubstituted aromatic ring system containing 5 to 40 ring atoms or substituted or unsubstituted heteroaromatic ring system containing 5 to 40 ring atoms, or an aryloxy group containing 5 to 40 ring atoms or heteroaryloxy group containing 5 to 40 ring atoms, wherein one or more of the groups R$^3$, R$^4$, R$^5$ may form monocyclic or polycyclic aliphatic or aromatic ring systems with each other and/or with the ring bonded to the groups.

In one embodiment, Ar$_1$-Ar$_4$ may further be selected from the following structures, wherein the H on the ring may be arbitrarily substituted:

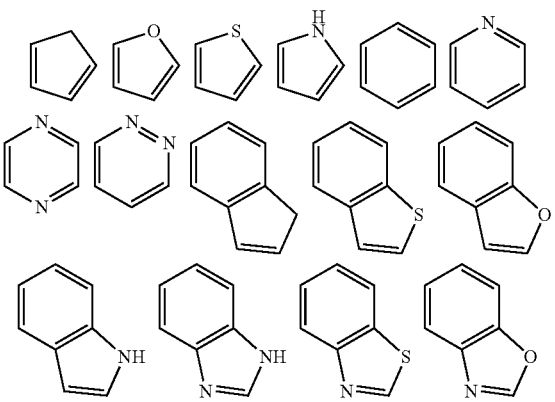

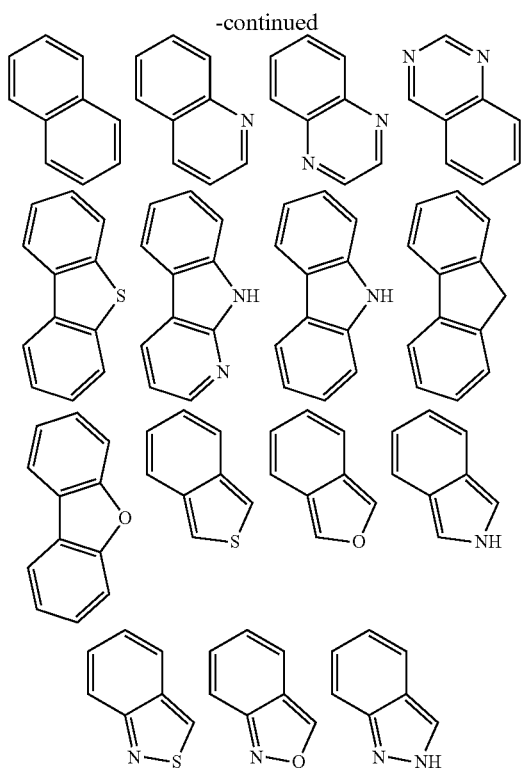

In one embodiment, an aromatic amine derivative is selected from the structures as shown in general formula (III):

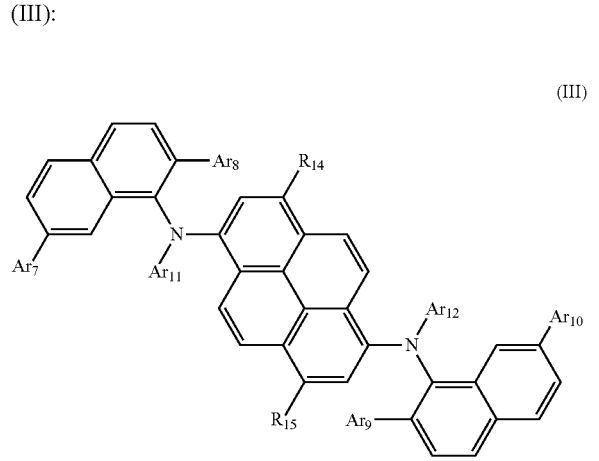

(III)

wherein

In one embodiment, $Ar_7$, $Ar_8$, $Ar_9$ and $Ar_{10}$ are the same or different from each other, the $Ar_7$, $Ar_8$, $Ar_9$ and $Ar_{10}$ are each independently selected from the group consisting of: H, or a linear alkyl containing 1 to 20 C atoms, or an alkoxy containing 1 to 20 C atoms, or a thioalkoxy containing 1 to 20 C atoms, or a branched or cyclic alkyl containing 3 to 20 C atoms, or a substituted or unsubstituted silyl group, or a substituted keto group containing 1 to 20 C atoms, or an alkoxycarbonyl group containing 2 to 20 C atoms, or an aryloxycarbonyl group containing 7 to 20 C atom, a cyano group (—CN), a carbamoyl group (—C(═O)NH$_2$), a haloformyl group (—C(═O)—X, wherein X represents halogen atom), a formyl group (—C(═O)—H), an isocyano group, isocyanate, thiocyanate or isothiocyanate, a hydroxyl group, a nitro group, $CF_3$, Cl, Br, F, a crosslinkable group, or a substituted or unsubstituted aromatic ring system containing 5 to 40 ring atoms or substituted or unsubstituted heteroaromatic ring system containing 5 to 40 ring atoms, or an aryloxy group containing 5 to 40 ring atoms or heteroaryloxy group containing 5 to 40 ring atoms, wherein one or more of the groups may form monocyclic or polycyclic aliphatic or aromatic ring systems with each other and/or with the ring bonded to the groups. One or more of the hydrogen atoms in various groups described above may be further substituted by D.

In one embodiment, $Ar_7$, $Ar_8$, $Ar_9$ and $Ar_{10}$ are the same or different from each other, the $Ar_7$, $Ar_8$, $Ar_9$ or $Ar_{10}$ is each independently selected from: H, or a linear alkyl containing 1 to 10 C atoms, or an alkoxy containing 1 to 10 C atoms, or a thioalkoxy containing 1 to 10 C atoms, or a branched or cyclic alkyl containing 3 to 10 C atoms, or a substituted or unsubstituted silyl group, or a substituted keto group containing 1 to 20 C atoms, or an alkoxycarbonyl group containing 2 to 10 C atoms, or an aryloxycarbonyl group containing 7 to 10 C atom, a cyano group (—CN), a carbamoyl group (—C(═O)NH$_2$), a haloformyl group (—C(═O)—X, wherein X represents halogen atom), a formyl group (—C(═O)—H), a isocyano group, isocyanate, thiocyanate or isothiocyanate, a hydroxyl group, a nitro group, ($CF_3$, Cl, Br, F, a crosslinkable group, or a substituted or unsubstituted aromatic ring system containing 5 to 20 ring atoms or substituted or unsubstituted heteroaromatic ring system containing 5 to 20 ring atoms, or an aryloxy group containing 5 to 20 ring atoms or heteroaryloxy group containing 5 to 20 ring atoms, wherein one or more of the groups may form monocyclic or polycyclic aliphatic or aromatic ring systems with each other and/or with the ring bonded to the groups. One or more of the hydrogen atoms in various groups described above may also be further substituted by D.

In one embodiment, $Ar_7$, $Ar_8$, $A_9$ and $Ar_{10}$ are the same or different from each other, the $Ar_7$, $Ar_8$, $Ar_9$ and $Ar_{10}$ are each independently selected from the group consisting of: H, D, methyl, ethyl, n-propyl, isopropyl, cyclopropyl, n-butyl, isobutyl, sec-butyl, tert-butyl, cyclobutyl, methylbutyl, n-pentyl, sec-pentyl, cyclopentyl, n-hexyl, cyclohexyl, n-heptyl, cycloheptyl, n-octyl, cyclooctyl, ethylhexyl, trifluoromethyl, pentafluoroethyl, trifluoroethyl, vinyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl, octynyl, methoxy, trifluoromethoxy, ethoxy, n-propoxy, isopropoxy, n-butoxy, Isobutoxy, sec-butoxy, tert-butoxy or methylbutoxy, trimethylsilane, or substituted or unsubstituted aryl or heteroaryl groups with the following original nucleus structures:

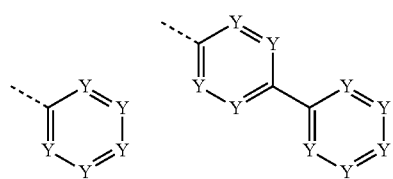

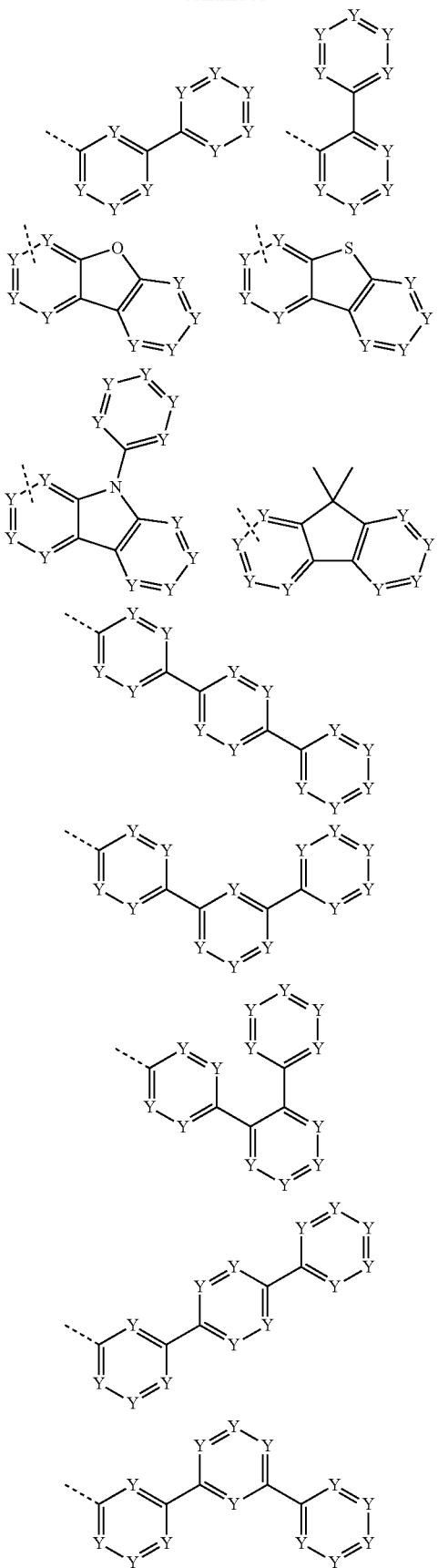
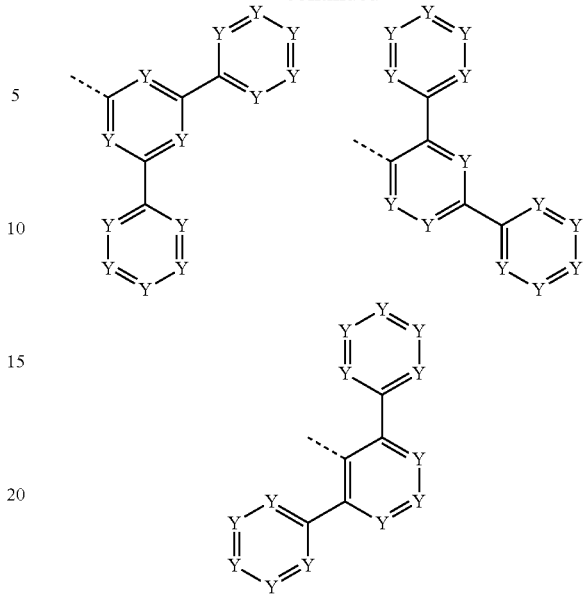

Y is selected from $CR_{31}$ or N, but there are no two adjacent Ys that are both N at the same time;

$R_{31}$ is selected from group consisting of H, or a linear alkyl containing 1 to 20 C atoms, or an alkoxy containing 1 to 20 C atoms, or a thioalkoxy containing 1 to 20 C atoms, or a branched or cyclic alkyl containing 3 to 20 C atoms, or a substituted or unsubstituted silyl group, or a substituted keto group containing 1 to 20 C atoms, or an alkoxycarbonyl group containing 2 to 20 C atoms, or an aryloxycarbonyl group containing 7 to 20 C atom, a cyano group, carbamoyl group, a haloformyl group, formyl group, a isocyano group, isocyanate, thiocyanate or isothiocyanate, a hydroxyl group, a nitro group, $CF_3$, Cl, Br, F, a crosslinkable group, or a substituted or unsubstituted aromatic ring system containing 5 to 40 ring atoms or substituted or unsubstituted heteroaromatic ring system containing 5 to 40 ring atoms, or an aryloxy group containing 5 to 40 ring atoms or heteroaryloxy group containing 5 to 40 ring atoms; one or more of the groups in $R_{31}$ may form monocyclic or polycyclic aliphatic or aromatic ring systems with each other and/or with the ring bonded to the groups; one or more of the H in $R_{3f}$ are alternatively further substituted by D; the dotted line represents the single bond linking the group to the N atom of the aromatic amine.

In one embodiment, $R_{31}$ is selected from group consisting of H, or a linear alkyl containing 1 to 10 C atoms, or an alkoxy containing 1 to 10 C atoms, or a thioalkoxy containing 1 to 10 C atoms, or a branched or cyclic alkyl containing 3 to 10 C atoms, or a substituted or unsubstituted silyl group, or a substituted keto group containing 1 to 10 C atoms, or an alkoxycarbonyl group containing 2 to 10 C atoms, or an aryloxycarbonyl group containing 7 to 10 C atom, a cyano group (—CN), a carbamoyl group (—C(=O)NH2), a haloformyl group (—C(=O)—X, wherein X represents halogen atom), a formyl group (—C(=O)—H), a isocyano group, isocyanate, thiocyanate or isothiocyanate, a hydroxyl group, a nitro group, $CF_3$, Cl, Br, F, a crosslinkable group, or a substituted or unsubstituted aromatic ring system containing 5 to 20 ring atoms or substituted or unsubstituted heteroaromatic ring system containing 5 to 20 ring atoms, or an aryloxy group containing 5 to 20 ring atoms or heteroaryloxy group containing 5 to 20 ring atoms, wherein one or more of the groups may form monocyclic or polycyclic aliphatic or aromatic ring systems with each other and/or with the ring bonded to the groups; one or more of the H in various group described above may also be further substituted by D.

In one embodiment, the $Ar_7$, $Ar_8$, $Ar_9$ and $Ar_{10}$ are each independently selected from the following structures:

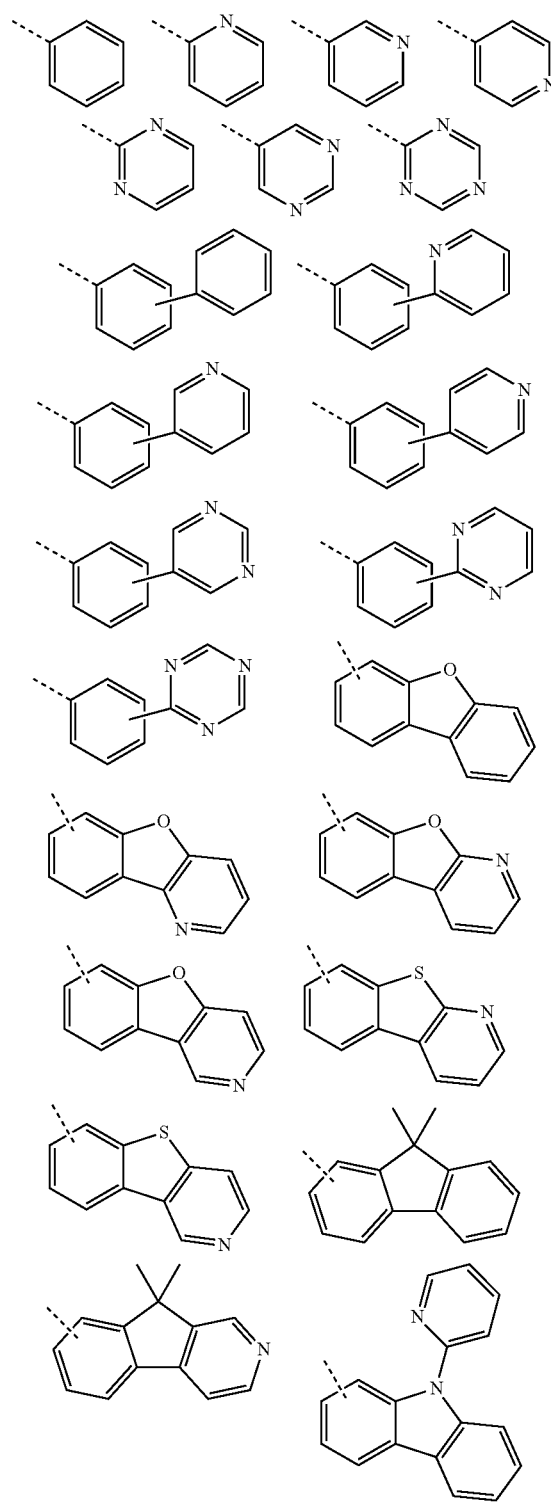

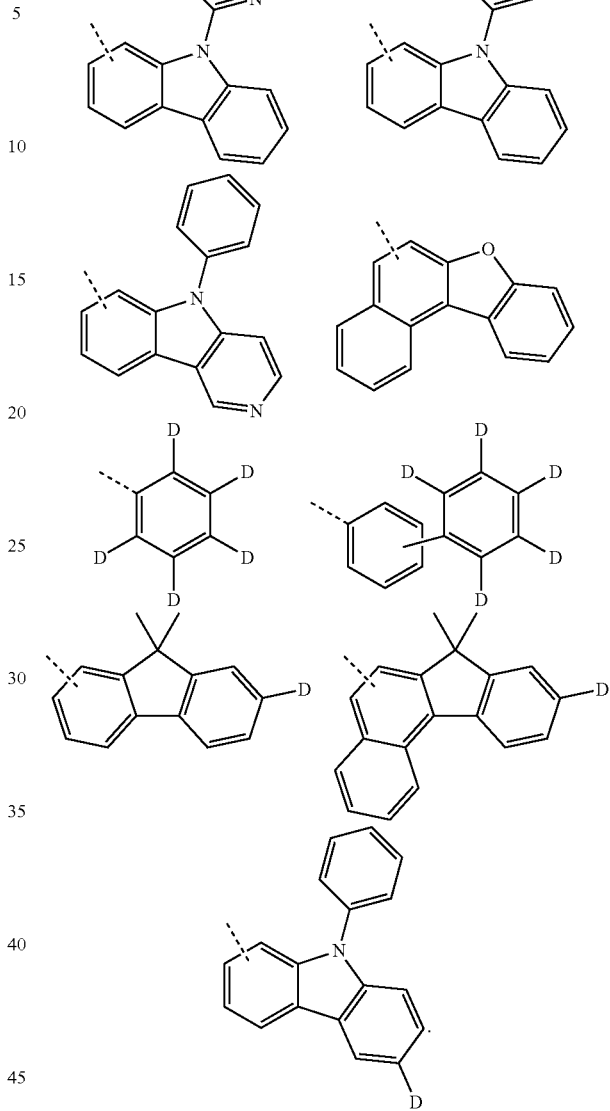

In the above structures, the dotted line represents the single bond linking the group to the N atom of the aromatic amine.

In one embodiment, the $Ar_7$, $Ar_8$, $Ar_9$ and $Ar_{10}$ are each independently selected from the group consisting of: H, D, methyl, isopropyl, isobutyl, sec-butyl, tert-butyl, trimethylsilane, cyclopentyl, cyclohexyl, phenyl or phenyl with five hydrogen atoms substituted by deuterium atoms.

$Ar_{11}$, $Ar_{12}$, can be the same or different, the $Ar_{11}$. $Ar_{12}$ are each independently selected from the group consisting of: H, a substituted or unsubstituted aromatic ring system containing 5 to 40 ring atoms or substituted or unsubstituted heteroaromatic ring system containing 5 to 40 ring atoms, or an aryloxy group containing from 5 to 40 ring atoms or heteroaryloxy group containing from 5 to 40 ring atoms, wherein one or more of the groups may form monocyclic or polycyclic aliphatic or aromatic ring systems with each other and/or with a ring bonded to the group. One or more of the hydrogen atoms in various groups described above may be further substituted by D.

In one embodiment, $Ar_{11}$, $Ar_{12}$ can be the same or different, the $Ar_{11}$, $Ar_{12}$ are each independently selected from the group consisting of: H, a substituted or unsubstituted aromatic ring system containing 5 to 20 ring atoms or substituted or unsubstituted heteroaromatic ring system containing 5 to 20 ring atoms, or an aryloxy group containing from 5 to 20 ring atoms or heteroaryloxy group containing from 5 to 20 ring atoms, wherein one or more of the groups may form monocyclic or polycyclic aliphatic or aromatic ring systems with each other and/or with a ring bonded to the group. One or more of the hydrogen atoms in various groups described above may be further substituted by D.

In one embodiment, $Ar_{11}$, $Ar_{12}$ can be the same or different, the $Ar_{11}$, $Ar_{12}$ are each independently selected from the group consisting of: H, a substituted or unsubstituted aromatic ring system containing 5 to 15 ring atoms or substituted or unsubstituted heteroaromatic ring system containing 5 to 15 ring atoms, or an aryloxy group containing from 5 to 15 ring atoms or heteroaryloxy group containing from 5 to 15 ring atoms, wherein one or more of the groups may form monocyclic or polycyclic aliphatic or aromatic ring systems with each other and/or with a ring bonded to the group. One or more of the H in various groups described above may also be further substituted by D.

When the $Ar_{11}$ or $Ar_{12}$ is each independently selected from the following structures:

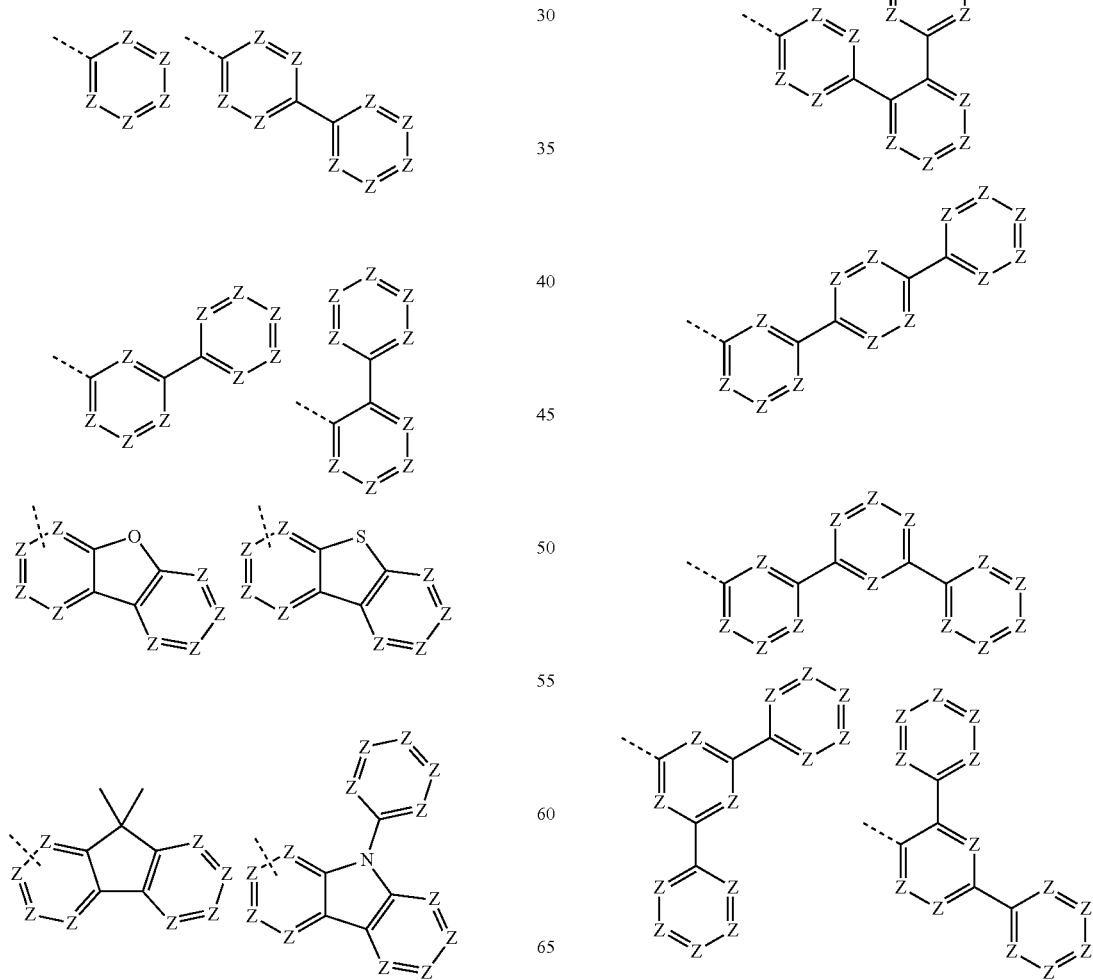

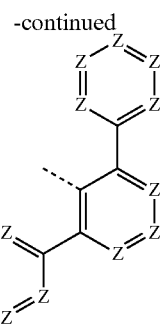

Z is selected from $CR_{34}$ or N, but there are no two adjacent Zs that are both N at the same time;

$R_{32}$, $R_{33}$ or $R_{34}$ independently selected from the group consisting of: H, or a linear alkyl containing 1 to 20 C atoms, or an alkoxy containing 1 to 20 C atoms, or a thioalkoxy containing 1 to 20 C atoms, or a branched or cyclic alkyl containing 3 to 20 C atoms, or a substituted or unsubstituted silyl group, or a substituted keto group containing 1 to 20 C atoms, or an alkoxycarbonyl group containing 2 to 20 C atoms, or an aryloxycarbonyl group containing 7 to 20 C atom, a cyano group, a carbamoyl group, a haloformyl group, a formyl group, a isocyano group, isocyanate, thiocyanate or isothiocyanate, a hydroxyl group, a nitro group, $CF_3$, Cl, Br, F, a crosslinkable group, or a substituted or unsubstituted aromatic ring system containing 5 to 40 ring atoms or substituted or unsubstituted heteroaromatic ring system containing 5 to 40 ring atoms, or an aryloxy group containing 5 to 40 ring atoms or heteroaryloxy group containing 5 to 40 ring atoms; one or more of the groups in the $R_{32}$, $R_{33}$ or $R_{34}$ may form monocyclic or polycyclic aliphatic or aromatic ring systems with each other and/or with the ring bonded to the groups; one or more of the H in the $R_{32}$, $R_{33}$ or $R_{34}$ are alternatively further substituted by D;

P is a saturated cycloalkane or heterocycloalkane containing 3 to 10 ring atoms; the dotted line represents the single bond linking the group to the N atom of the aromatic amine.

In one embodiment, $R_{32}$, $R_{33}$ and $R_{34}$ are each independently selected from the group consisting of: H, or a linear alkyl containing 1 to 10 C atoms, or an alkoxy containing 1 to 10 C atoms, or a thioalkoxy containing 1 to 10 C atoms, or a branched or cyclic alkyl containing 3 to 10 C atoms, or a substituted or unsubstituted silyl group, or a substituted keto group containing 1 to 10 C atoms, or an alkoxycarbonyl group containing 2 to 10 C atoms, or an aryloxycarbonyl group containing 7 to 10 C atom, a cyano group (—CN), a carbamoyl group (—C(=O)NH$_2$), a haloformyl group (—C(=O)—X, wherein X represents halogen atom), a formyl group (—C(=O)—H), an isocyano group, isocyanate, thiocyanate or isothiocyanate, a hydroxyl group, a nitro group, $CF_3$, Cl, Br, F, a crosslinkable group, or a substituted or unsubstituted aromatic ring system containing 5 to 20 ring atoms or substituted or unsubstituted heteroaromatic ring system containing 5 to 20 ring atoms, or an aryloxy group containing 5 to 20 ring atoms or heteroaryloxy group containing 5 to 20 ring atoms, wherein one or more of the groups may form monocyclic or polycyclic aliphatic or aromatic ring systems with each other and/or with the ring bonded to the groups. One or more of the H in various groups described above may also be further substituted by D.

P is a saturated cycloalkane or heterocycloalkane containing 3 to 10 ring atoms, further, P is a saturated cycloalkane or heterocycloalkane containing 3 to 8 C atoms, still further, P is a saturated cycloalkane or a heterocycle containing 5 to 6 C atoms. The dotted line represents the single bond linking the group to the N atom of the aromatic amine.

The $Ar_{11}$ or $Ar_{12}$ is each independently selected from the following structures:

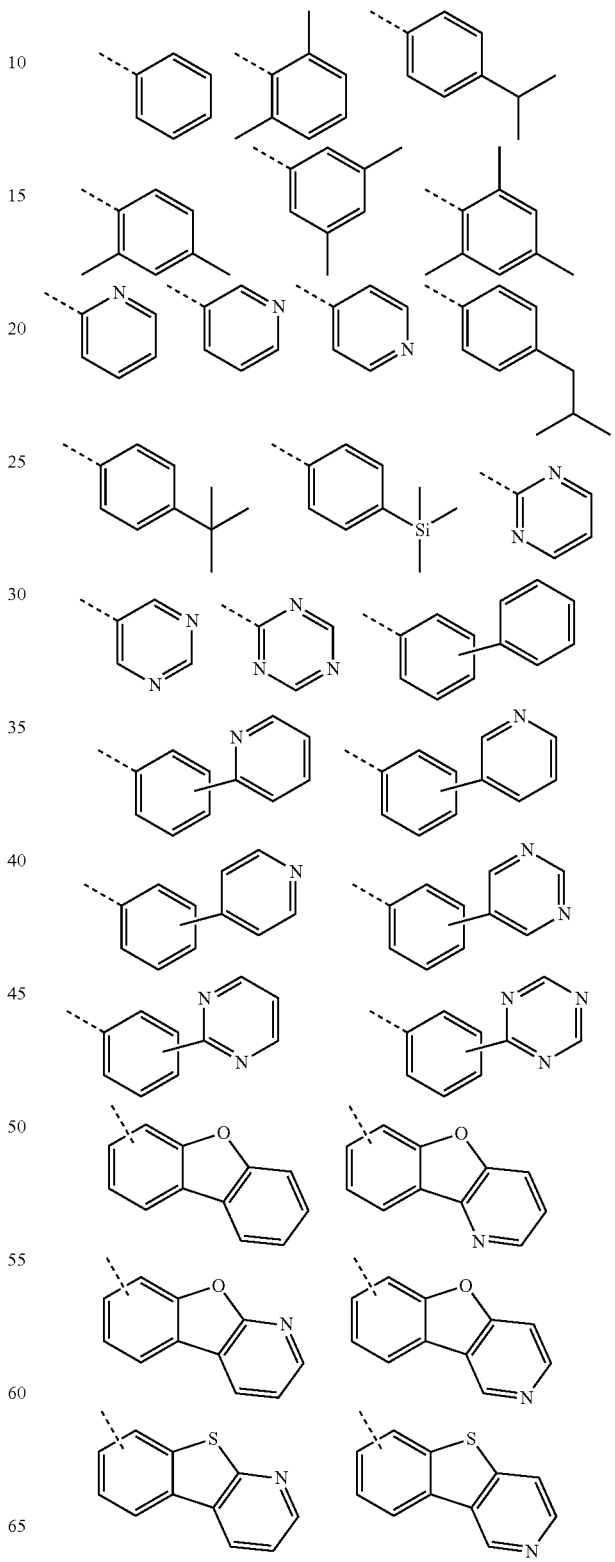

-continued
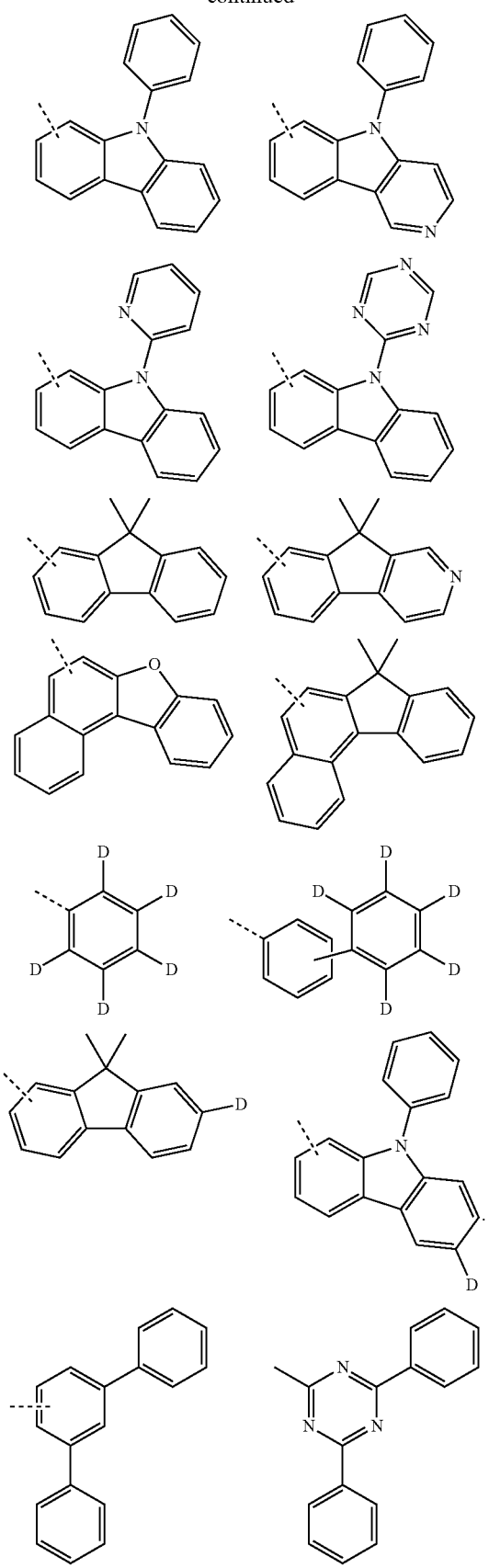
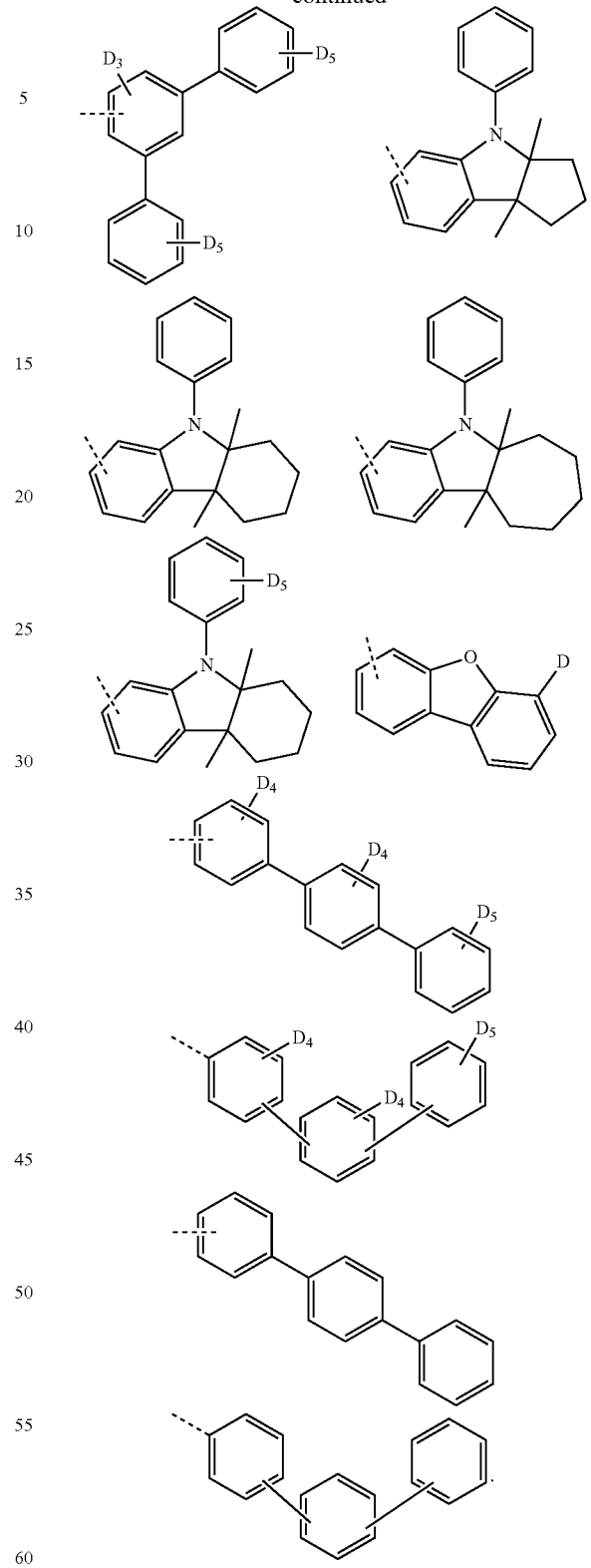
$R_{11}$ and $R_{15}$ are the same or different, and the $R_{11}$ or $R_{15}$ is each independently selected from the group consisting of: H, or a linear alkyl containing 1 to 20 C atoms, or an alkoxy containing 1 to 20 C atoms, or a thioalkoxy containing 1 to 20 C atoms, or a branched or cyclic alkyl containing 3 to 20 C atoms, or a substituted or unsubstituted silyl group, or a substituted keto group containing 1 to 20 C atoms, or an alkoxycarbonyl group containing 2 to 20 C atoms, or an aryloxycarbonyl group containing 7 to 20 C atom, a cyano group (—CN), a carbamoyl group (—C(=O)NH$_2$), a haloformyl group (—C(=O)—X, wherein X represents halogen atom), a formyl group (—C(=O)—H), a isocyano group, isocyanate, thiocyanate or isothiocyanate, a hydroxyl group, a nitro group, CF$_3$, Cl, Br, F, a crosslinkable group, or a substituted or unsubstituted aromatic ring system containing 5 to 40 ring atoms or substituted or unsubstituted heteroaromatic ring system containing 5 to 40 ring atoms, or an aryloxy group containing 5 to 40 ring atoms or heteroaryloxy group containing 5 to 40 ring atoms, wherein one or more of the groups may form monocyclic or polycyclic aliphatic or aromatic ring systems with each other and/or with the ring bonded to the groups. One or more of the H in various groups described above may also be further substituted by D.

In one embodiment, R$_{14}$ and R$_{15}$ are the same or different, and the R$_{14}$ or R$_{15}$ is each independently selected from the group consisting of: H, or a linear alkyl containing 1 to 10 C atoms, or an alkoxy containing 1 to 10 C atoms, or a thioalkoxy containing 1 to 10 C atoms, or a branched or cyclic alkyl containing 3 to 10 C atoms, or a substituted or unsubstituted silyl group, or a substituted keto group containing 1 to 10 C atoms, or an alkoxycarbonyl group containing 2 to 20 C atoms, or an aryloxycarbonyl group containing 7 to 10 C atom, a cyano group (—CN), a carbamoyl group (—C(=O)NH$_2$), a haloformyl group (—C(=O)—X, wherein X represents halogen atom), a formyl group (—C(=O)—H), a isocyano group, isocyanate, thiocyanate or isothiocyanate, a hydroxyl group, a nitro group, CF$_3$, Cl, Br, F, a crosslinkable group, or a substituted or unsubstituted aromatic ring system containing 5 to 20 ring atoms or substituted or unsubstituted heteroaromatic ring system containing 5 to 20 ring atoms, or an aryloxy group containing 5 to 20 ring atoms or heteroaryloxy group containing 5 to 20 ring atoms, wherein one or more of the groups may form monocyclic or polycyclic aliphatic or aromatic ring systems with each other and/or with the ring bonded to the groups. One or more of the H in various groups described above may also be further substituted by D.

In an embodiment, the R$_{14}$, R$_{15}$ described above may be the same or different, and R$_{14}$ or R$_{15}$ is each independently selected from: a linear or branched alkane or cycloalkane with 3 to 6 carbon atoms.

In an embodiment, the R$_{14}$, R$_{15}$ described above may be the same or different, and R$_{14}$ or R$_{15}$ is each independently selected from: a linear or branched alkane or cycloalkane with 3 to 5 carbon atom s.

In an embodiment, the R$_{14}$, R$_{15}$ described above may be the same or different, and R$_{14}$ or R$_{15}$ is each independently selected from: a linear or branched alkane or cycloalkane with 3 to 4 carbon atoms.

In an embodiment, the R$_{14}$, R$_{15}$ described above may be the same or different, and R$_{14}$ or R$_{15}$ is each independently selected from: aromatic groups containing 5-20 ring atoms or heteroaromatic groups containing 5-20 ring atoms.

In an embodiment, the R$_{14}$, R$_{15}$ described above may be the same or different, and R$_{14}$ or R$_{15}$ is each independently selected from: aromatic groups containing 5-12 ring atoms or heteroaromatic groups containing 5-12 ring atoms.

In an embodiment, the R$_{14}$, R$_{15}$ described above may be the same or different, and R$_{14}$ or R$_{15}$ is each independently selected from: aromatic groups containing 5-12 ring atoms or heteroaromatic groups containing 5-12 ring atoms, which also contain at least one D atoms.

In one embodiment, R$_{14}$, R$_{15}$ described above are the same or different, and the R$_{14}$, R$_{15}$ are each independently selected from the group consisting of: H, D, methyl, ethyl, n-propyl, isopropyl, cyclopropyl, n-butyl, isobutyl, sec-butyl, tert-butyl, cyclobutyl, methylbutyl, n-pentyl, sec-pentyl, cyclopentyl, n-hexyl, cyclohexyl, n-heptyl, cycloheptyl, n-octyl, cyclooctyl, ethylhexyl, trifluoromethyl, pentafluoroethyl, trifluoroethyl, vinyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl, octynyl, methoxy, trifluoromethoxy, ethoxy, n-propoxy, isopropoxy, n-butoxy, Isobutoxy, sec-butoxy, tert-butoxy or methylbutoxy, trimethylsilane, or substituted or unsubstituted aryl or heteroaryl groups with the following structures:

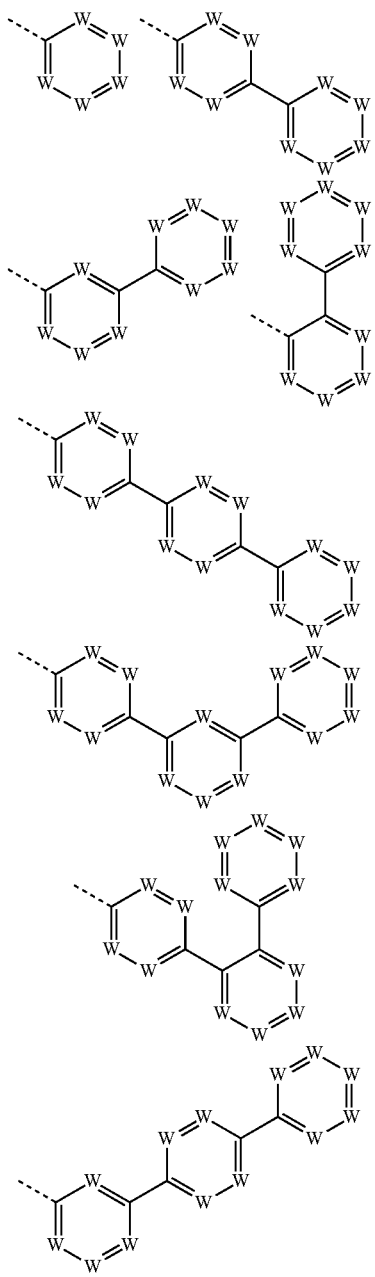

-continued

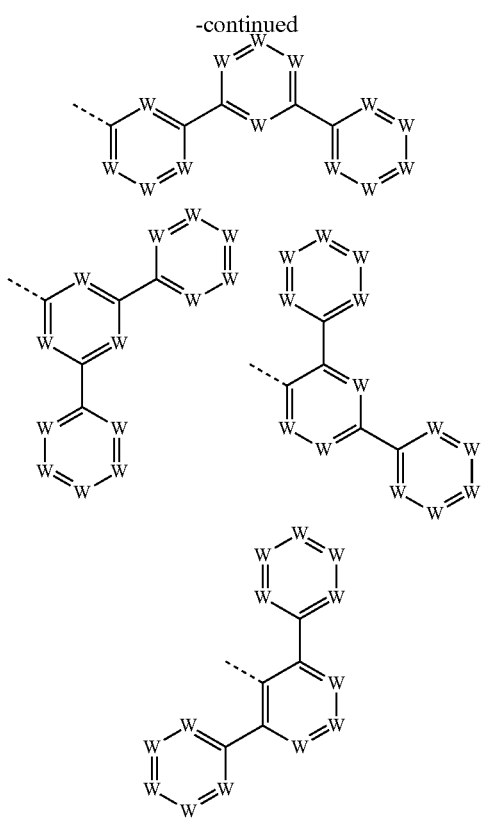

W is selected from CR$_{35}$ or N, but there are no two adjacent Ws that are both N at the same time;

R$_{35}$ is selected from the group consisting of H, or a linear alkyl containing 1 to 20 C atoms, or an alkoxy containing 1 to 20 C atoms, or a thioalkoxy containing 1 to 20 C atoms, or a branched or cyclic alkyl containing 3 to 20 C atoms, or a substituted or unsubstituted silyl group, or a substituted keto group containing 1 to 20 C atoms, or an alkoxycarbonyl group containing 2 to 20 C atoms, or an aryloxycarbonyl group containing 7 to 20 C atom, a cyano group, a carbamoyl group, a haloformyl group, a formyl group, an isocyano group, isocyanate, thiocyanate or isothiocyanate, a hydroxyl group, a nitro group, CF$_3$, Cl, Br, F, a crosslinkable group, or a substituted or unsubstituted aromatic ring system containing 5 to 40 ring atoms or substituted or unsubstituted heteroaromatic ring system containing 5 to 40 ring atoms, or an aryloxy group containing 5 to 40 ring atoms or heteroaryloxy group containing 5 to 40 ring atoms; one or more of the groups in the R$_{35}$ may form monocyclic or polycyclic aliphatic or aromatic ring systems with each other and/or with the ring bonded to the groups; one or more H in the R$_{35}$ may also be further substituted by D; the dotted line represents the single bond linking the group to other groups.

In one embodiment, R$_{35}$ is selected from the group consisting of H, or a linear alkyl containing 1 to 10 C atoms, or an alkoxy containing 1 to 10 C atoms, or a thioalkoxy containing 1 to 10 C atoms, or a branched or cyclic alkyl containing 3 to 10 C atoms, or a substituted or unsubstituted silyl group, or a substituted keto group containing 1 to 10 C atoms, or an alkoxycarbonyl group containing 2 to 10 C atoms, or an aryloxycarbonyl group containing 7 to 10 C atom, a cyano group (—CN), a carbamoyl group (—C(=O) NH$_2$), a haloformyl group (—C(=O)—X, wherein X represents halogen atom), a formyl group (—C(=O)—H), an isocyano group, isocyanate, thiocyanate or isothiocyanate, a hydroxyl group, a nitro group, CF$_3$, Cl, Br, F, a crosslinkable group, or a substituted or unsubstituted aromatic ring system containing 5 to 20 ring atoms or substituted or unsubstituted heteroaromatic ring system containing 5 to 20 ring atoms, or an aryloxy group containing 5 to 20 ring atoms or heteroaryloxy group containing 5 to 20 ring atoms, wherein one or more of the groups may form monocyclic or polycyclic aliphatic or aromatic ring systems with each other and/or with the ring bonded to the groups. One or more of the H in various groups described above may also be further substituted by D. The dotted line represents the single bond linking the group to the N atom of the aromatic amine.

In one embodiment, the R$_{14}$, R$_{15}$ are each independently selected from the group consisting of: H, D, isopropyl, isobutyl, tert-butyl, tetramethylsilane or substituted or unsubstituted aryl or heteroaryl having the following structures:

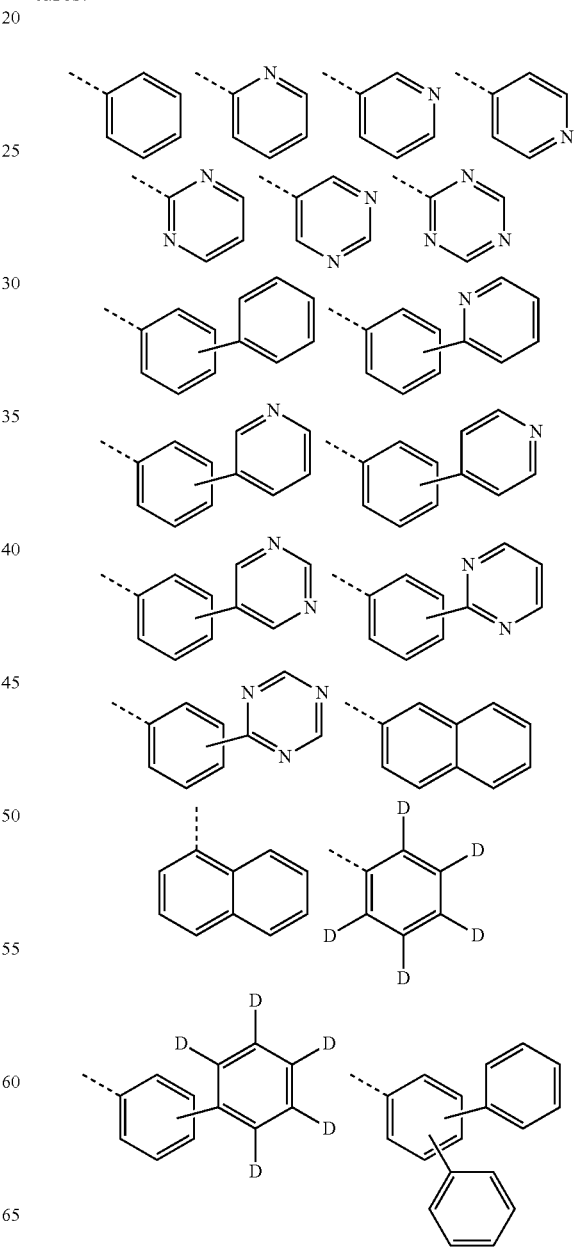

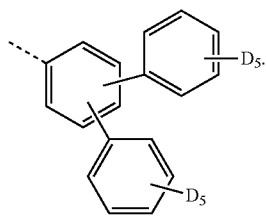

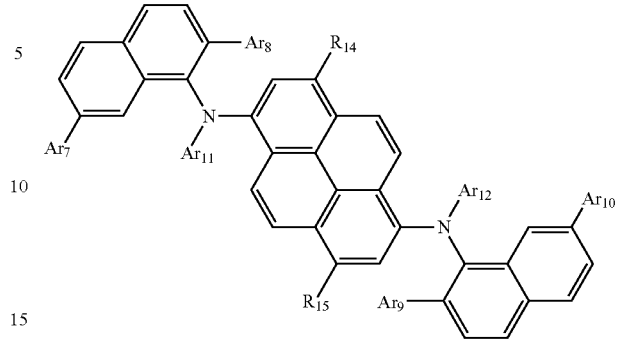

In one embodiment, the $R_{14}$ and $R_{15}$ are the same or different, and the $R_{14}$ and $R_{15}$ are each independently selected from the group consisting of: H, D, isopropyl, isobutyl, tert-butyl, tetramethylsilane, benzene, diphenylene, a benzene containing at least one D atom or a diphenylene containing at least one D atom.

In one embodiment, the $R_{14}$ and $R_{15}$ are the same, and selected from the group consisting of: H, D, isopropyl, isobutyl, tert-butyl, tetramethylsilane, benzene, diphenylene, a benzene containing at least one D atom or a diphenylene containing at least one D atom.

In one embodiment, both $R_{14}$ and $R_{15}$ are selected from H. In one embodiment, both $R_{14}$ and $R_{15}$ are selected from D. In one embodiment, both $R_{14}$ and $R_{15}$ are selected from isopropyl. In one embodiment, both $R_{14}$ and $R_{15}$ are selected from isobutyl. In one embodiment, both $R_{14}$ and $R_{15}$ are selected from tert-butyl. In one embodiment, both $R_{14}$ and $R_{15}$ are selected from tetramethylsilane. In one embodiment, both $R_{14}$ and $R_{15}$ are selected from benzene. In one embodiment, both $R_{14}$ and $R_{15}$ are selected from diphenylene. In one embodiment, both $R_{14}$ and $R_{15}$ are selected from benzene or diphenylene containing at least one D atom.

In one embodiment, the compound described above is at least partially deuterated. In one embodiment, 10% of the H is deuterated; in one embodiment, 20% of the H is deuterated; in one embodiment, 30% of the H is deuterated; in one embodiment, 40% of H is deuterated.

In one embodiment, in the structure as shown in general formula (III):

$Ar_7$, $Ar_8$, $Ar_9$, and $Ar_{10}$ are identical to each other; selected from: methyl, phenyl, or isopropyl;

$Ar_{11}$ and $Ar_{12}$ are identical to each other and selected from the following substituent groups:

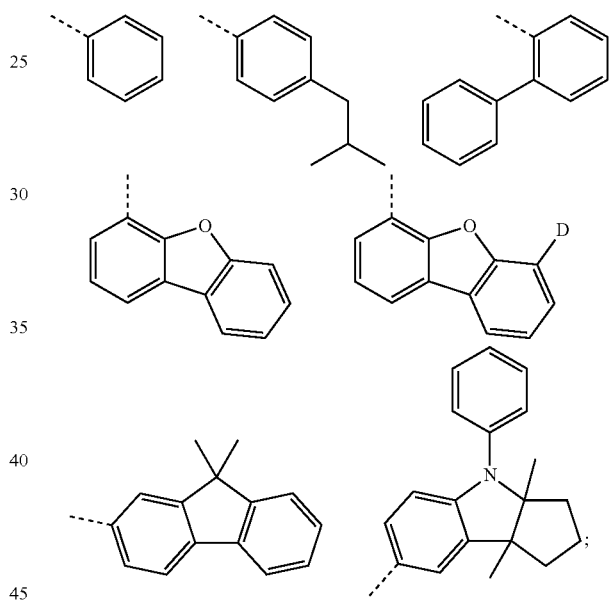

The $R_{10}$ and $R_{15}$ are hydrogen atoms or isopropyl or isobutyl or tert-butyl.

A specific example of the aromatic amine derivative according to the present disclosure is as follows, but is not limited thereto:

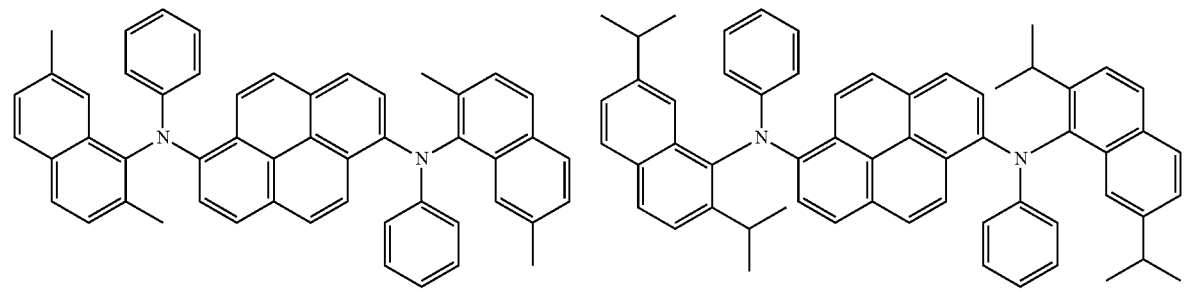

-continued
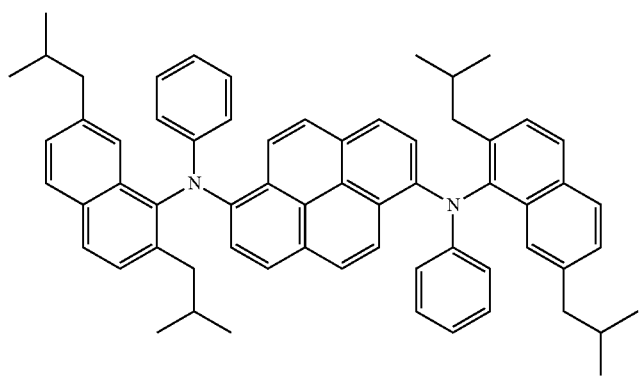
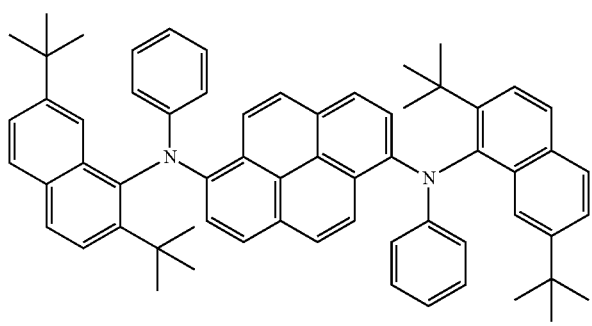
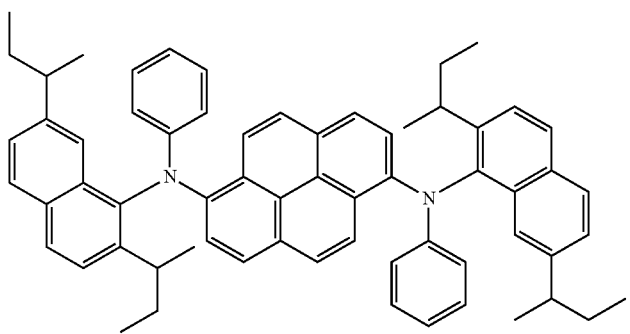
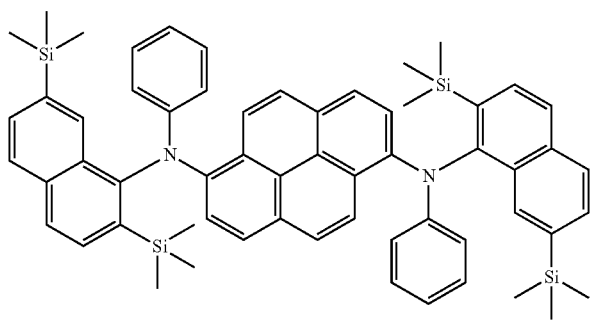

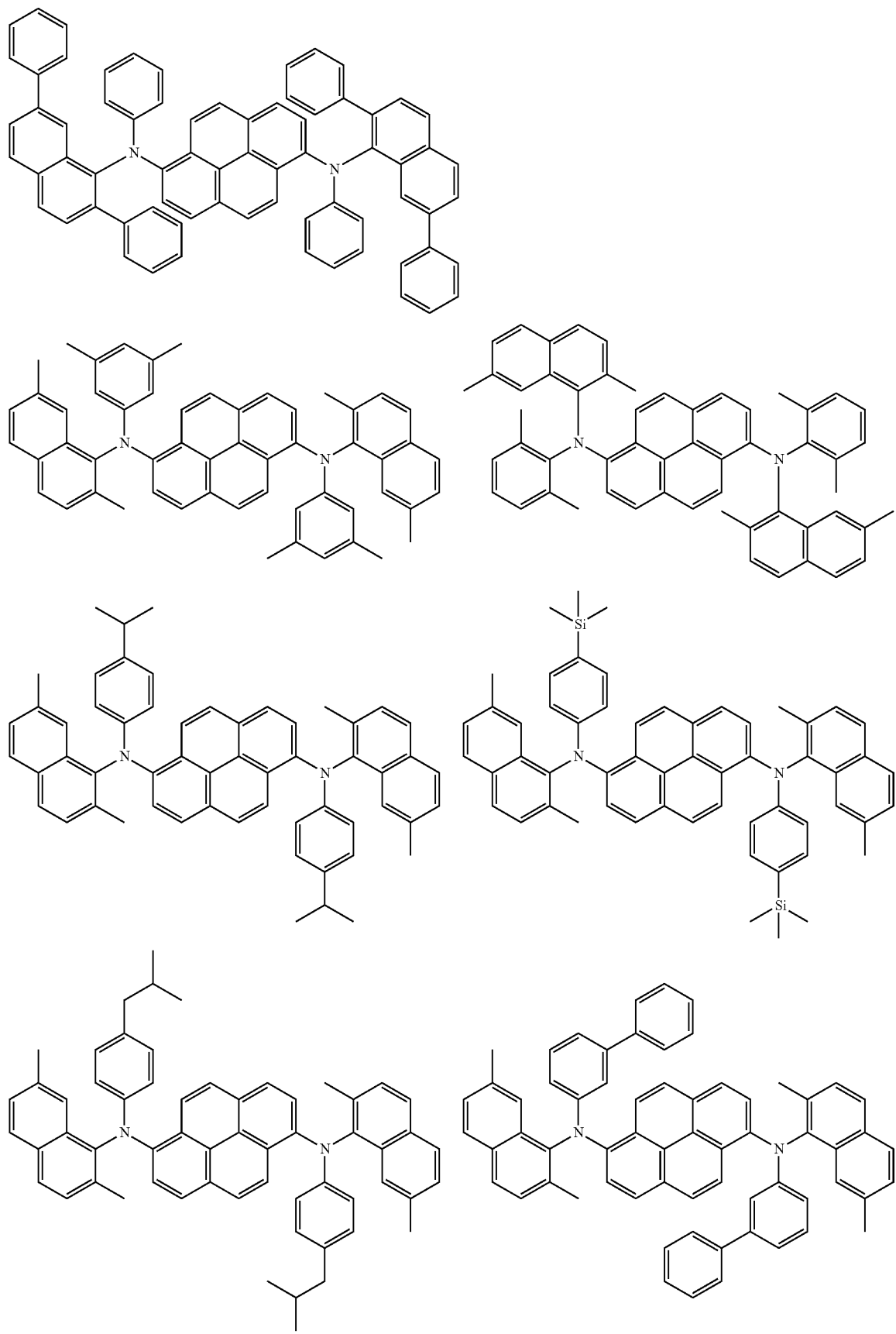

-continued
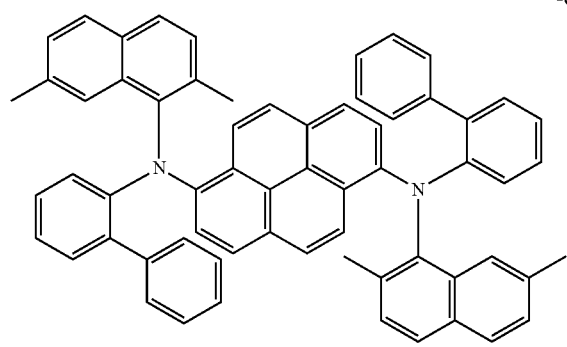
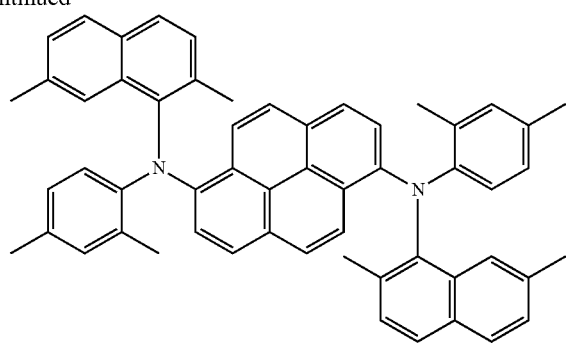
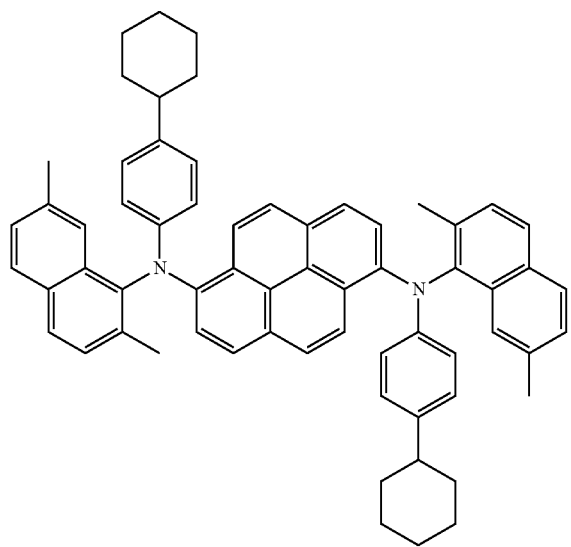
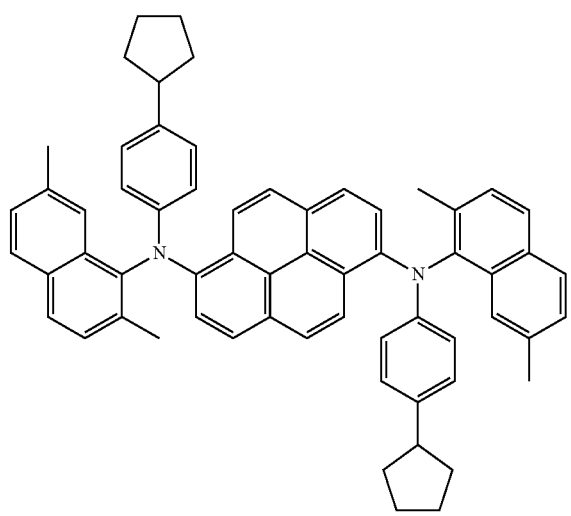
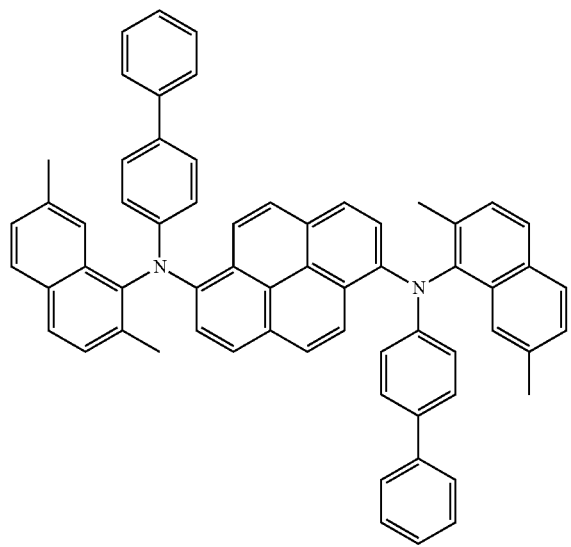
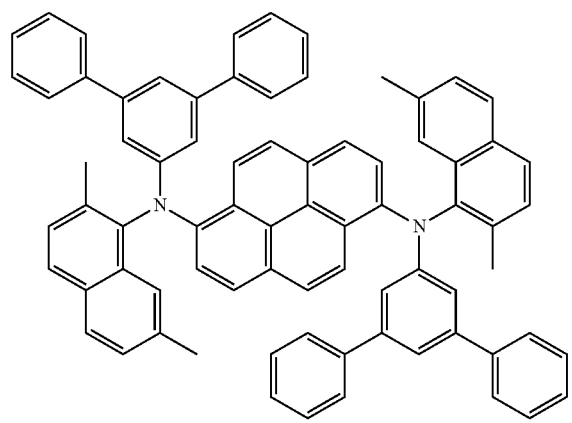

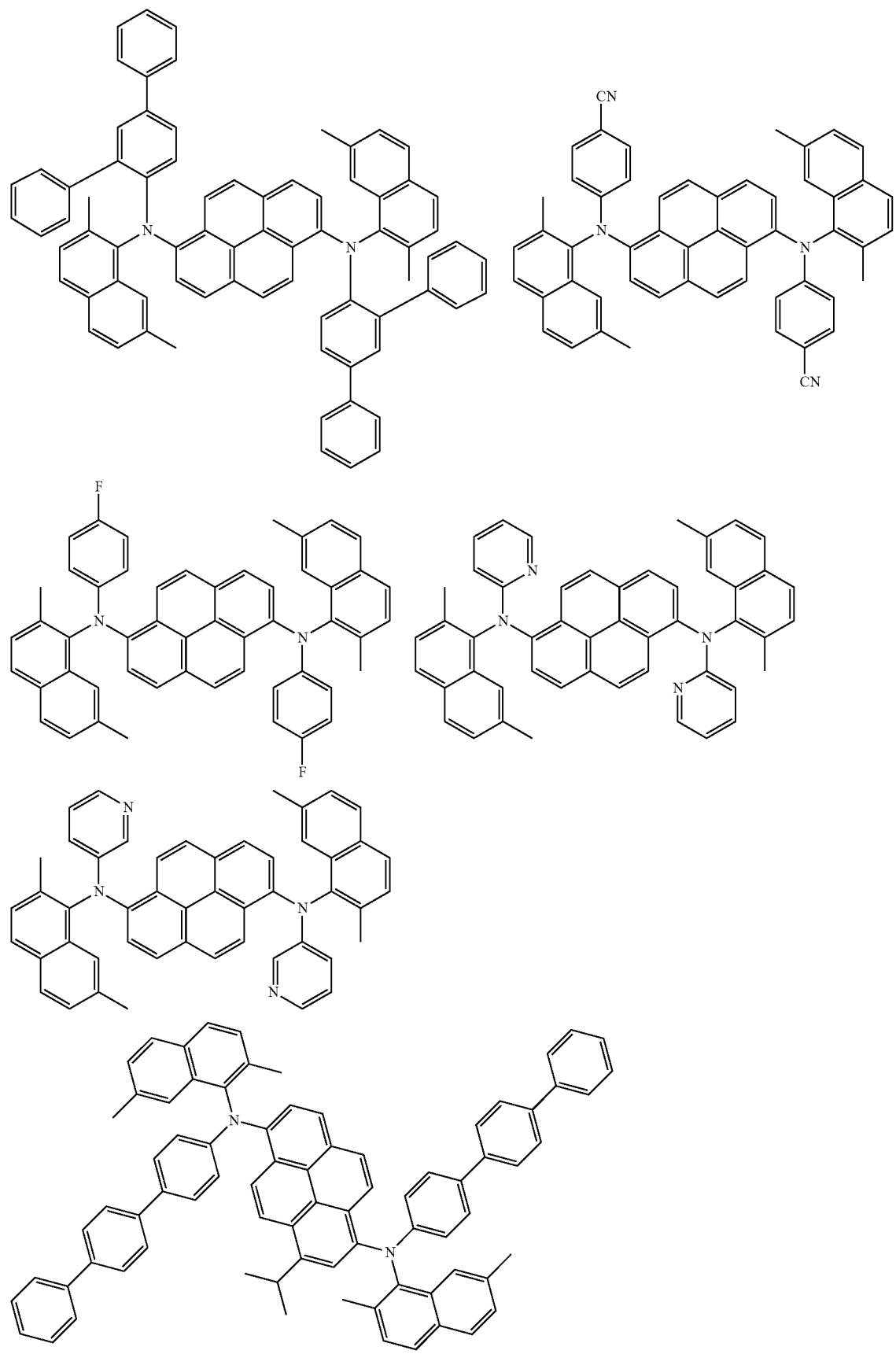

-continued
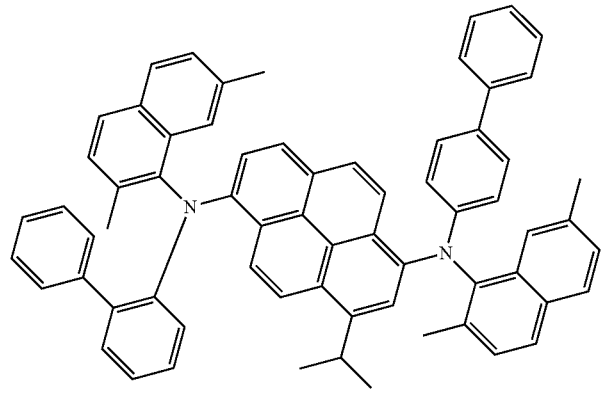
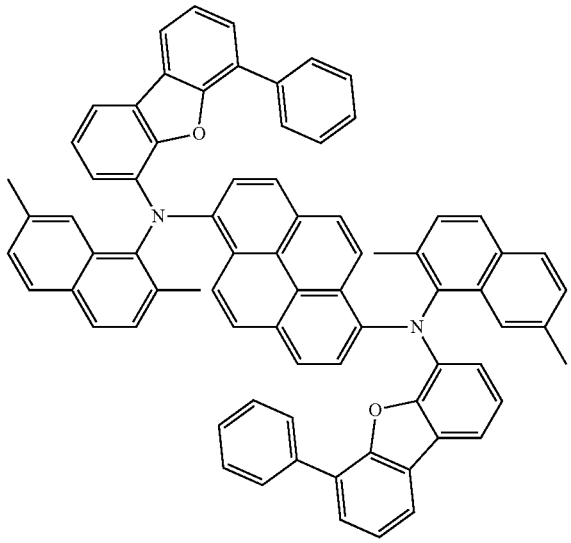
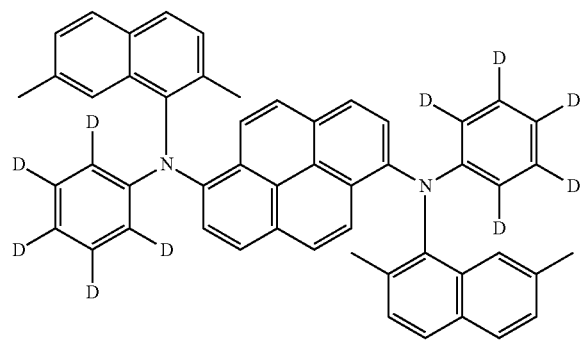
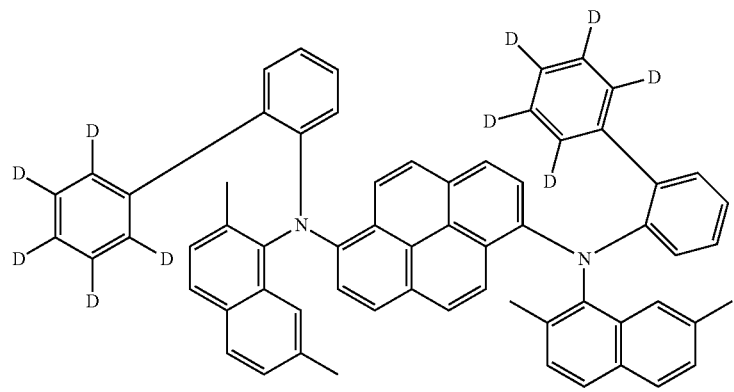

-continued
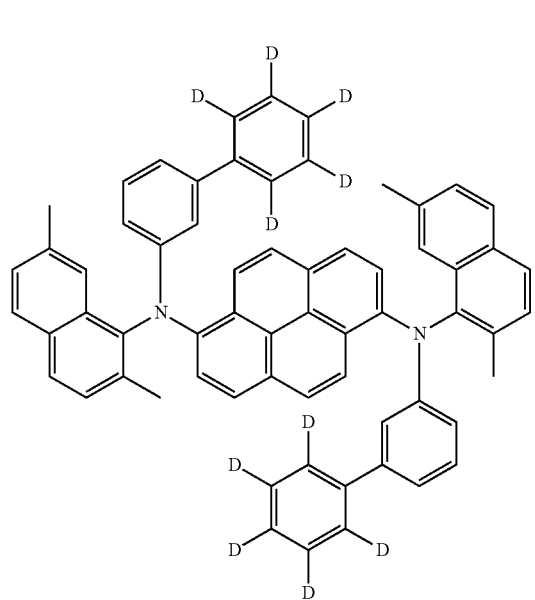
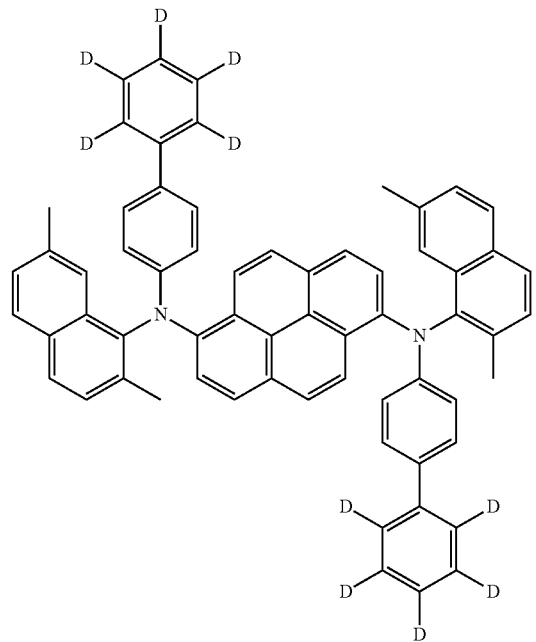
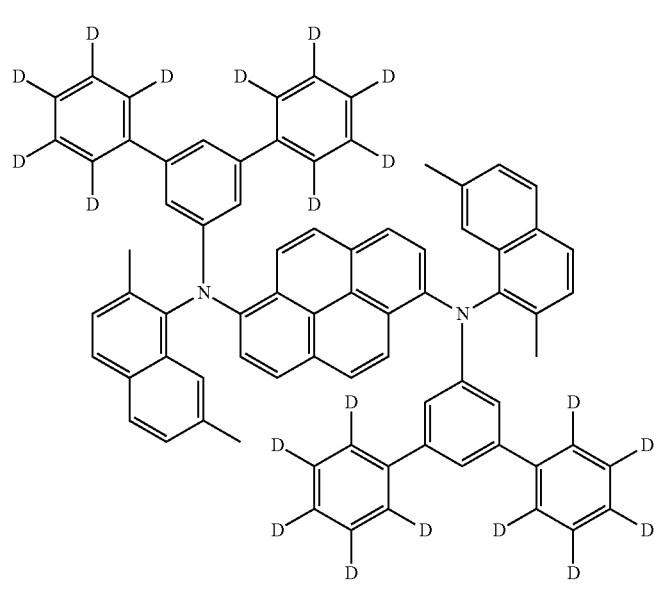
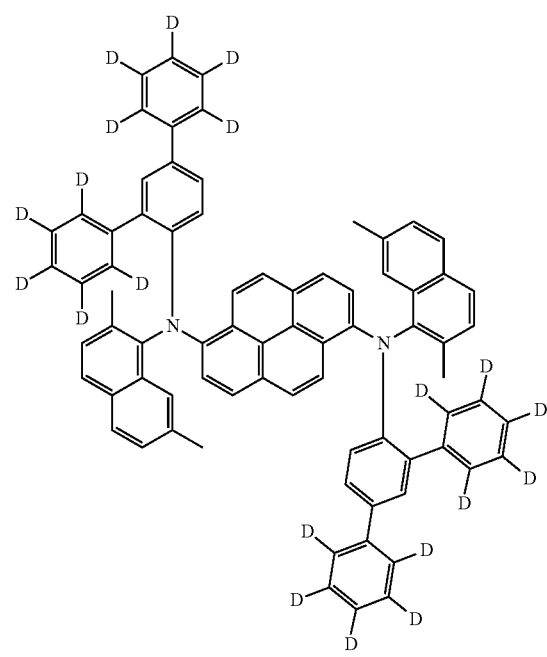

-continued
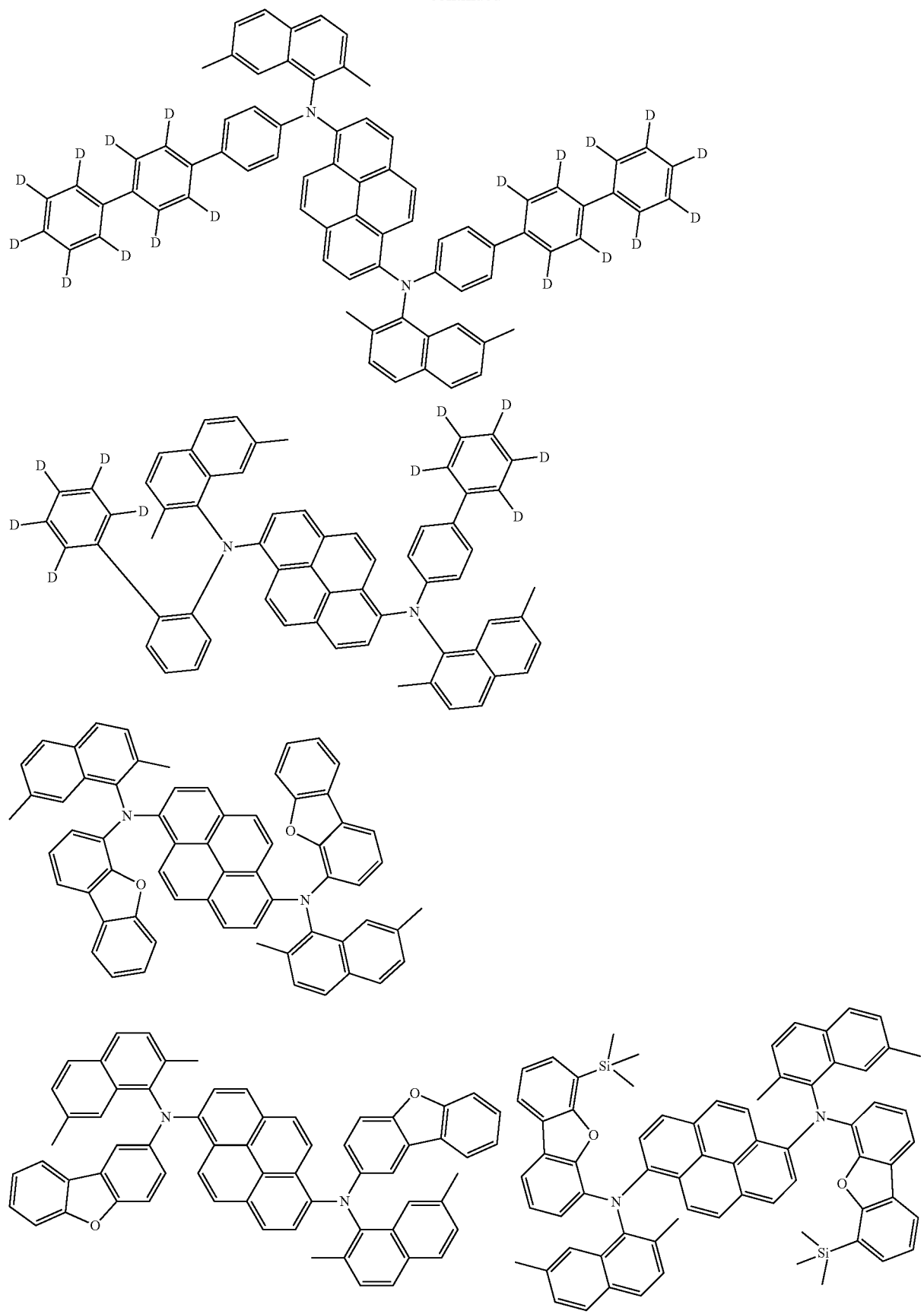

-continued
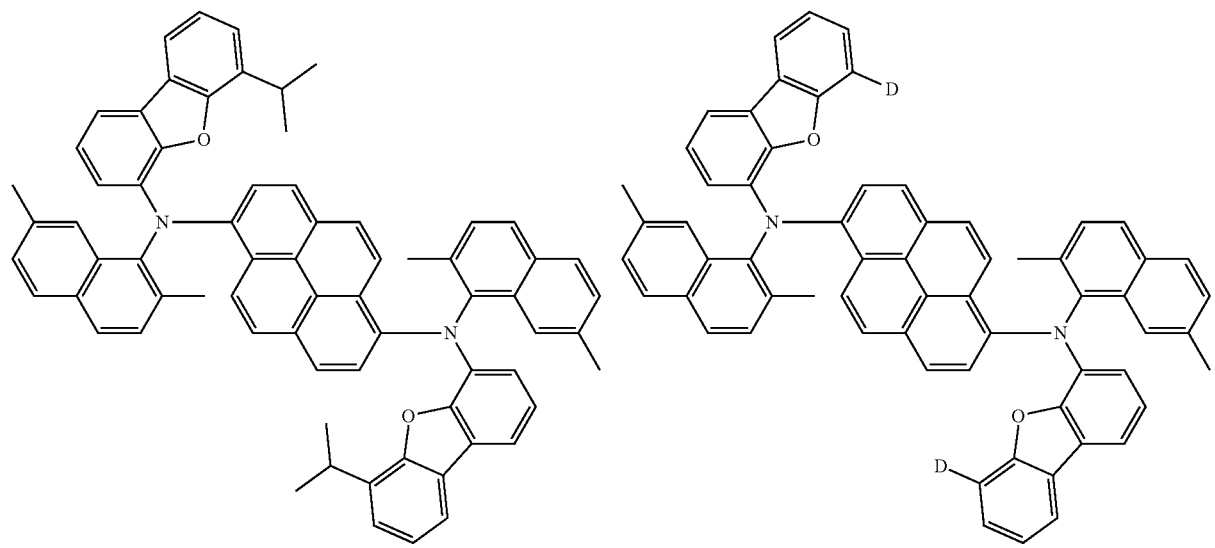
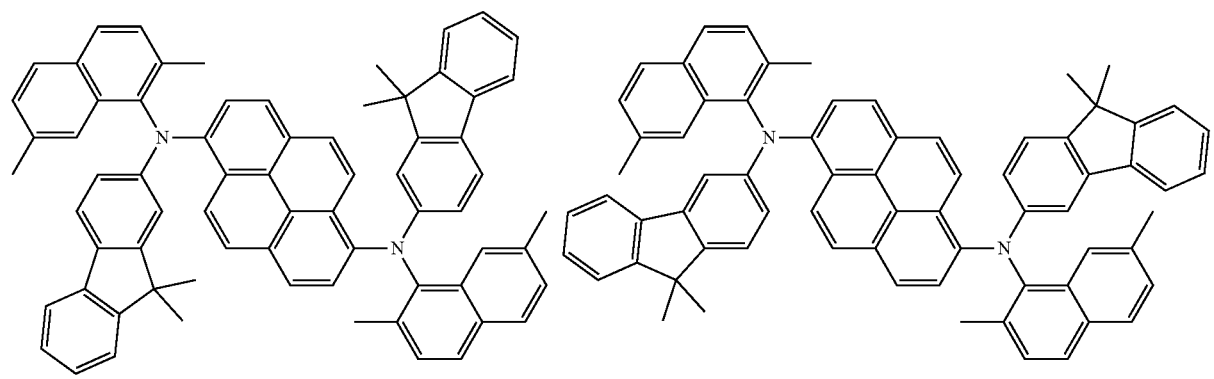
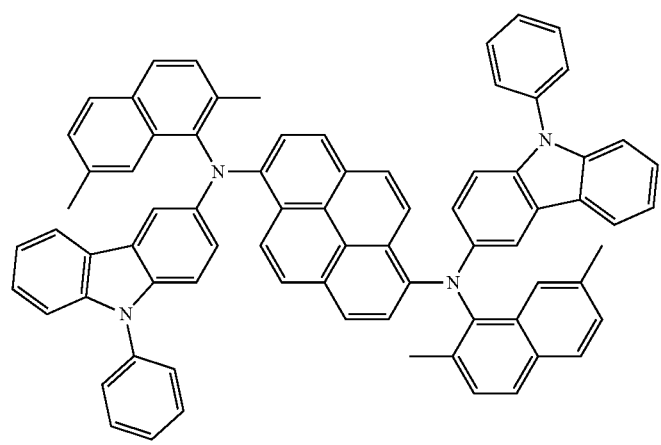

-continued
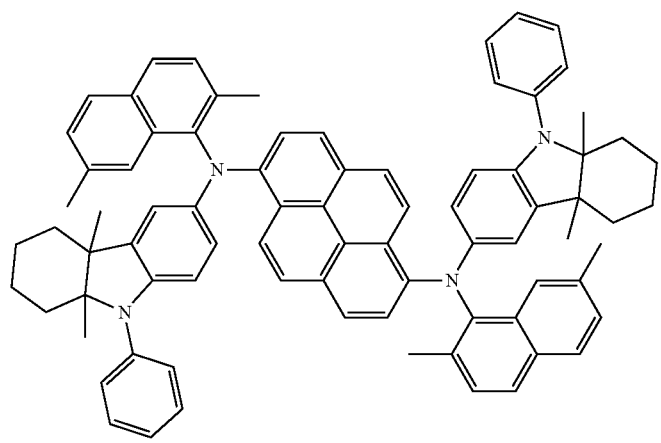
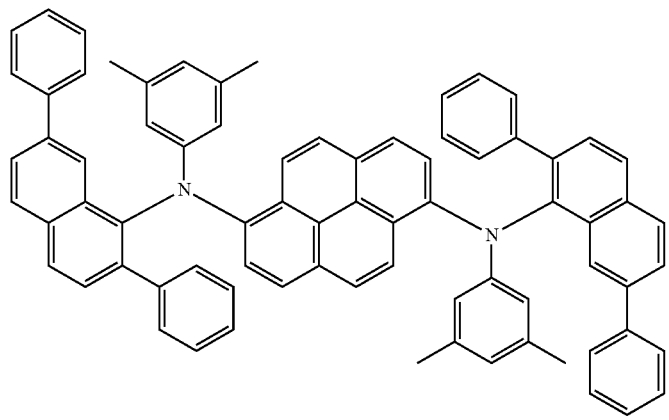
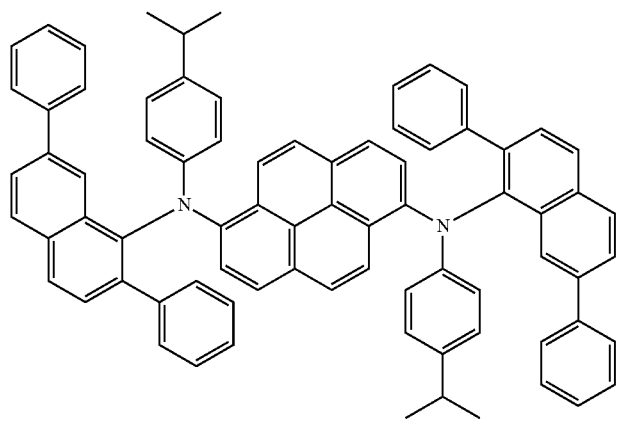
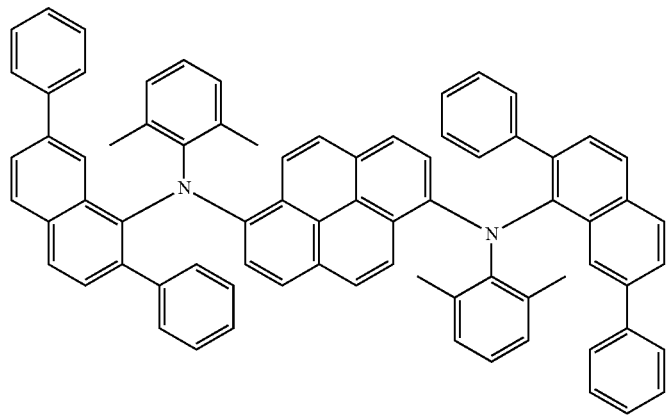

-continued
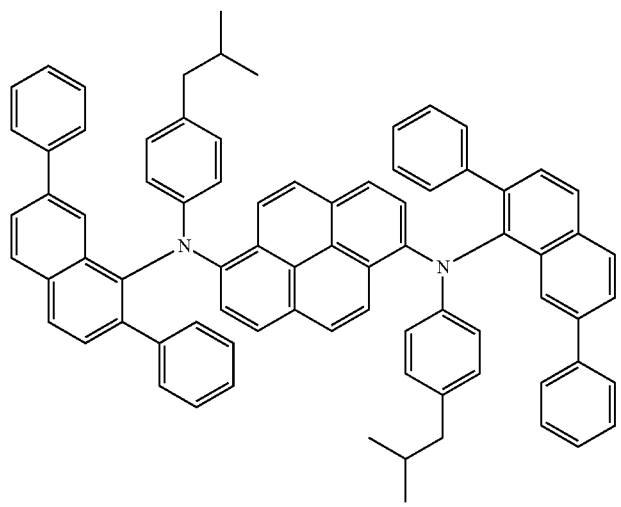
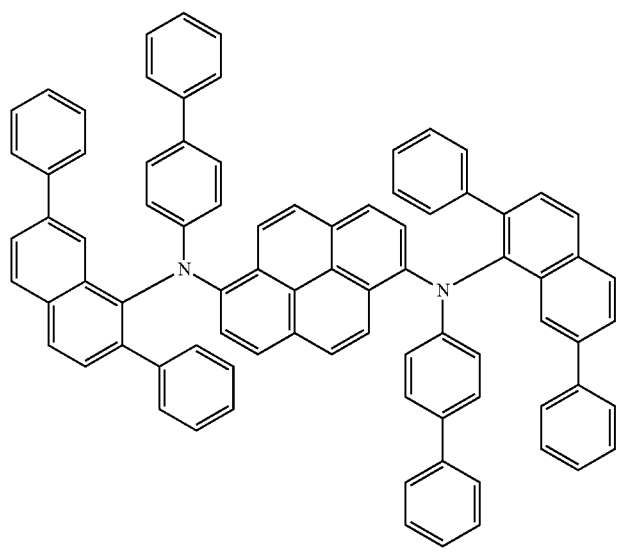
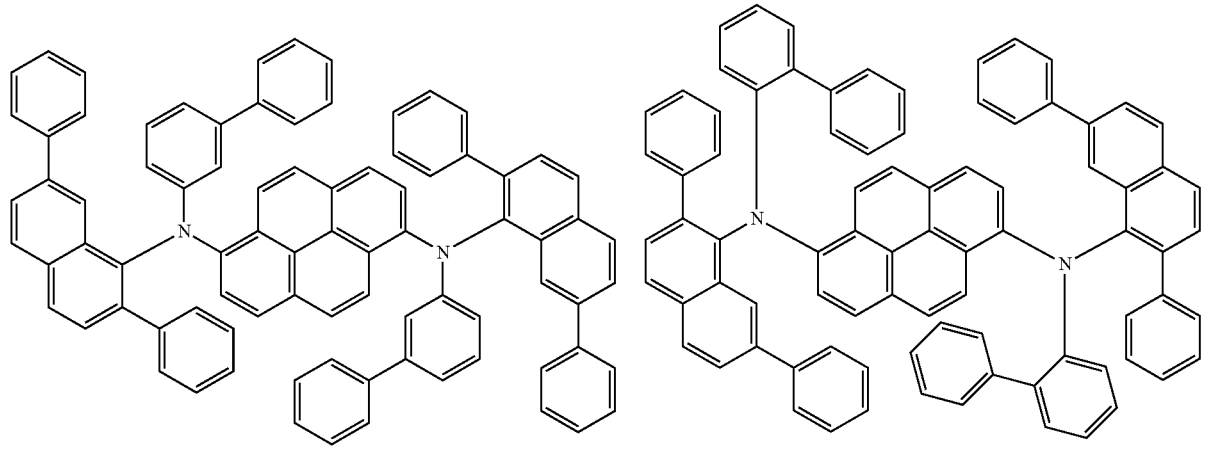

-continued
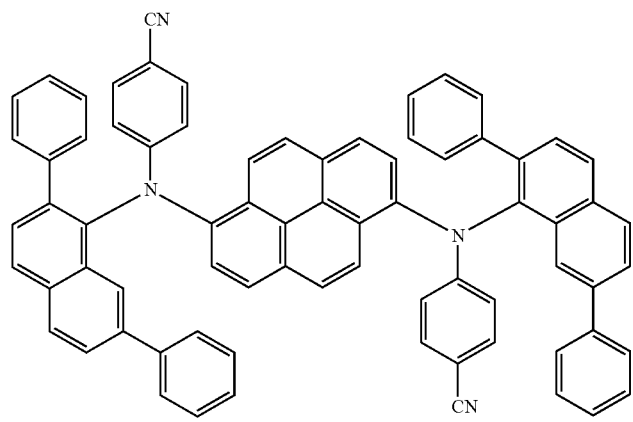
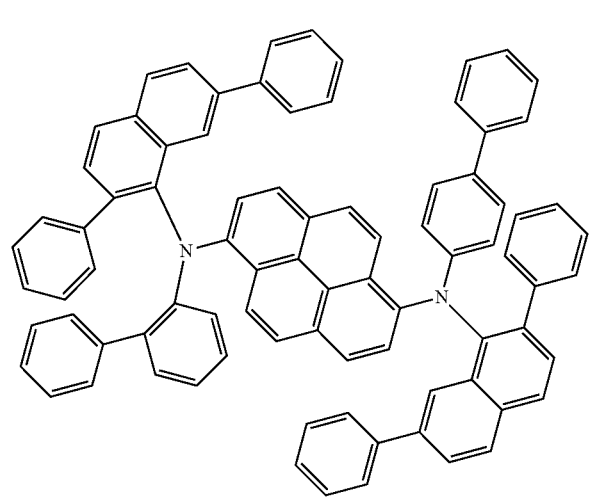
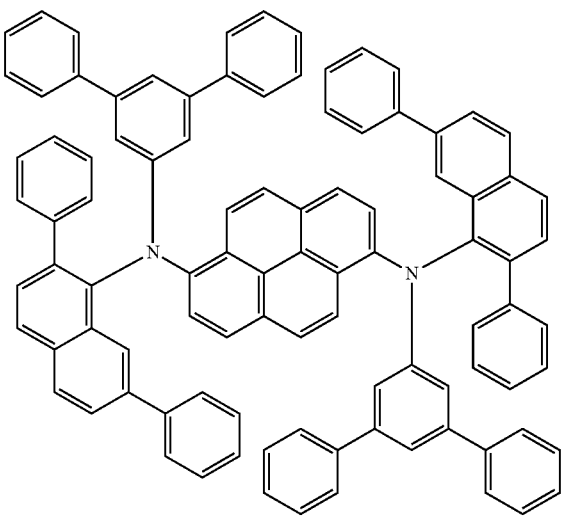
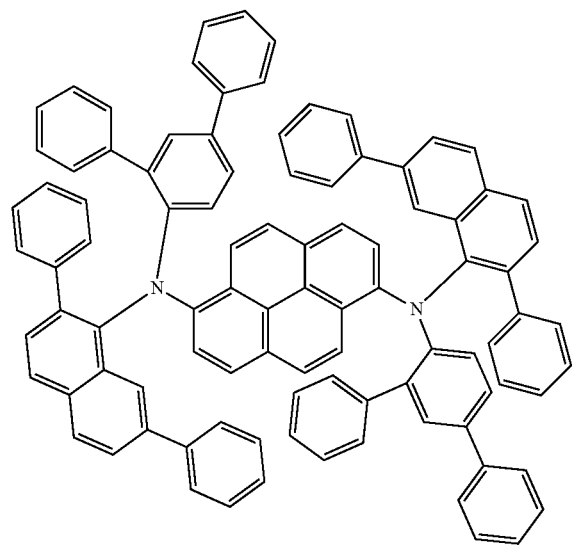

-continued
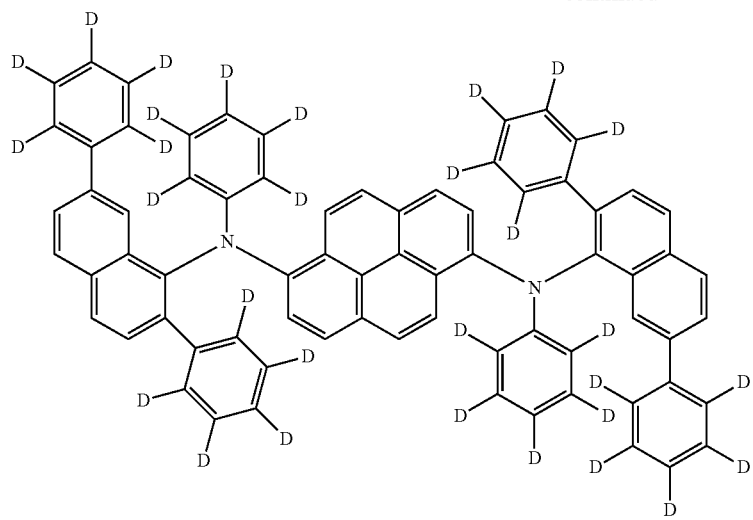
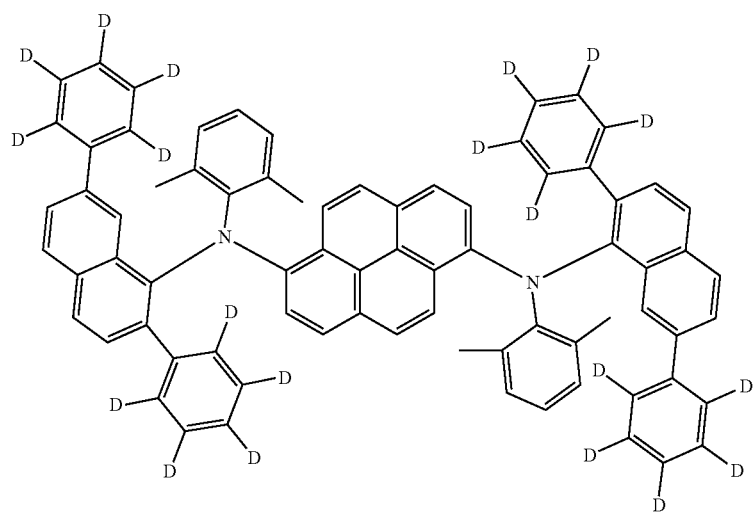
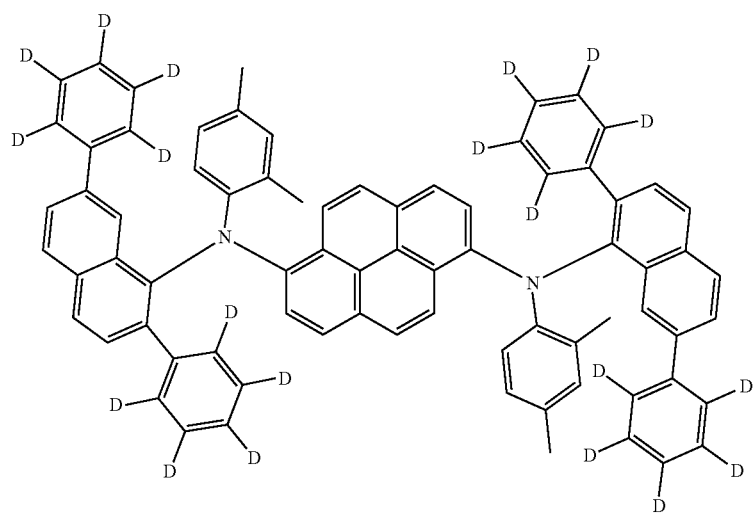

-continued
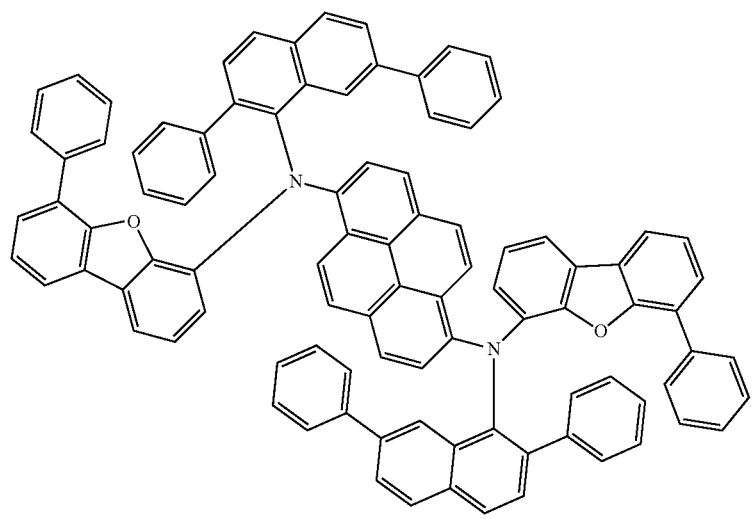
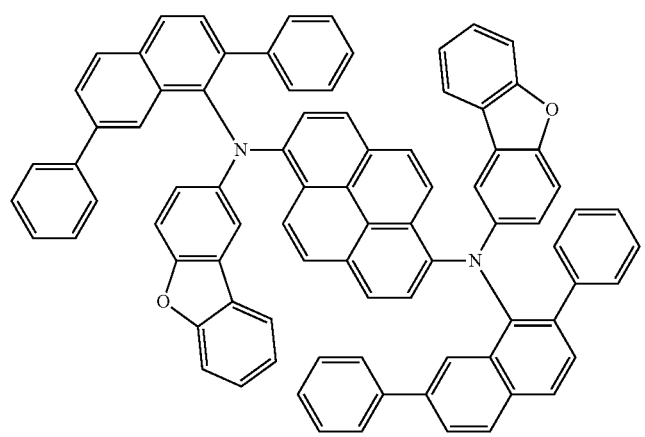
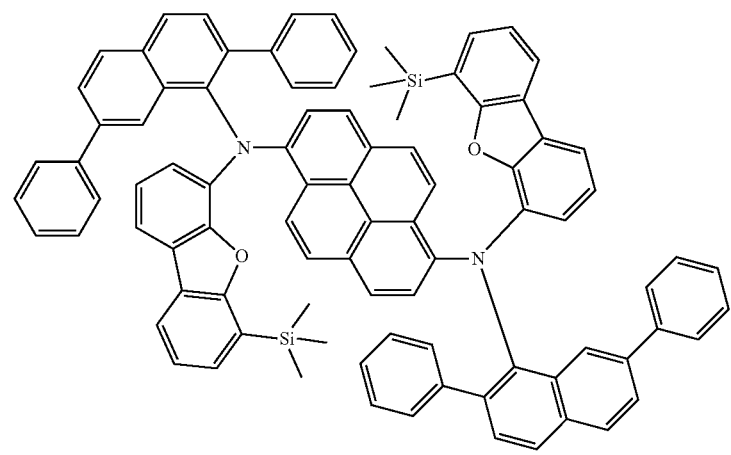

-continued
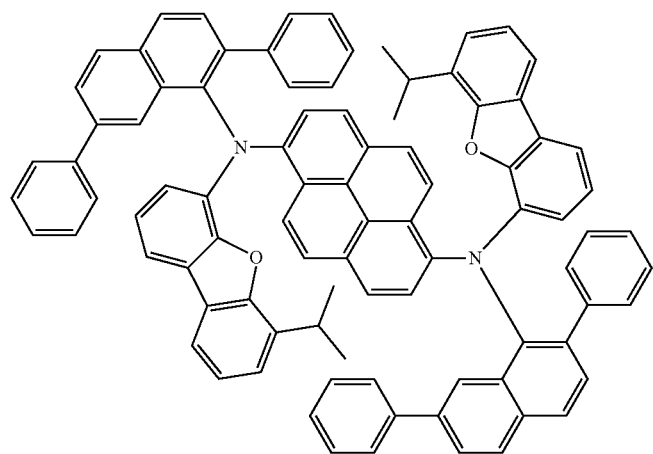
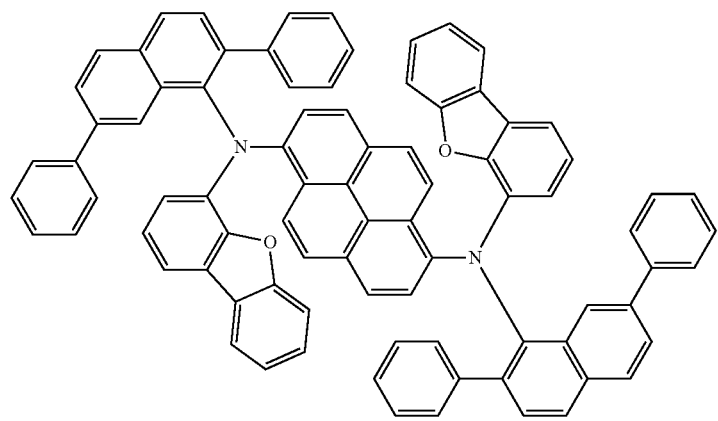
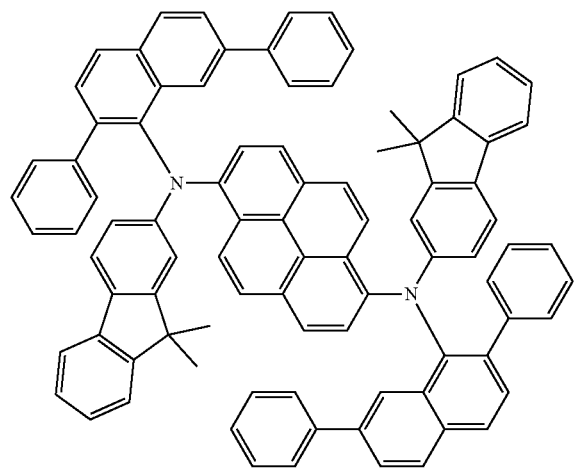

-continued
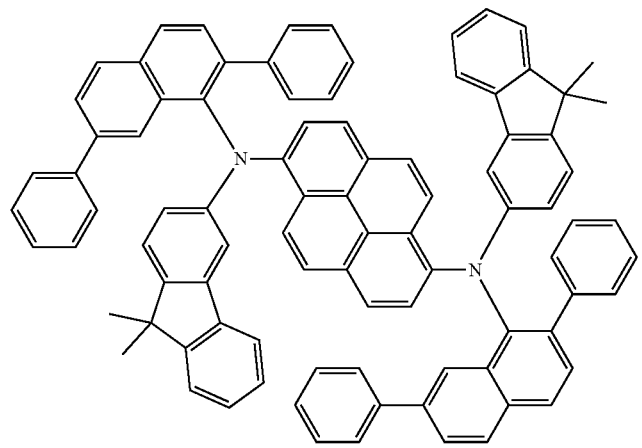
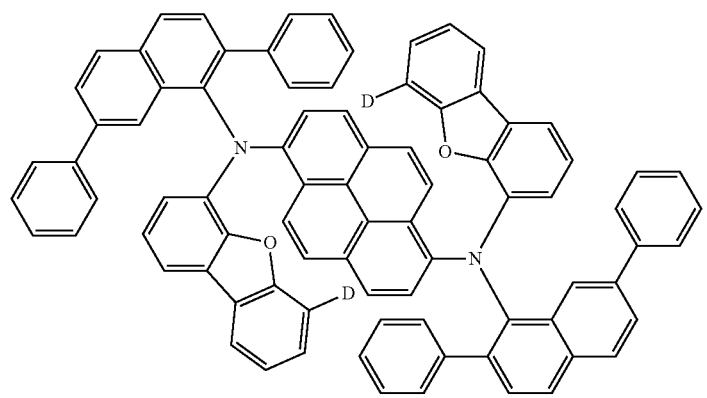
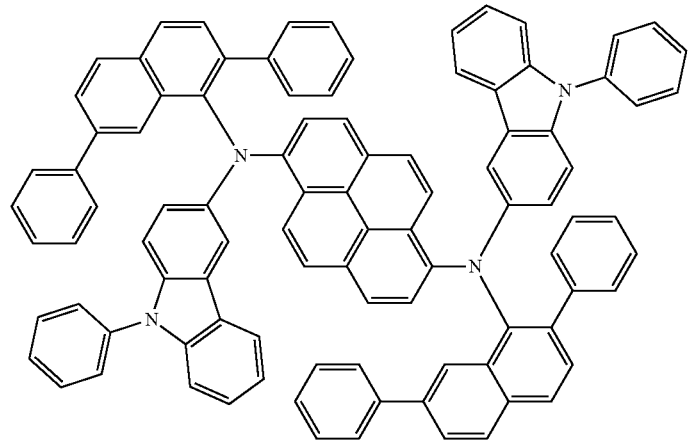
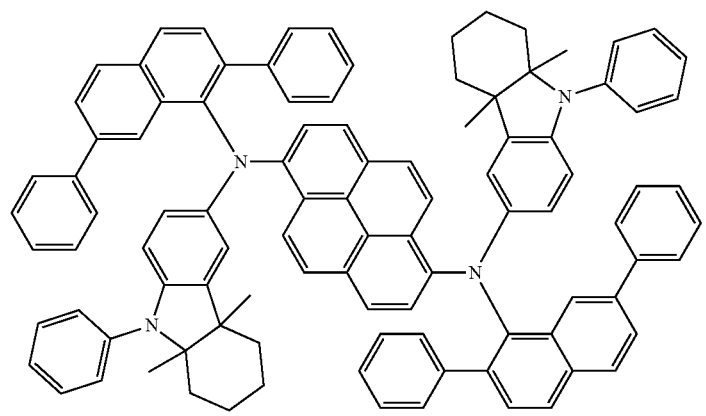

-continued
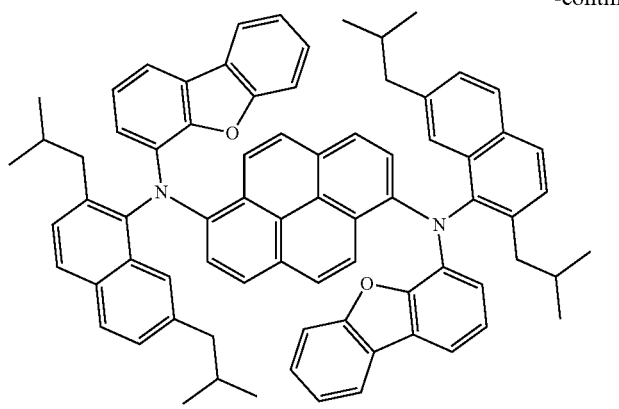
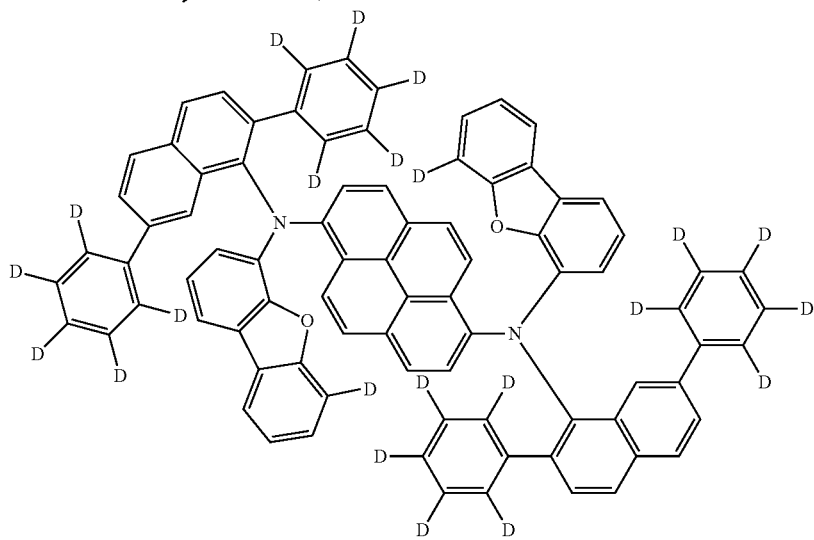
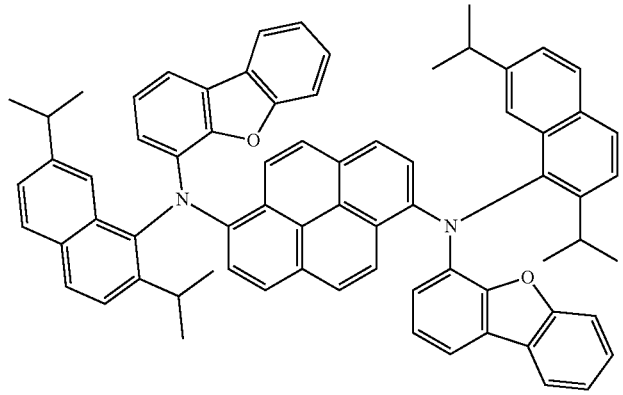
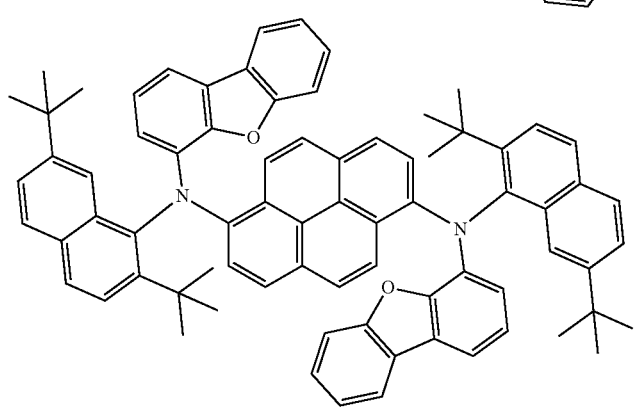

-continued
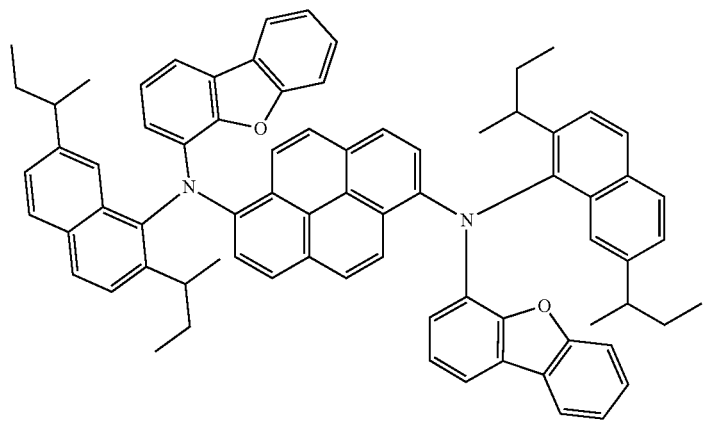
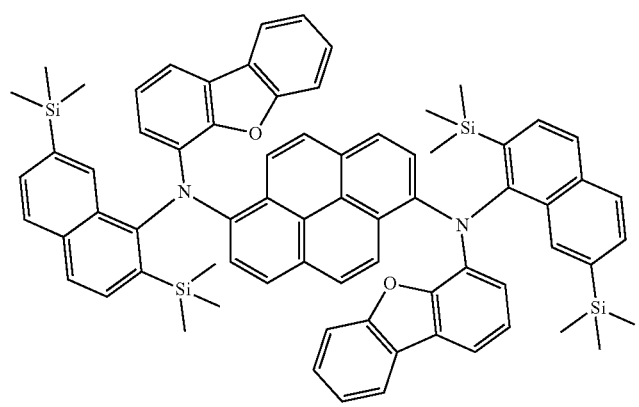
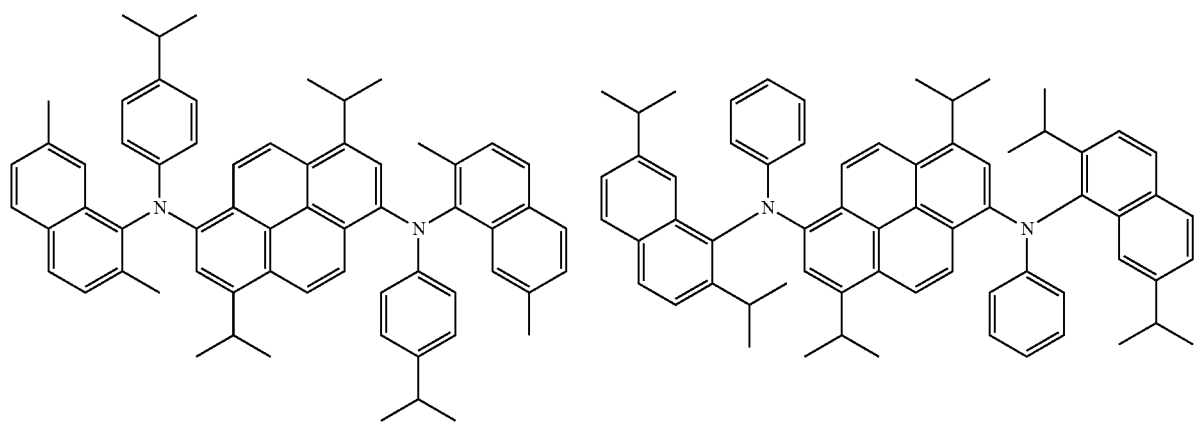
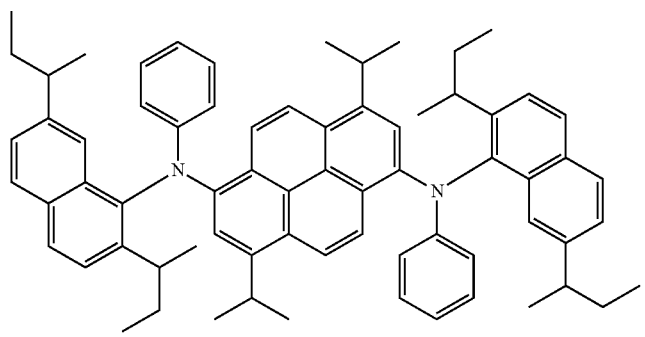

-continued
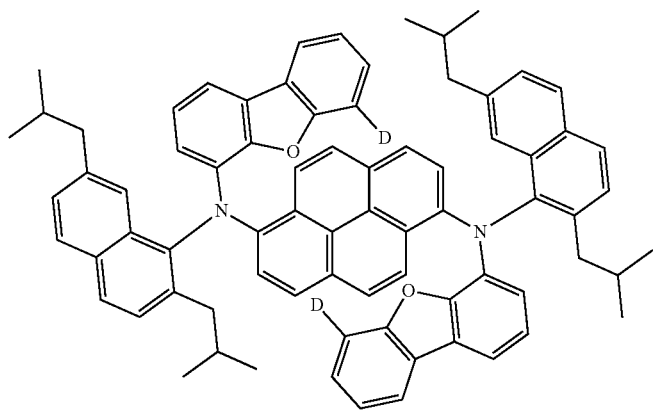
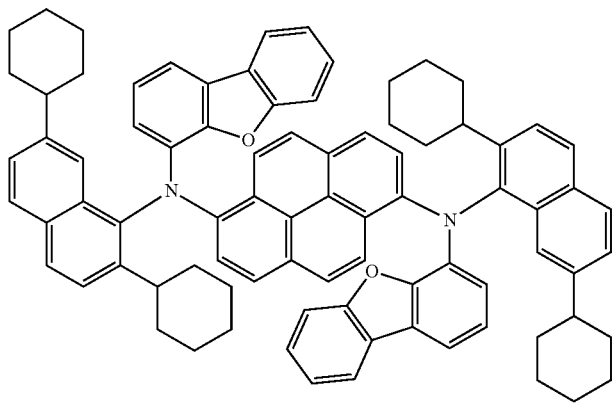
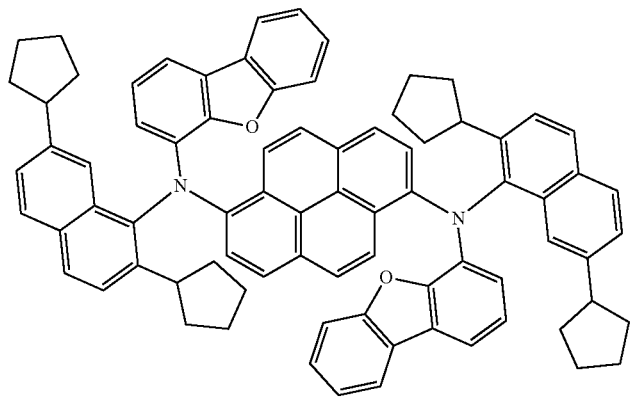
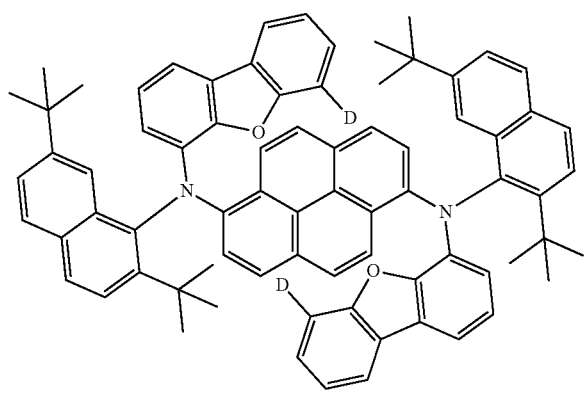

-continued
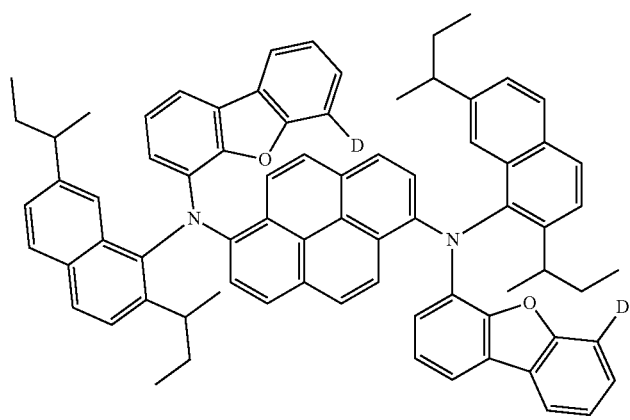
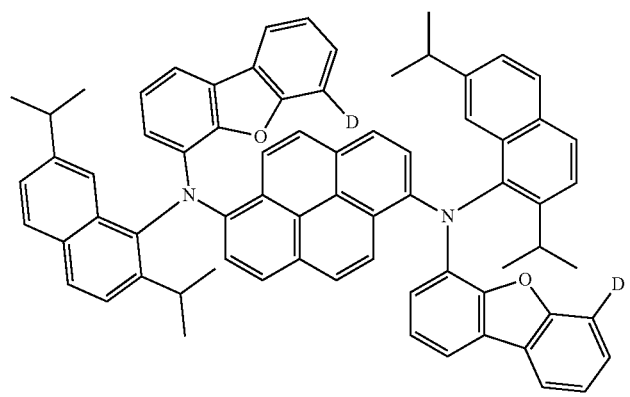
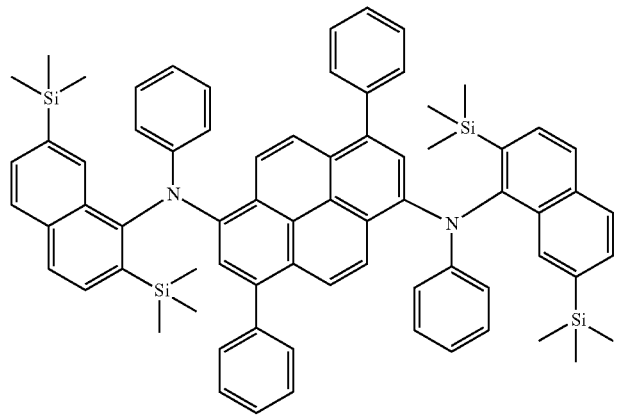
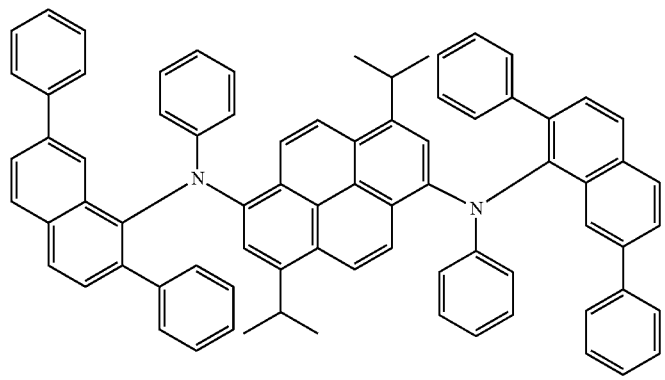

-continued
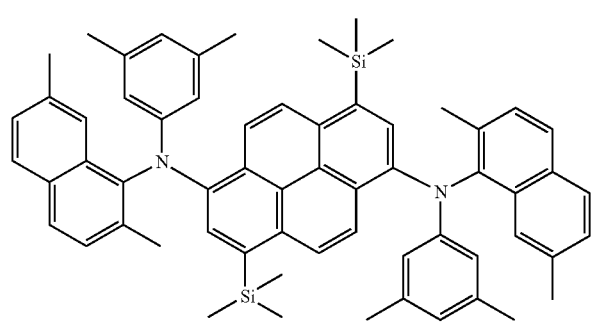
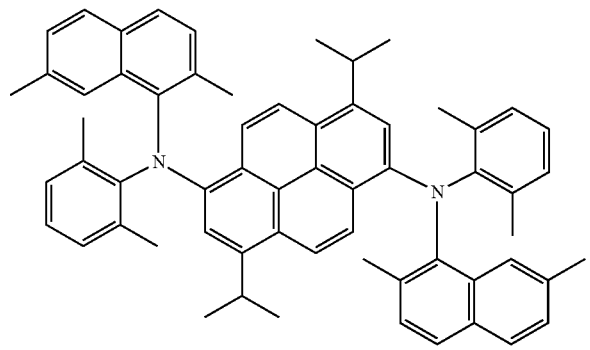
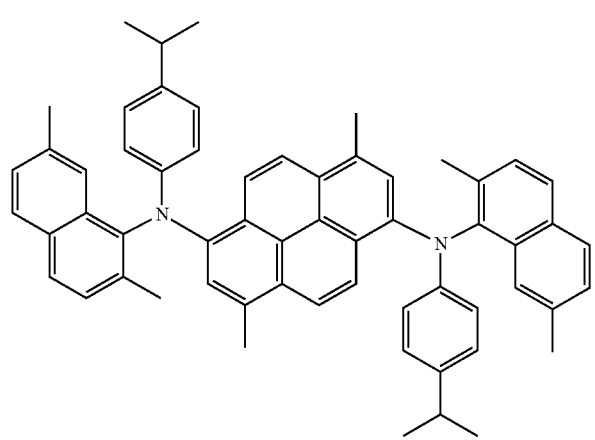
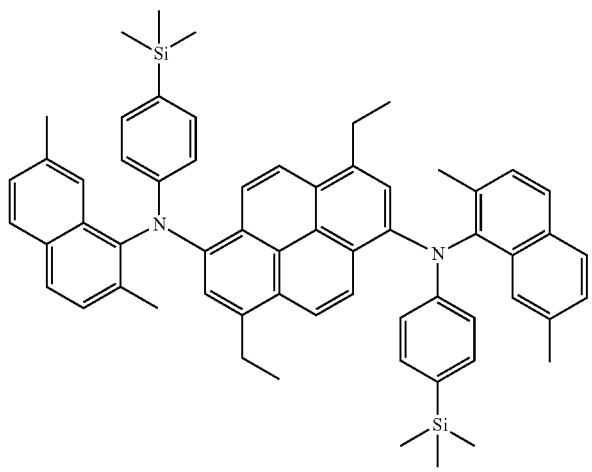
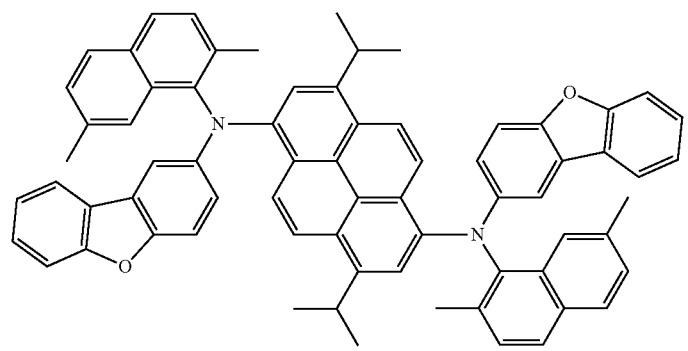
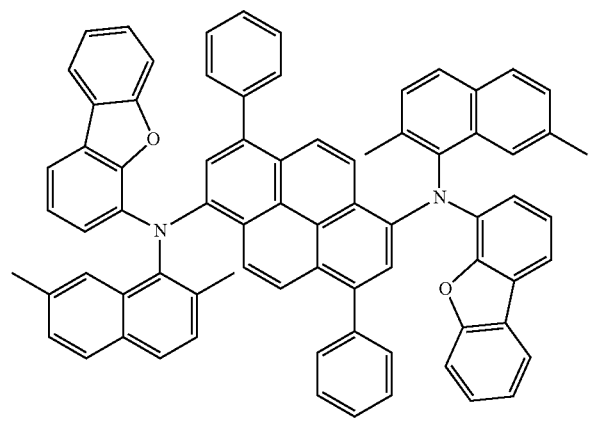
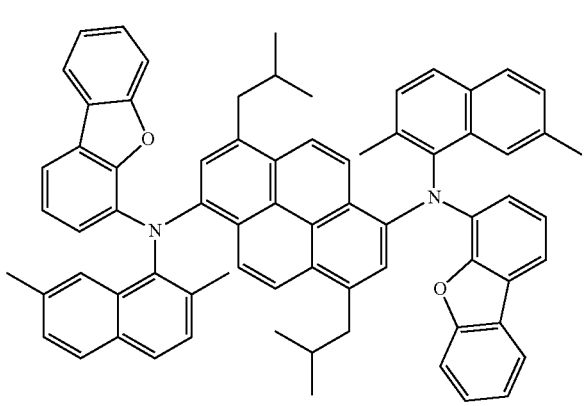

-continued
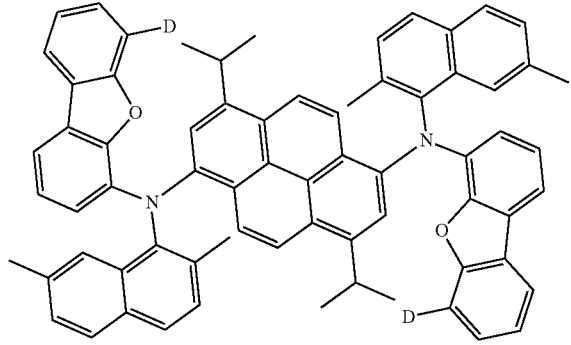
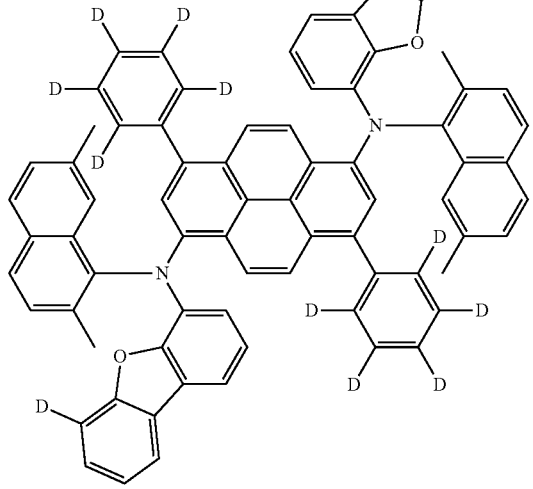
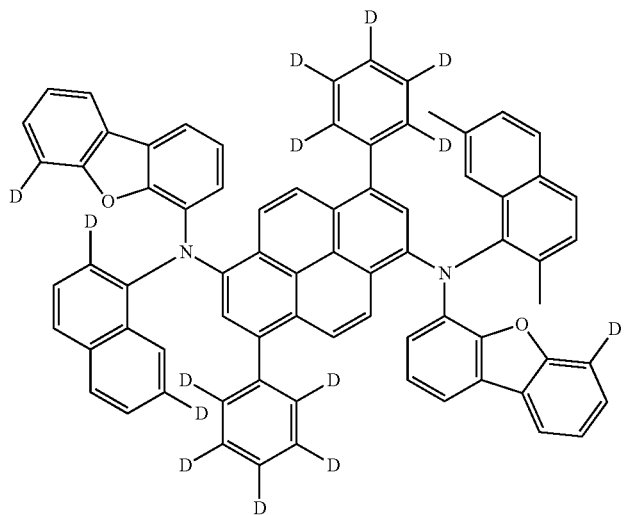
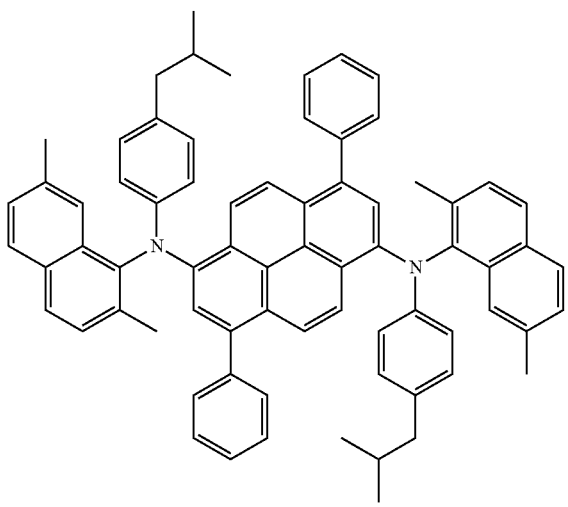
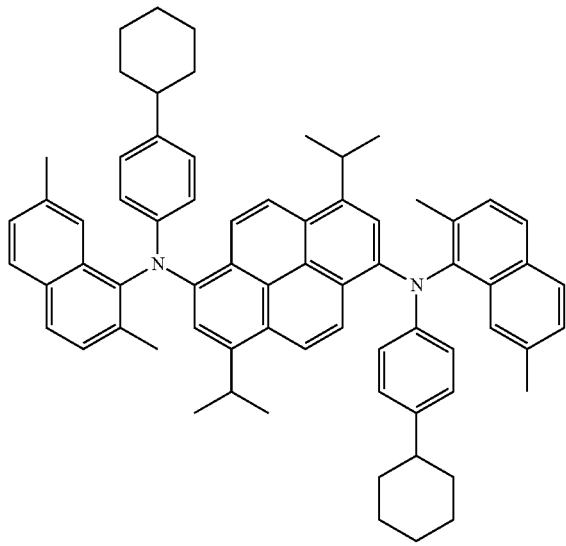
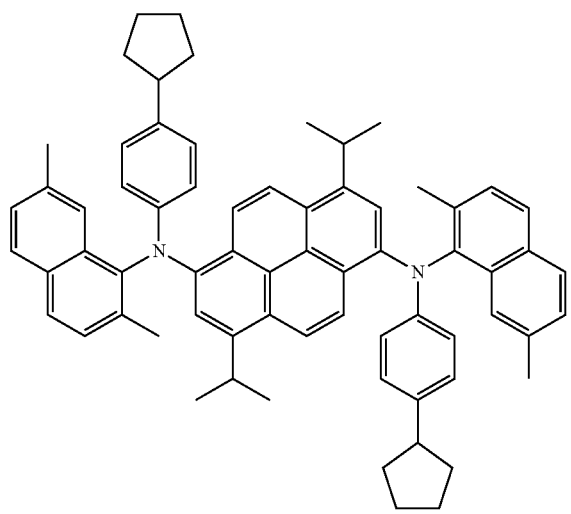

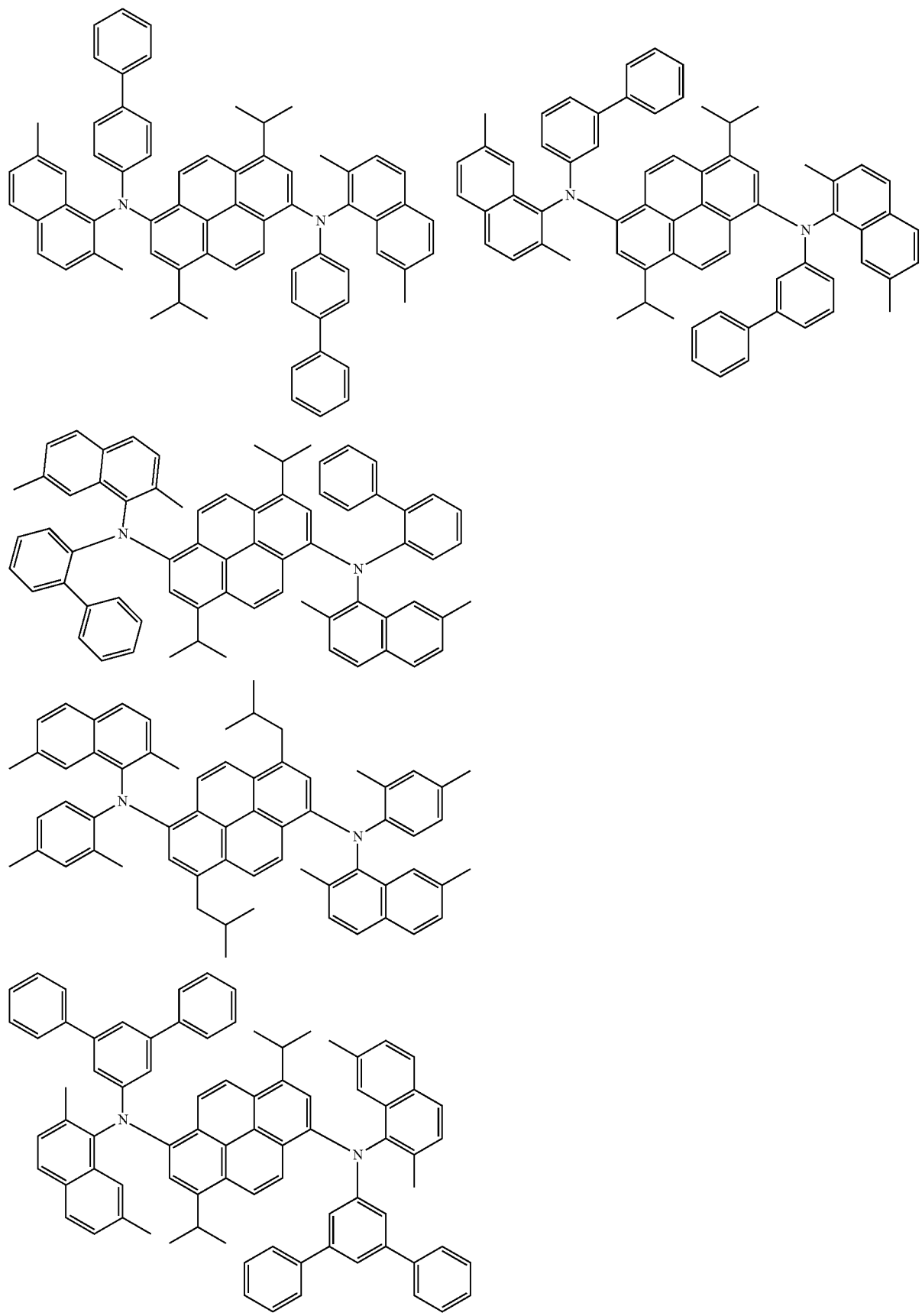

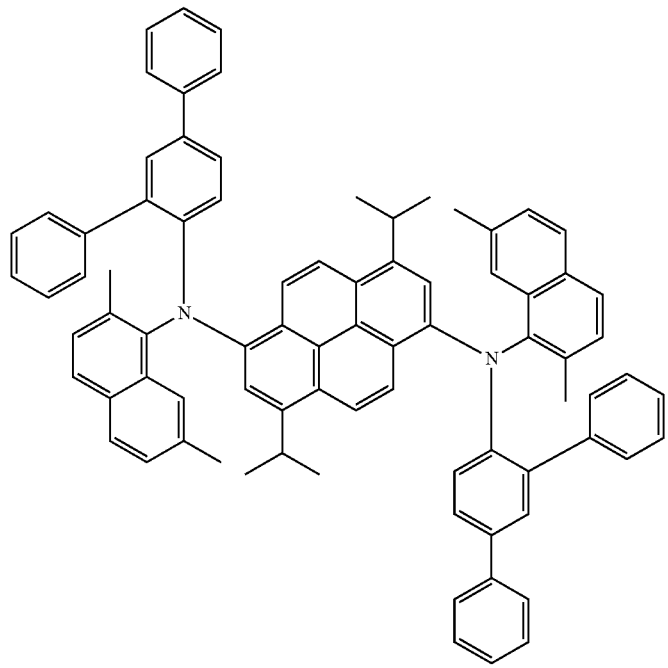
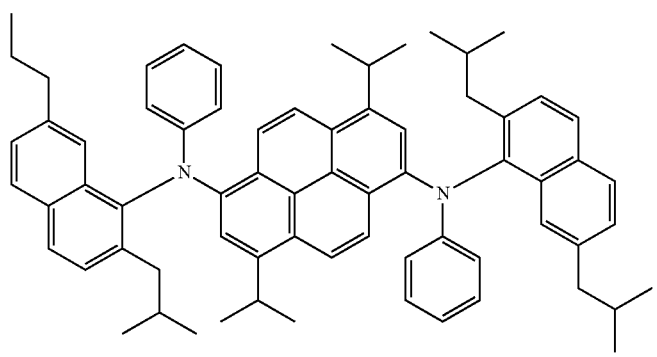
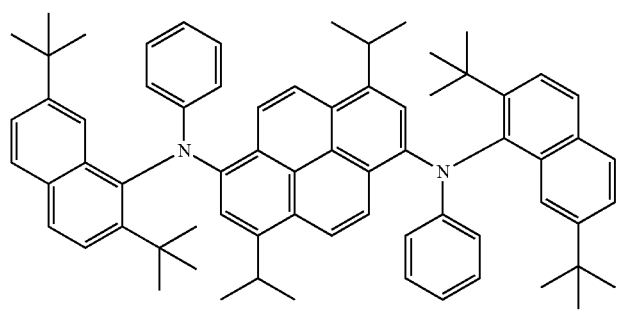
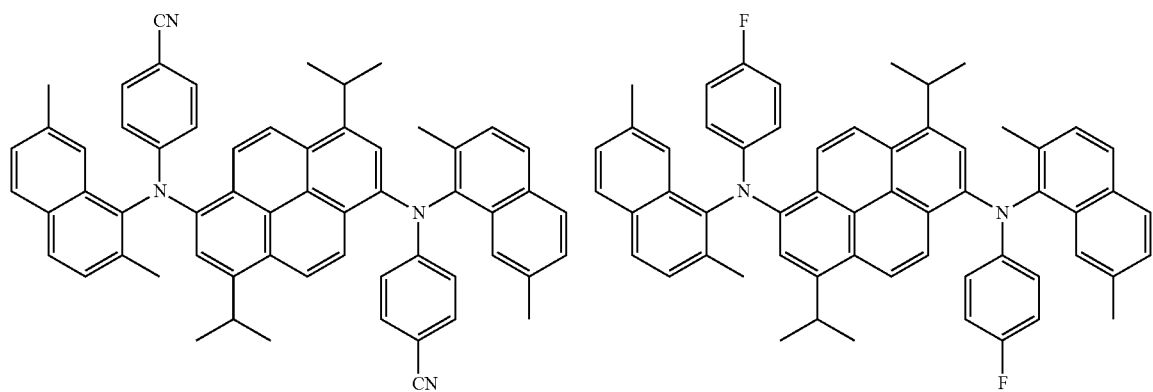

75 76
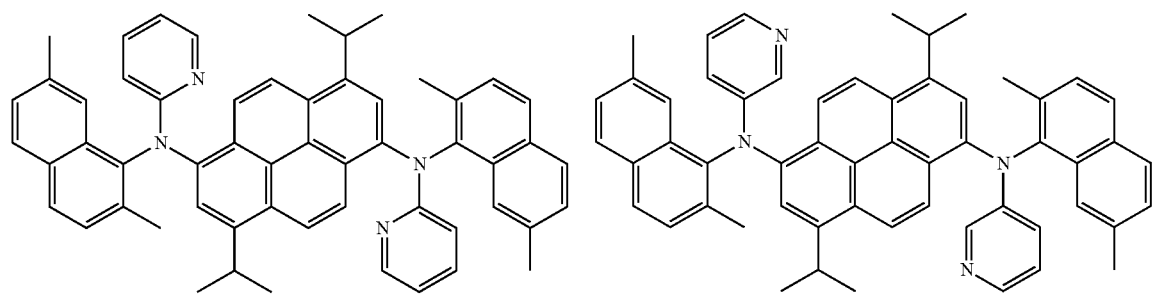
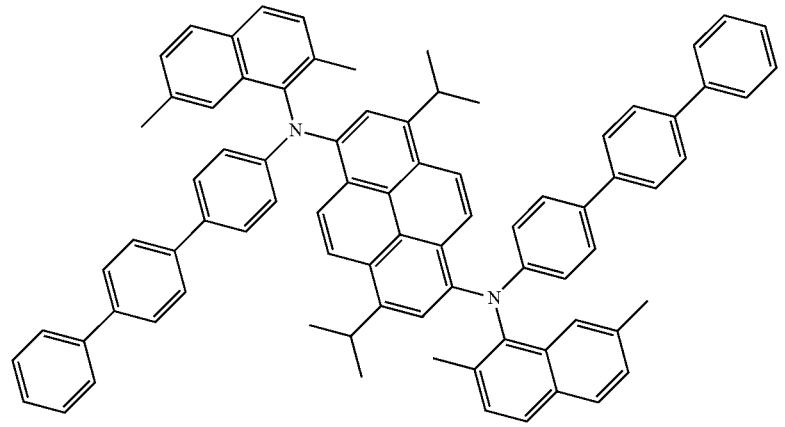
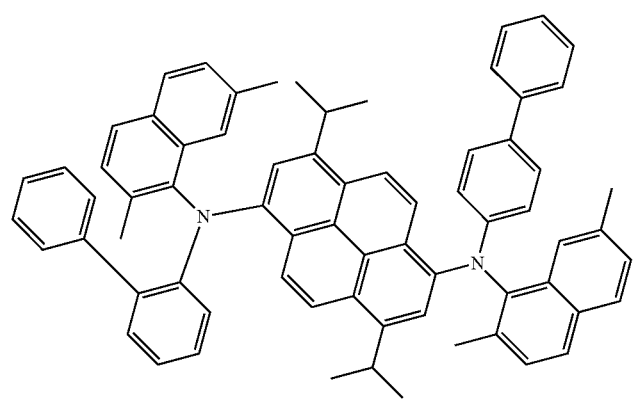
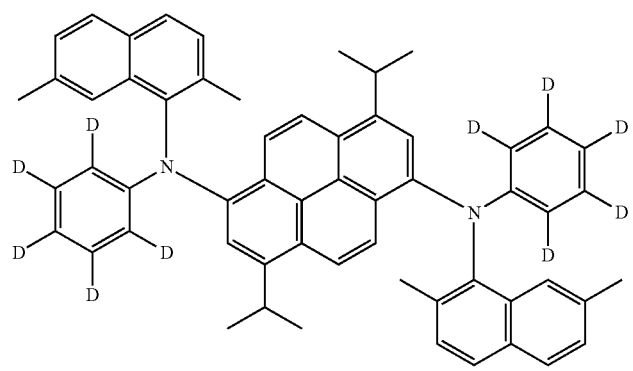

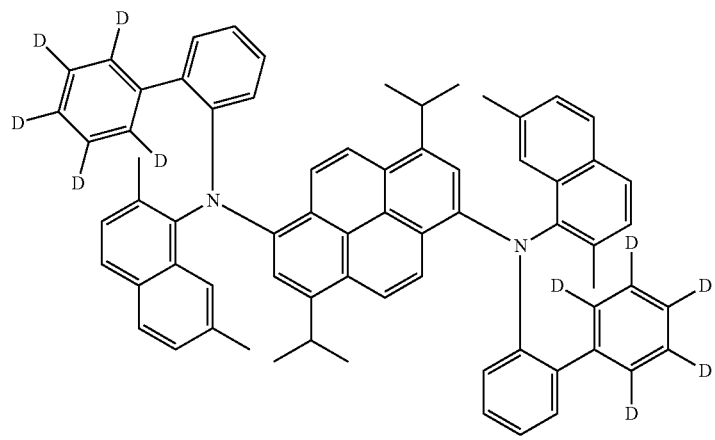
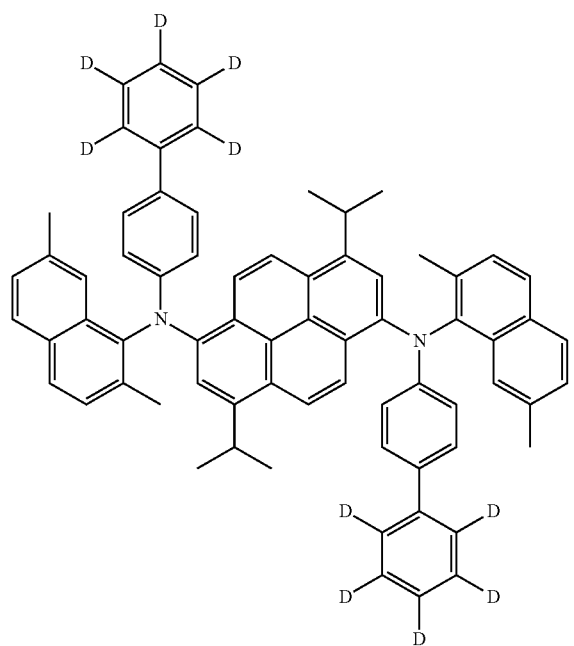
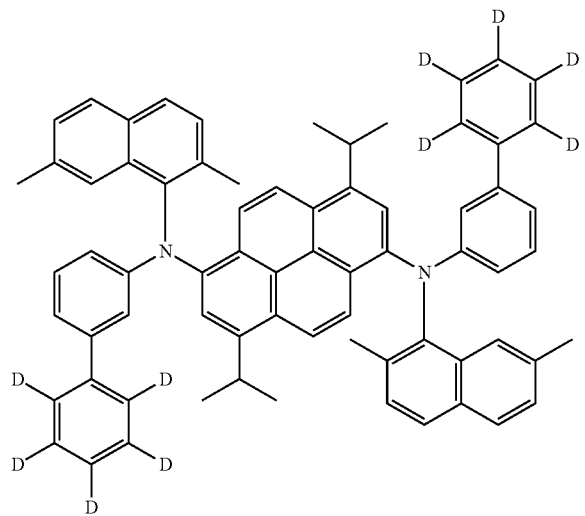

-continued
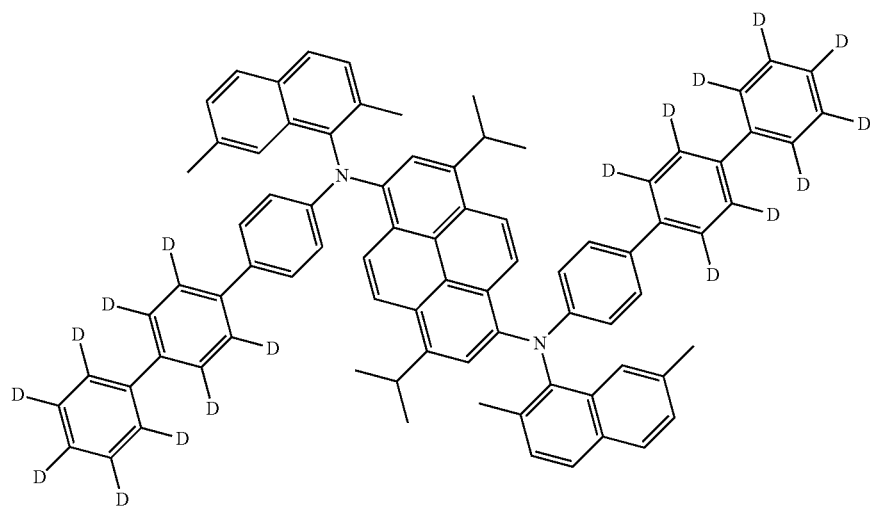
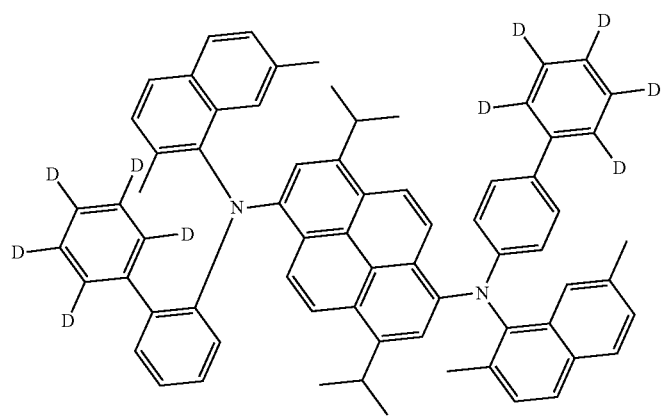
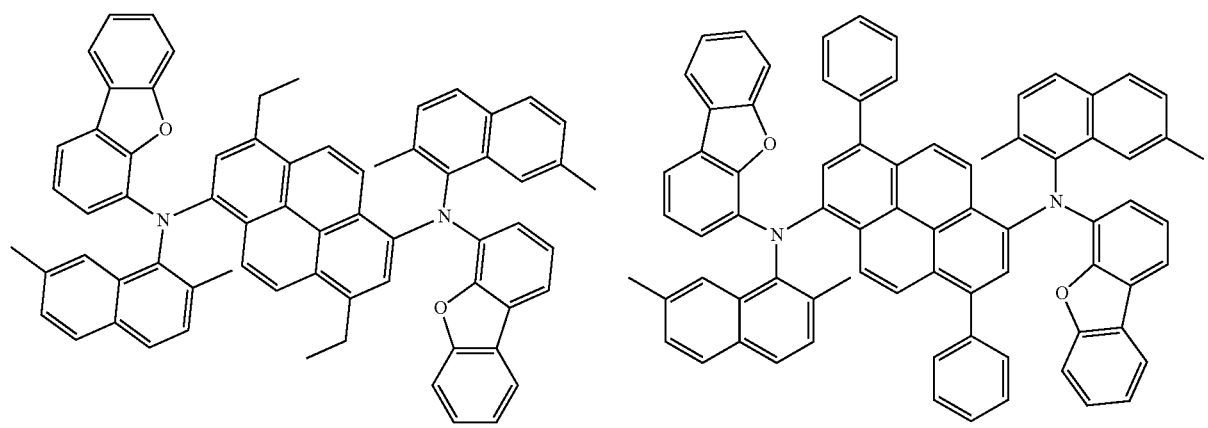

-continued
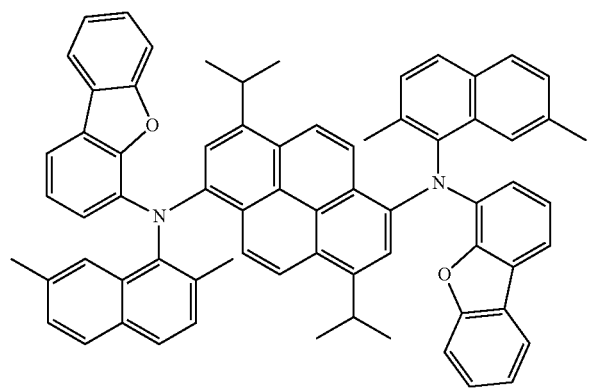
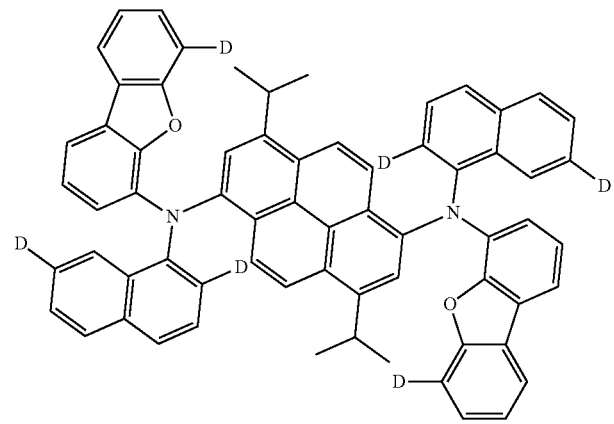
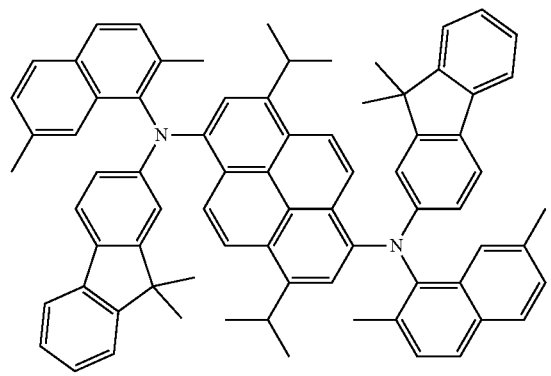
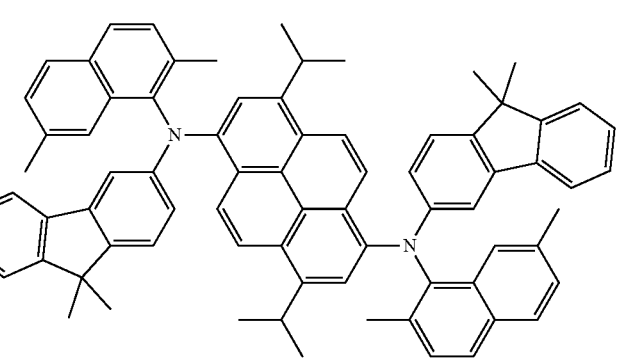
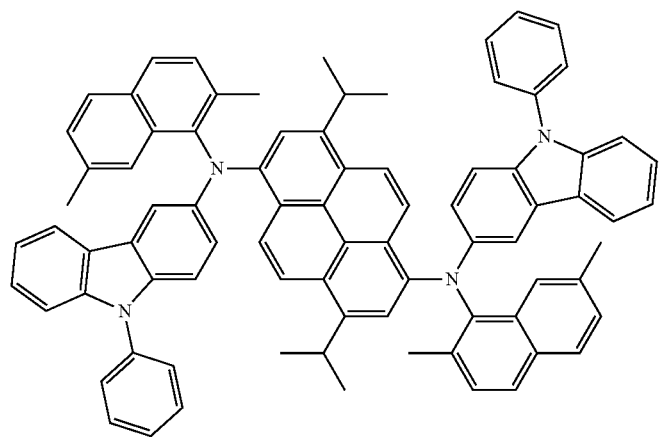
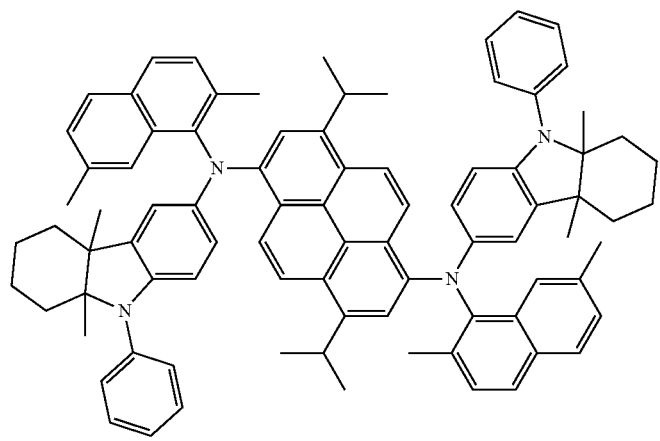

-continued
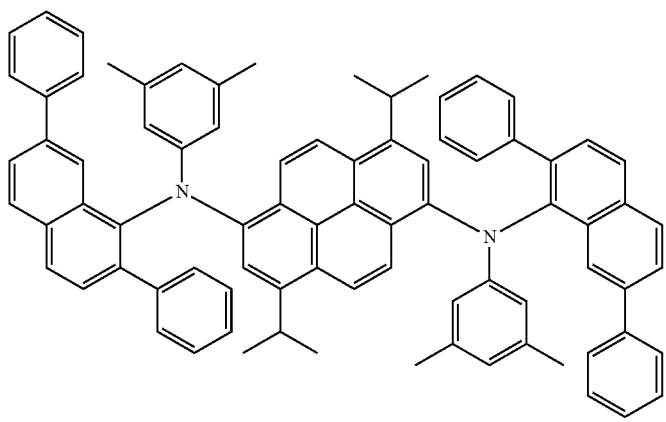
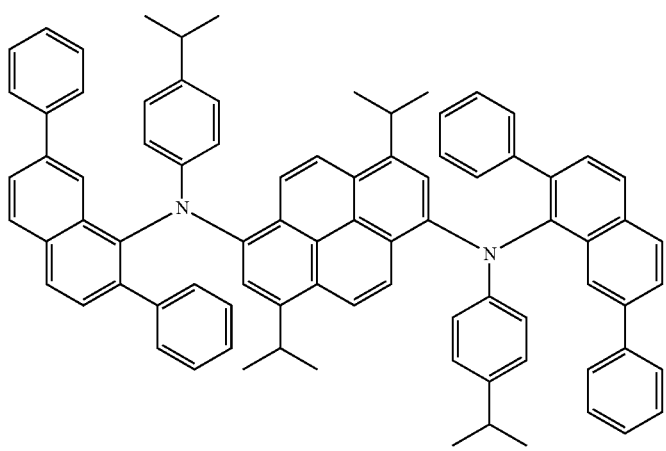
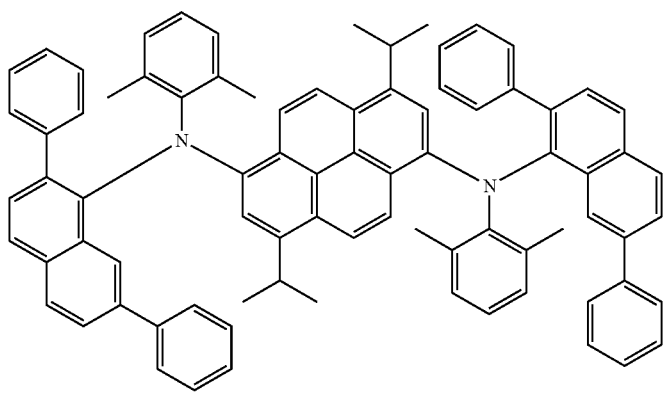

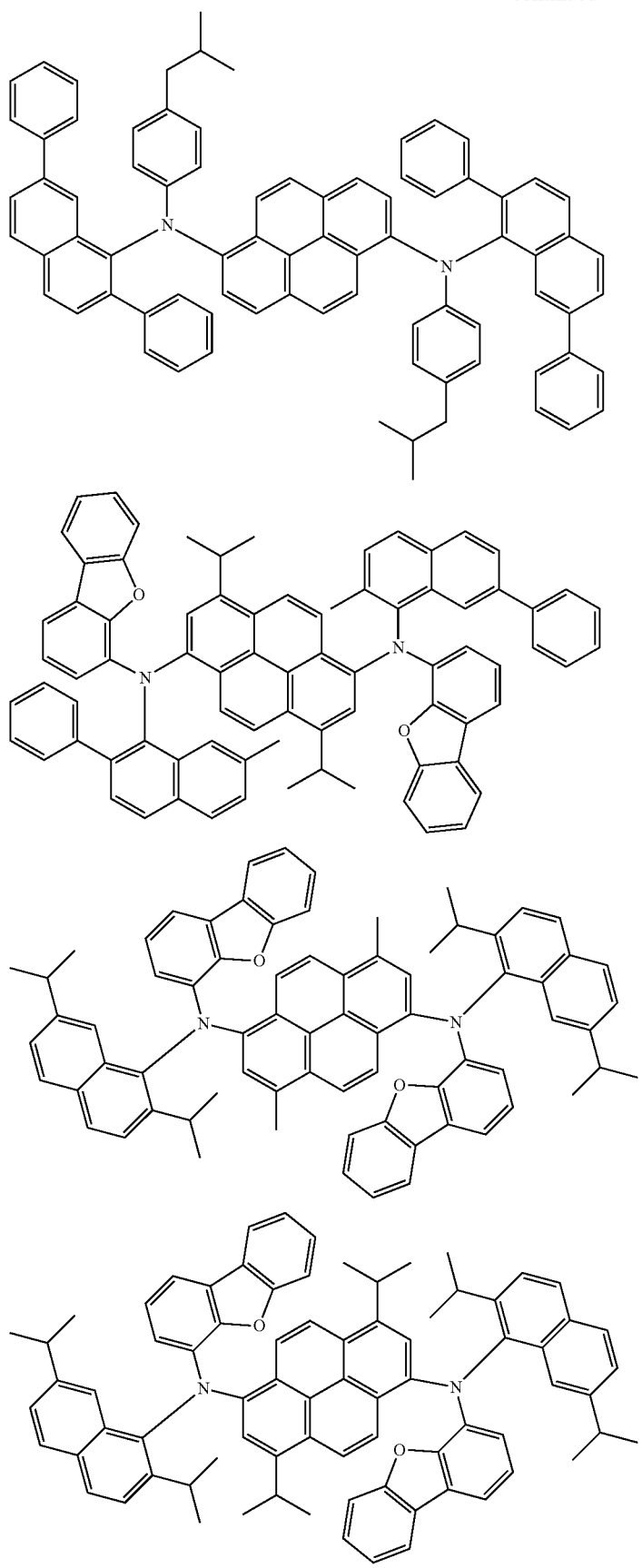

-continued
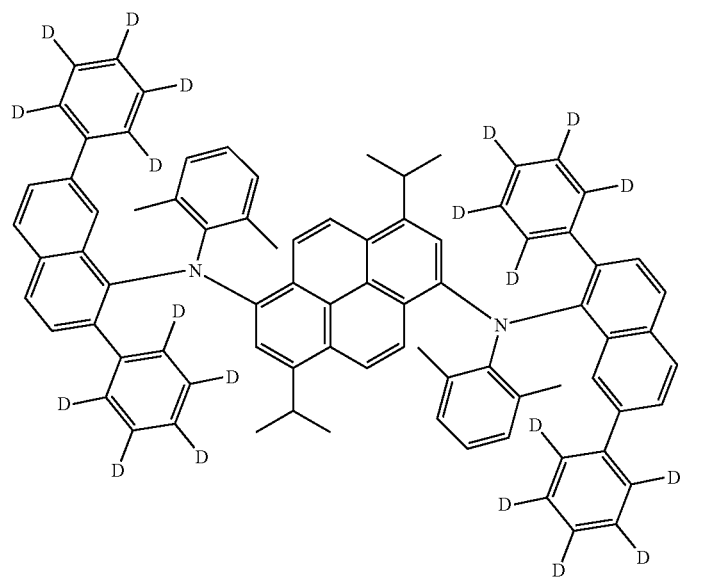
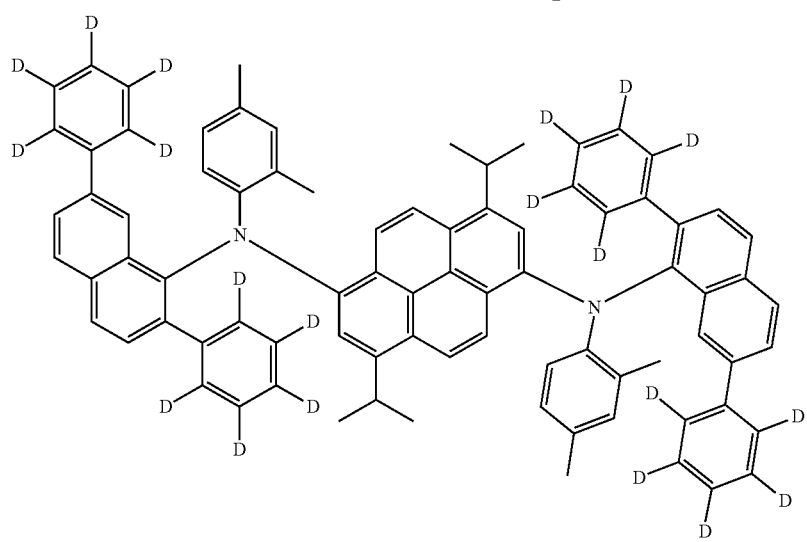
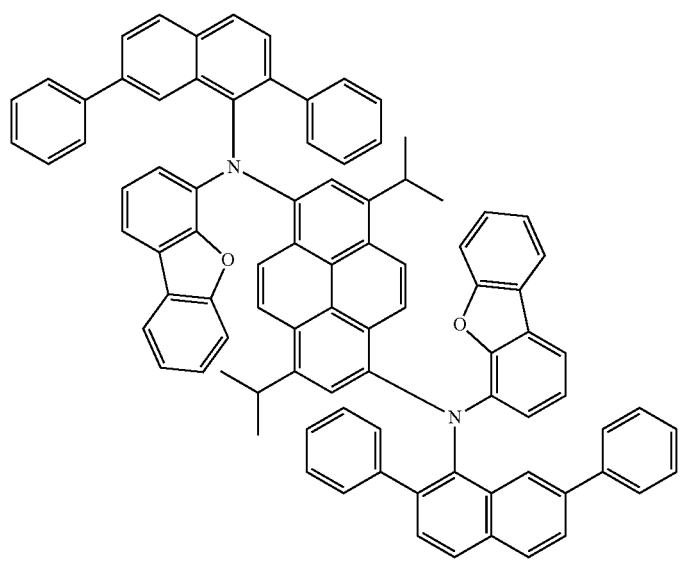

-continued
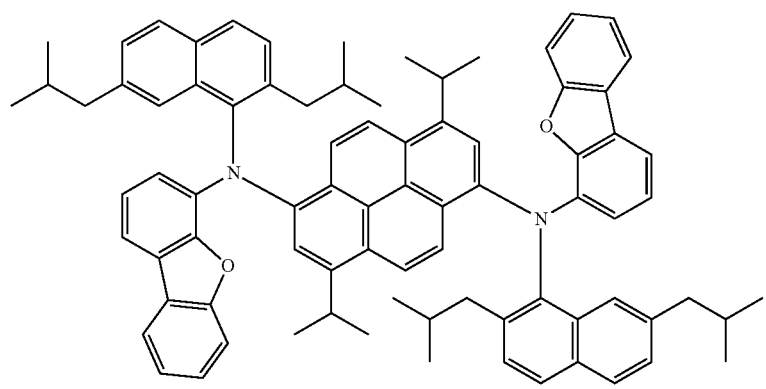
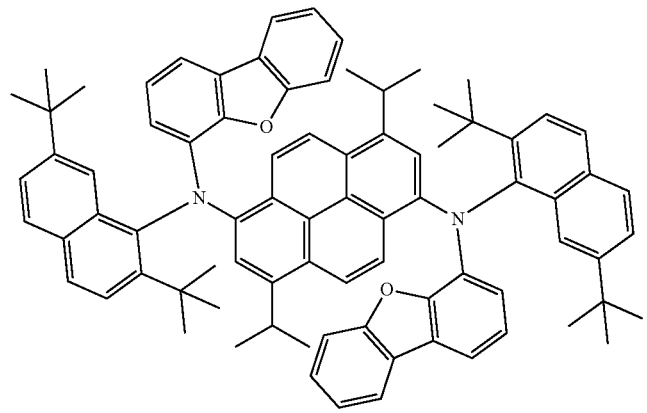
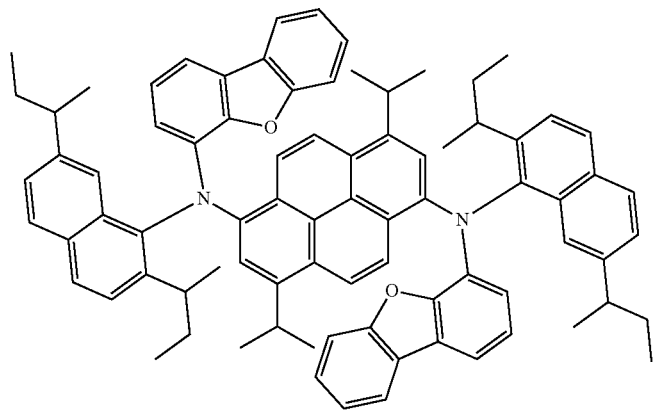
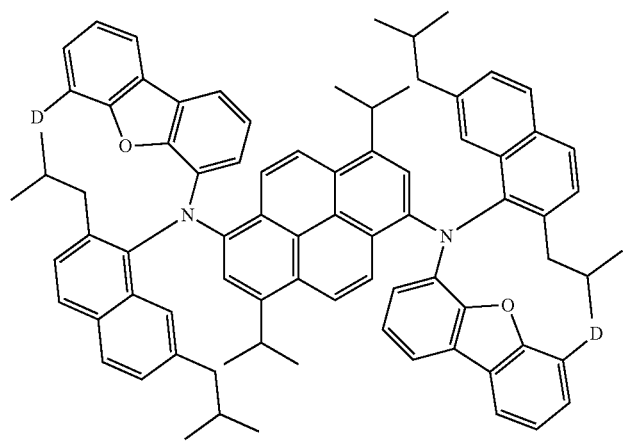

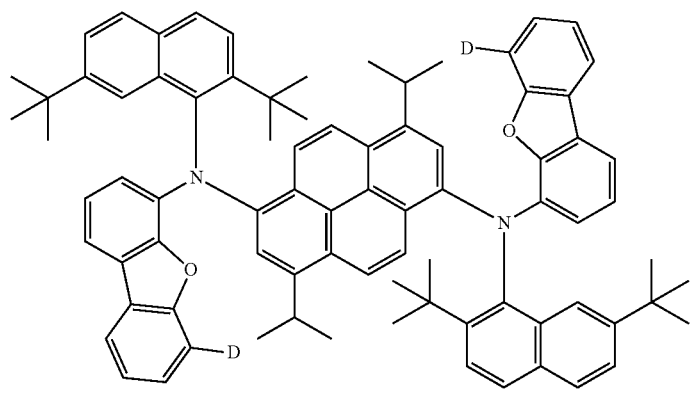
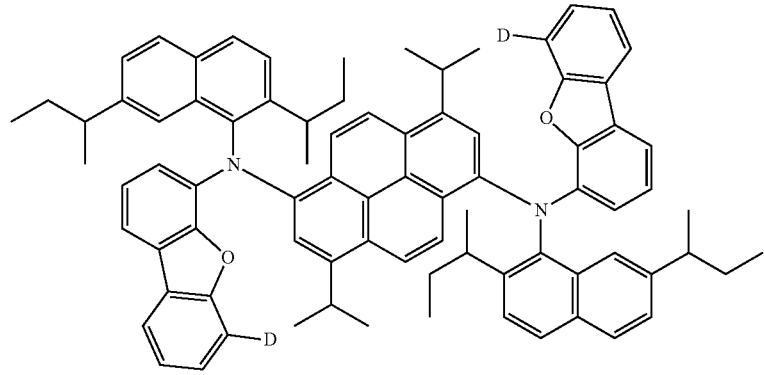
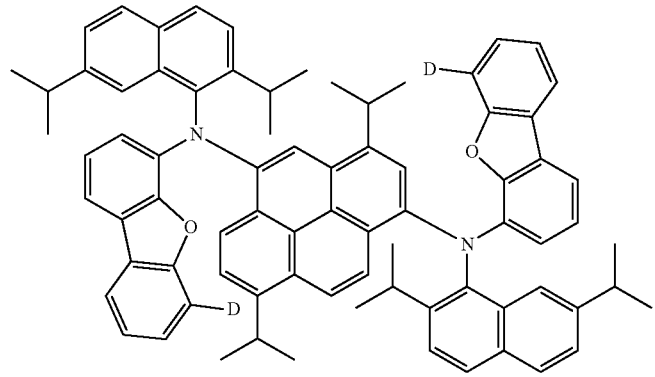
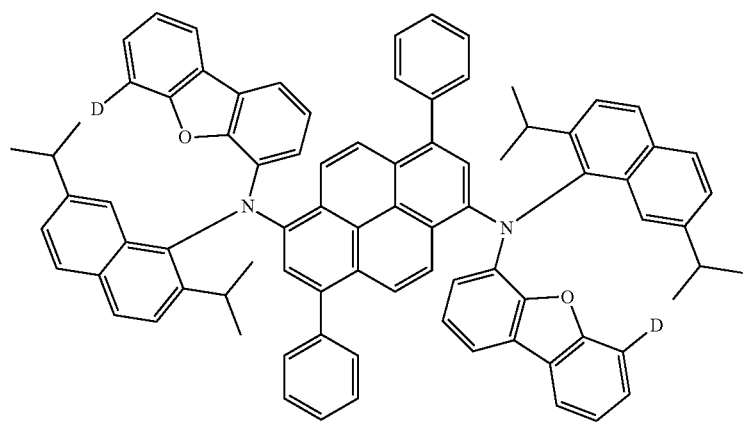

A method for synthesizing the aromatic amine derivative of general formula. (I)-(III), wherein the reaction is carried out using raw materials containing reactive groups. These active raw materials comprise at least one leaving group, for example, bromine, iodine, boric acid or borate ester. Appropriate reactions for forming C—C linkage are well known to those skilled in the art and described in literatures, the optional coupling reactions are the SUZUKI, SMILE and HECK coupling reactions.

A polymer, comprises at least one repeating unit selected from the above aromatic amine derivative. In one embodiment, the polymer is a non-conjugated polymer, wherein the aromatic amine derivative is linked on the side chain. In embodiments, the polymer is a conjugated polymer.

A formulation comprises the above aromatic amine derivative or the above polymer, and at least one organic solvent.

A mixture comprises the above aromatic amine derivative or the above polymer, and at least one organic functional material, the organic functional material may be selected from the group consisting of: the hole (also called electron hole) injection or transport material (HIM/HTM), the hole blocking material (HBM), the electron injection or transport material (EIM/ETM), the electron blocking material (EMI), the organic matrix material (Host), the singlet emitter (fluorescent emitter), the triplet emitter (phosphorescent emitter), the thermally activated delayed fluorescent material (TADF material) and the organic dye. Various organic functional materials are described in detail, for example, in WO2010135519A1, US20090134784A1 and WO 2011110277A1, and the entire contents of these three patent documents are hereby incorporated herein by reference.

In one embodiment, the mixture comprises the above aromatic amine derivative or the above polymer, and a fluorescent host material (or singlet emitter). The above aromatic amine derivative or the above polymer may be used as a guest, and the weight percentage of the above aromatic amine derivative or the above polymer in the mixture is ≤15 wt %;

In one embodiment, the weight percentage of the above aromatic amine derivative or the above polymer in the mixture is ≤12 wt %;

In one embodiment, the weight percentage of the above aromatic amine derivative or the above polymer in the mixture is ≤9 wt %;

In one embodiment, the weight percentage of the above aromatic amine derivative or the above polymer in the mixture is ≤8 wt %;

In one embodiment, the weight percentage of the above aromatic amine derivative or the above polymer in the mixture is ≤7 wt %;

In one embodiment, the mixture comprises the above aromatic amine derivative or the above polymer; another fluorescence emitter (or singlet emitter) and a fluorescent host material. Wherein, the above aromatic amine derivative or the above polymer may be used as an auxiliary light emitting material, and the weight ratio of the above aromatic amine derivative or the above polymer to the fluorescent emitter is from 1:2 to 2:1.

In certain embodiments, the mixture comprises one of the above aromatic amine derivative or the above polymer, and TADF material.

In another embodiment, the mixture comprises one if the above aromatic amine derivative or the above polymer, and HTM material.

The HTM, singlet host materials, singlet emitters and TADF materials are described in more detail below (but are not limited thereto).

1. HIM/HTM/EBM

Suitable organic HIM/HTM materials may be selected from the compounds containing the following structural units: phthalocyanine, porphyrin, amine, aromatic amine, biphenyl triarylamine, thiophene, fused thiophene such as dithienothiophene and bithiophene, pyrrole, aniline, carbazole, indolocarbazole, and derivatives thereof. In addition; suitable HTM also comprises self-assembled monomers such as compound containing phosphonic acid and silane derivatives; metal clathrate and cross-linking compound.

The electron blocking layer (EBL) is used to block electrons from the adjacent functional layers, particularly the light emitting layers. The presence of the EBL generally leads to an increase in luminous efficiency, comparing to a light emitting device without the blocking layer. The electron blocking material (EBM) of the electron blocking layer (EBL) requires a higher LUMO than the adjacent functional layer such as light emitting layer. In an embodiment, HBM has a larger excited state energy level such as singlet state or triplet state than the adjacent light emitting layer, depending on the emitter, while the EBM has a hole transport function, Generally, HIM/HTM materials, which have high LUMO energy level, can be used as EBM.

Examples of cyclic aromatic amine-derived compounds that can be used as HIM, HTM, or EBM; include but are not limited to the following general structures:

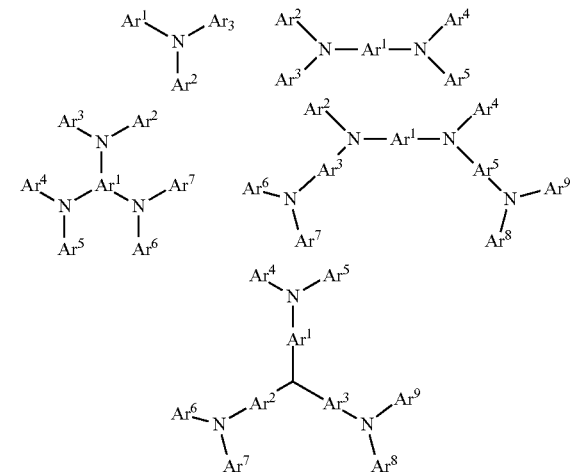

Each of $Ar^1$ to $Ar^9$ may be independently selected from the group consisting of cyclic aromatic hydrocarbon compound such as benzene, biphenyl, triphenyl, benzo, naphthalene, anthracene, phenalene, phenanthrene, fluorene, pyrene, chrysene, perylene, azulene; or aromatic heterocycle compound such as dibenzothiophene, dibenzofuran, furan, thiophene, benzofuran, benzothiophene, carbazole, pyrazole, imidazole, triazole, isoxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indolizine, benzoxazole, benzisoxazole, benzothiazole, quinoline, isoquinoline, cinnoline, quinazoline, quinoxaline, naphthalene, phthalein, pteridine, xanthene, acridine, phenazine phenothiazine, phenoxazine, dibenzoselenophene, benzoselenophene, benzofuropyridine, indolocarbazole, pyridylindole, pyrrolodipyridine, furodipyridine, benzothieopyridine, thienopyridine, benzoselenophenepyridine and selenophenodipyridine; or groups containing 2 to 10 ring structures, which may be the same or different types of cyclic aromatic hydrocarbyl groups or aromatic heterocyclic groups, and linked to each other directly or through at least one of the following groups: such as oxygen atom, nitrogen atom, sulfur atom; silicon atom, phosphorus atom, boron atom, chain structure unit, and aliphatic ring group. Wherein, each Ar may be further substituted, the substituent group may be selected from the group consisting of hydrogen, alkyl, alkoxy, amino, alkenyl, alkynyl, aralkyl, heteroalkyl, aryl and heteroaryl.

In one aspect, $Ar^1$ to $Ar^9$ can be independently selected from the group consisting of:

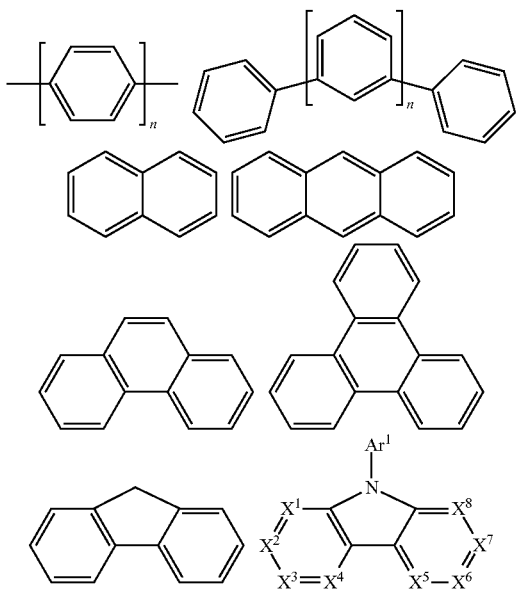

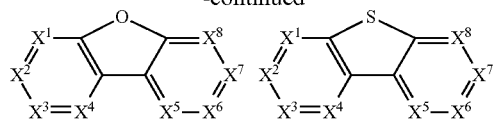

n is an integer of 1 to 20; $X^1$ to $X^8$ are CH or N; $Ar^1$ is as defined above.

Additional examples of cyclic aromatic amine-derived compounds can be seen in U.S. Pat. Nos. 3,567,450, 4,720,432, 5,061,569, 3,615,404 and 5,061,569.

Examples of metal clathrate that can be used as HTM or HTM include but are not limited to the following general structures:

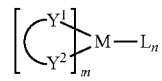

M is a metal with the atomic weight greater than 40;

$(Y^1-Y^2)$ is a bidentate ligand, $Y^1$ and $Y^2$ are independently selected from C, N, O, P or S; L is an auxiliary ligand; m is an integer with the value from 1 to the maximum coordination number of the metal; m+n is the maximum coordination number of this metal.

In an embodiment, $(Y^1-Y^2)$ is a 2-phenylpyridine derivative.

In another embodiment, $(Y^1-Y^2)$ is a carbene ligand.

In another embodiment, M is selected from Ir, Pt, Os and Zn.

In another aspect, the metal clathrate has a HOMO greater than −5.5 eV (relative to the vacuum level).

Suitable examples that can be used as HIM/HTM compounds are listed in the table below.

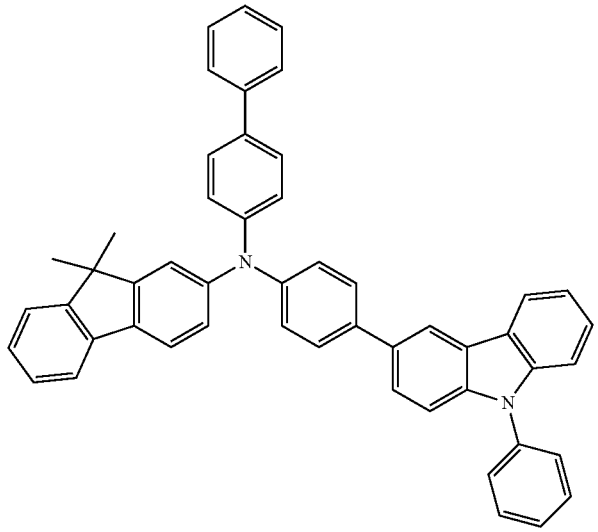 [SMILES: CC1(C)c2ccccc2-c2ccc(N(c3ccc(-c4ccccc4)cc3)c3ccc(-c4ccc5c(c4)c4ccccc4n5-c4ccccc4)cc3)cc21]

-continued
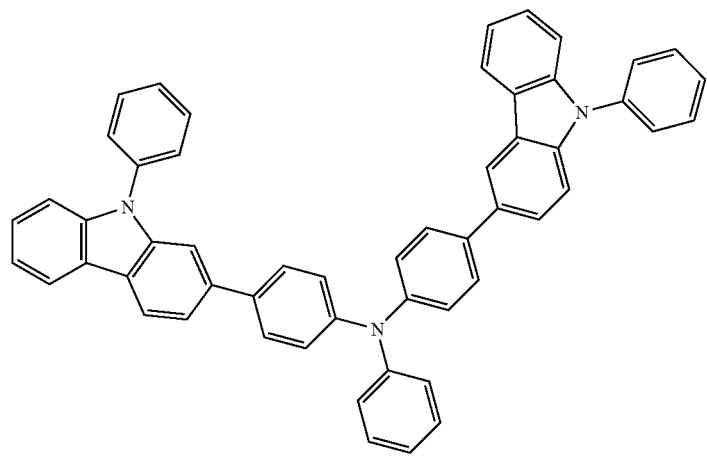 [SMILES: c1ccc(N(c2ccc(-c3ccc4c(c3)c3ccccc3n4-c3ccccc3)cc2)c2ccc(-c3ccc4c5ccccc5n(-c5ccccc5)c4c3)cc2)cc1]
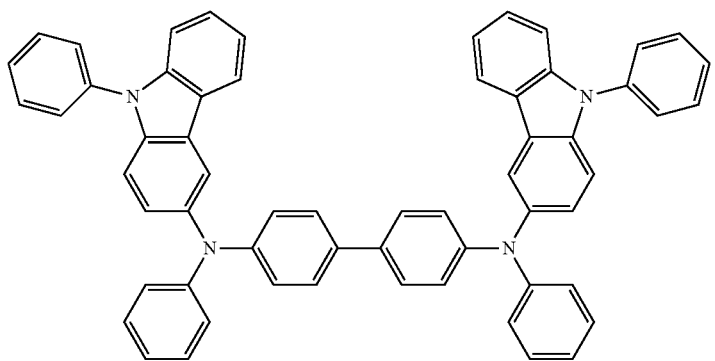 [SMILES: c1ccc(N(c2ccc(-c3ccc(N(c4ccccc4)c4ccc5c(c4)c4ccccc4n5-c4ccccc4)cc3)cc2)c2ccc3c(c2)c2ccccc2n3-c2ccccc2)cc1]
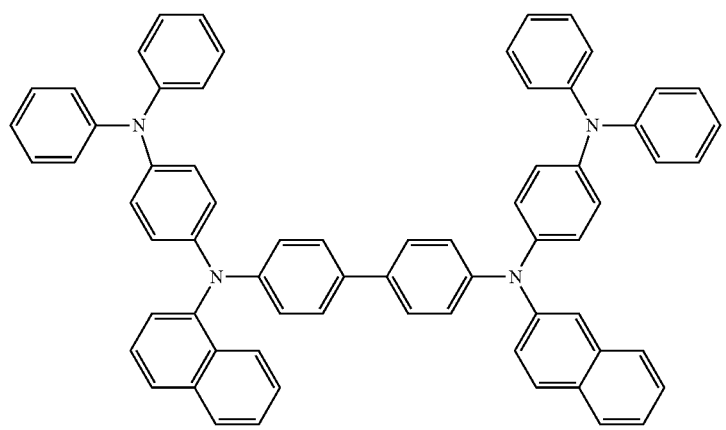 [SMILES: c1ccc(N(c2ccccc2)c2ccc(N(c3ccc(-c4ccc(N(c5ccc(N(c6ccccc6)c6ccccc6)cc5)c5cccc6ccccc56)cc4)cc3)c3ccc4ccccc4c3)cc2)cc1]

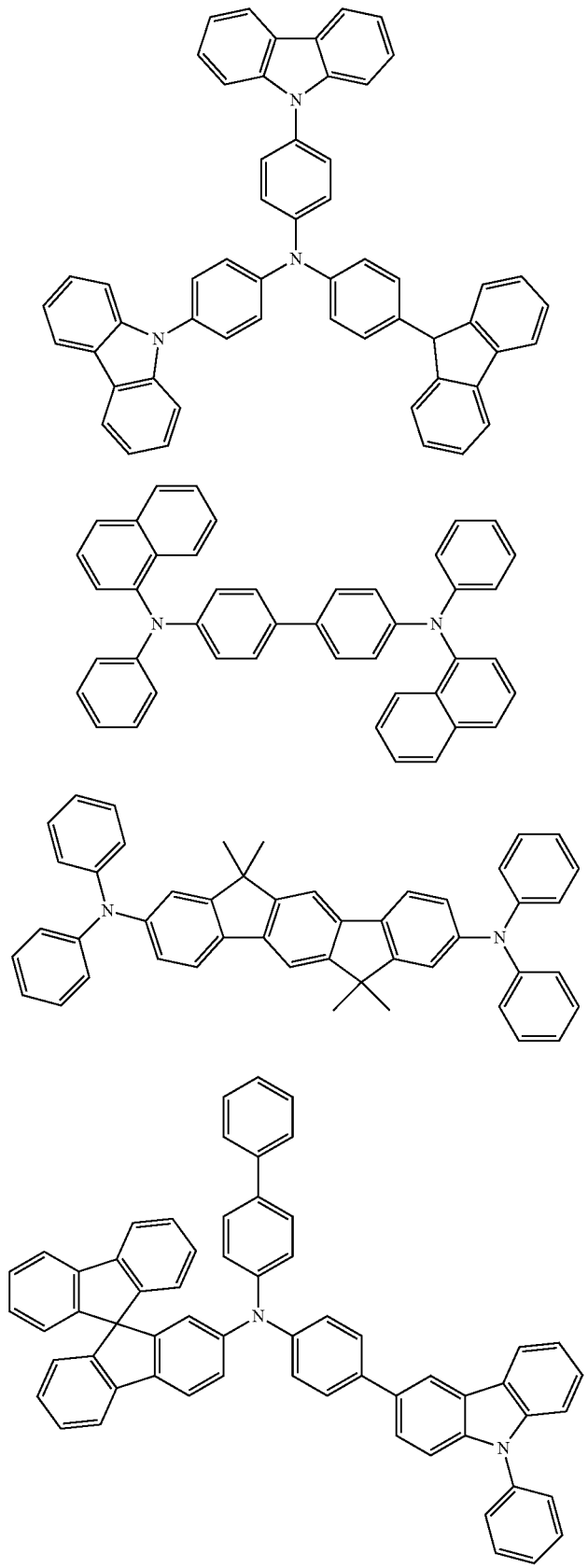

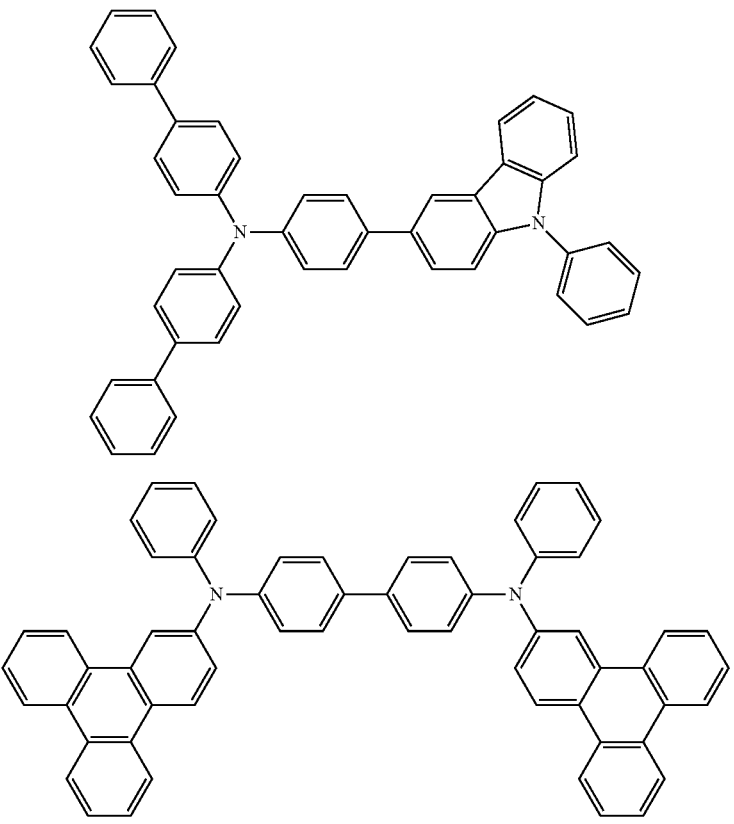

2. Singlet Matrix (Singlet Host) Material:

The example of the singlet host material is not particularly limited, any organic compound can be used as the host as long as its singlet energy is higher than that of the emitter, particularly that of the singlet emitter or the fluorescent emitter.

Examples of organic compounds used as singlet host material are selected from group consisting of: cyclic aromatic hydrocarbon compounds such as benzene, biphenyl, triphenyl, benzo, naphthalene, anthracene, phenalene, phenanthrene, fluorene, pyrene, chrysene, perylene, azulene; or aromatic heterocycles compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, isoxazole, thiazole, oxadiazole, oxytriazole, dioxazole, thiadiazole, pyridine, pyridazine, pyrimidine, pyrazine, triazine, oxazine, oxathiazine, oxadiazine, indole, benzimidazole, indazole, indolizine, benzoxazole, benzoxazole, benzothiazole, quinoline, isoquinoline, cinnoline, quinazoline, quinoxaline, naphthalene, phthalein, pteridine, xanthene, acridine, phenazine, phenothiazine, phenoxazine, benzofuropyridine, furan dipyridine, benzothiophene pyridine, thiophenyldipyridine, benzoselenophenepyridine and selenophenodipyridine; or groups containing 2 to 10 ring structures, which may be the same or different types of cyclic aromatic hydrocarbyl groups or aromatic heterocyclic groups, and linked to each other directly or through at least one of the following groups: oxygen atom, nitrogen atom, sulfur atom, silicon atom, phosphorus atom, boron atom, chain structure unit, and aliphatic ring group.

In one embodiment, the singlet host material may be selected from compounds comprising at least one of the following groups:

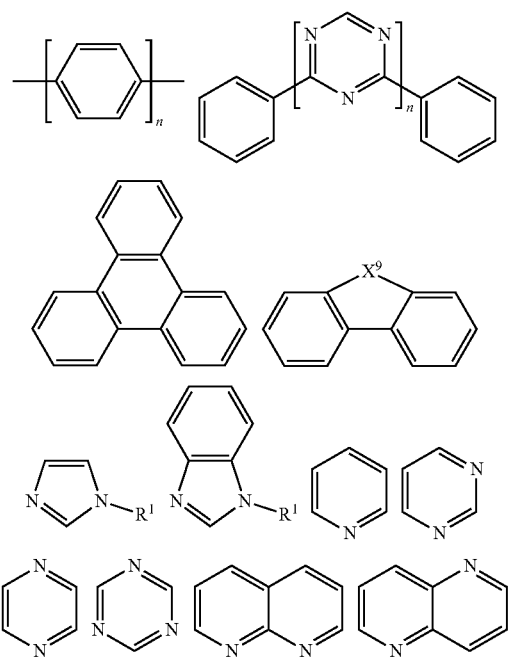

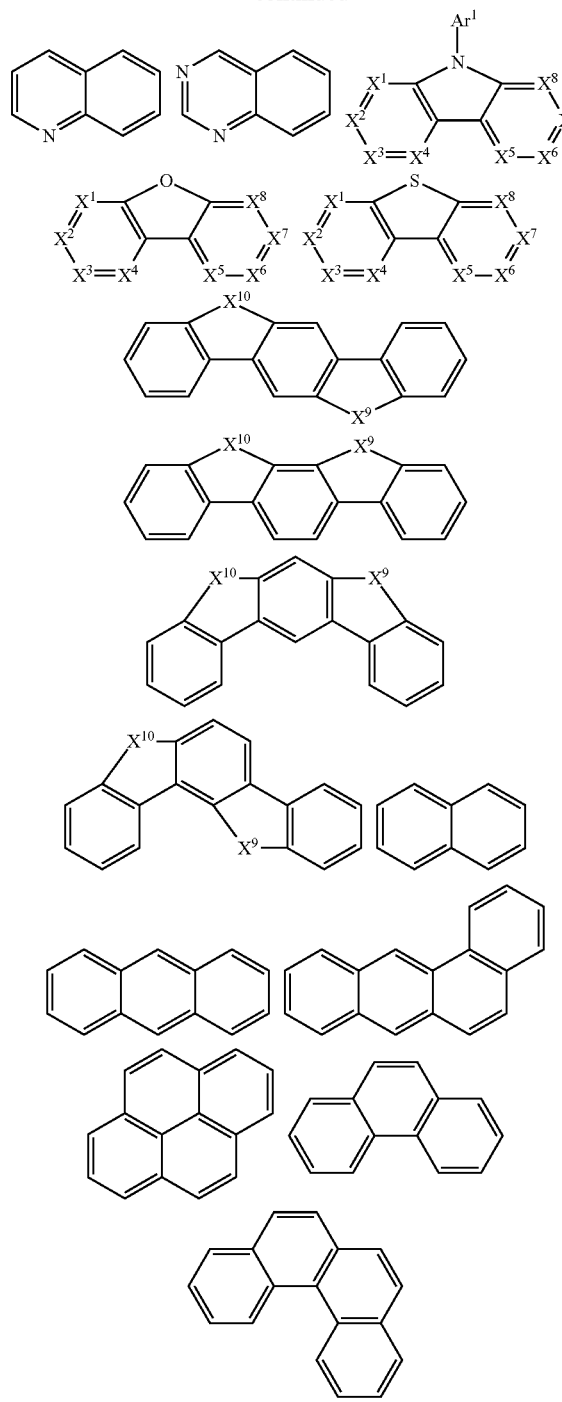

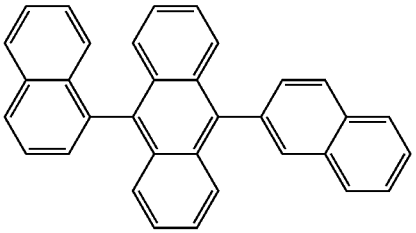

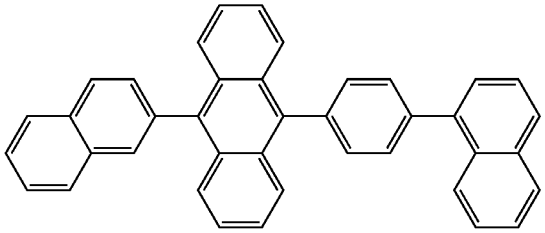

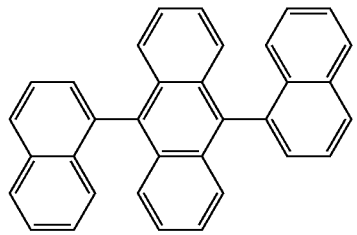

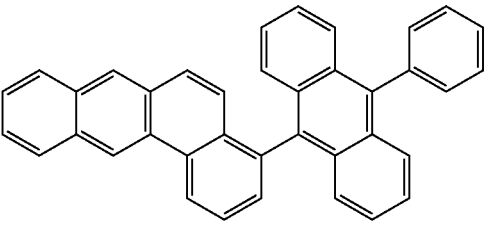

Wherein, $R^1$ may be independently selected from the group consisting of hydrogen, alkyl, alkoxy, amino, alkene, alkynyl, aralkyl, heteroalkyl, aryl and heteroaryl; $Ar^1$ is aryl or heteroaryl, and has the same meaning as $Ar^1$ defined in the above HTM; n is an integer of 0 to 20; $X^1$ to $X^8$ are selected from CH or N; $X^9$ and are selected from $CR^1R^2$ or $NR^1$.

Some examples of anthracene-based singlet host material are listed in the table below:

3. Singlet Emitter

The singlet emitter usually has longer conjugated a electron system. To date, there have been many examples, such as, styrylamine and derivatives thereof disclosed in JP2913116B and WO2001021729A1, and indenofluorene and derivatives thereof disclosed in WO2008/006449 and WO2007/140847.

In one embodiment, the singlet emitter can be selected from the group consisting of mono-styrylamine, di-styrylamine, tri-styrylamine, tetra-styrylamine, styryl phosphine, styryl ether and arylamine.

A mono-styrylamine is a compound comprising an unsubstituted or substituted styryl group and at least one amine, particularly an aromatic amine. A di-styrylamine is a compound comprising two unsubstituted or substituted styryl groups and at least one amine, particularly an aromatic amine. A tri-styrylamine is a compound comprising three unsubstituted or substituted styryl groups and at least one amine, particularly an aromatic amine. A tetra-styrylamine is a compound comprising four unsubstituted or substituted styryl groups and at least one amine, particularly an aromatic amine. A preferred styrene is stilbene, which may be further substituted. The definitions of the corresponding phosphines and ethers are similar to those of amines. An aryl amine or aromatic amine refers to a compound comprising three unsubstituted or substituted aromatic cyclic or heterocyclic systems directly coupled to nitrogen. At least one of such aromatic or heterocyclic ring systems is particularly selected from fused ring system, and particularly has at least 14 aromatic ring atoms. Wherein, preferred examples are aromatic anthramine, aromatic anthradiamine, aromatic pyrenamine, aromatic pyrenediamine, aromatic chryseneamine or aromatic chrysenediamine. An aromatic anthramine refers to a compound in which a diarylamino group is directly coupled to the anthracene, particularly at position 9. An aromatic anthradiamine refers to a compound in which two diarylamino groups are directly coupled to the anthracene, particularly at positions 9, 10. The aromatic pyrenamine, aromatic pyrenediamine, aromatic chryseneamine and aromatic chrysenediamine are similarly defined, wherein the diarylarylamino group is particularly coupled to position 1 or 1, 6 of pyrene.

The examples of singlet emitters based on vinylamine and arylamine are also preferred examples which may be found in the following patent documents: WO2006/000388, WO 2006/058737, WO 2006/000389, WO 2007/065549, WO 2007/115610, U.S. Pat. No. 7,250,532 B2, DE 102005058557 A1, CN 1583691 A, JP 08053397 A, U.S. Pat. No. 6,251,531 B1, US 2006/210830 A, EP 1 957 606 A1 and US 2008/0113101 A1, the entirety of the patent documents listed above are hereby incorporated herein by reference.

Examples of singlet emitters based on distyryibenzene and derivatives thereof can be seen in U.S. Pat. No. 5,121,029.

Further preferred singlet emitters may be selected from the group consisting of: indenofluorene-amine and indenofluorene-diamine such as disclosed in WO2006/122630, benzoindenofluorene-amine and benzoindenofluorene-diamine such as disclosed in WO 2008/006449, dibenzoindenofluorene-amine and dibenzoindenofluorene-diamine such as disclosed in WO2007/140847.

Other materials that can be used as singlet emitters are polycyclic aromatic hydrocarbon compounds, particularly the derivatives of the following compounds: anthracene such as 9,10-di(2-naphthanthracene), naphthalene, tetracene, xanthene, phenanthrene, pyrene (such as 2,5,8,11-tetra-t-butylperylene), indenopyrene, phenylene (such as 4,4-(bis (9-ethyl-3-carbazovinylene)-1,1'-biphenyl), periflanthene, decacyclene, coronene, fluorene, spirobifluorene, arylpyrene (e.g., US20060222886), arylenevinylene (e.g., U.S. Pat. No. 5,121,029, 5,130,603), cyclopentadiene such as tetraphenylcyclopentadiene, rubrene, coumarine, rhodamine, quinacridone, pyrane such as 4 (dicyanomethylene)-6-(4-dimethylaminostyryl-2-methyl)-4H-pyrane (DCM), thiapyran, bis (azinyl) imine-boron compounds (US 2007/0092753 A1), his (azinyl) methene compounds, carbostyryl compounds, oxazone, benzoxazole, benzothiazole, benzimidazole, and diketopyrrolopyrrole. Some materials of singlet emitter may be found in the following patent documents: US 20070252517 A1, U.S. Pat. Nos. 4,769,292, 6,020,078, US 2007/0252517 A1, US 2007/0252517 A1, The entire contents of the patent documents listed above are hereby incorporated herein by reference.

Examples of Suitable Singlet Emitters are Listed Below:

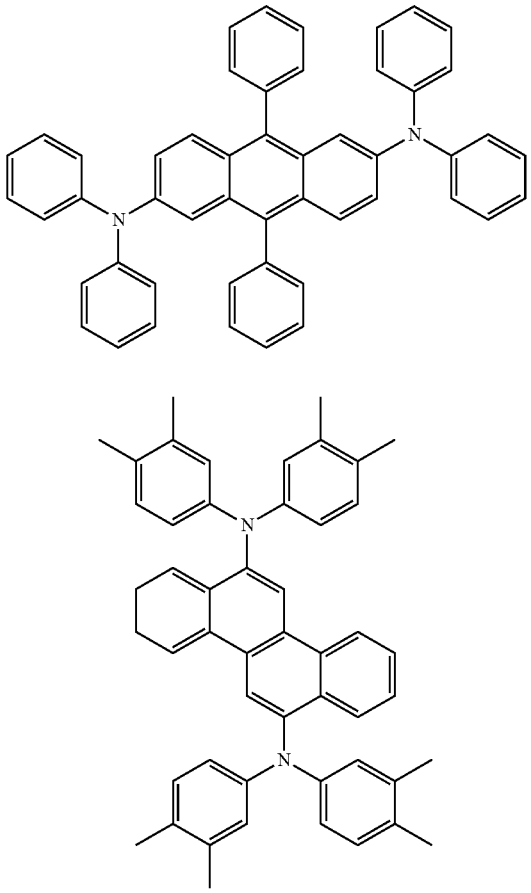

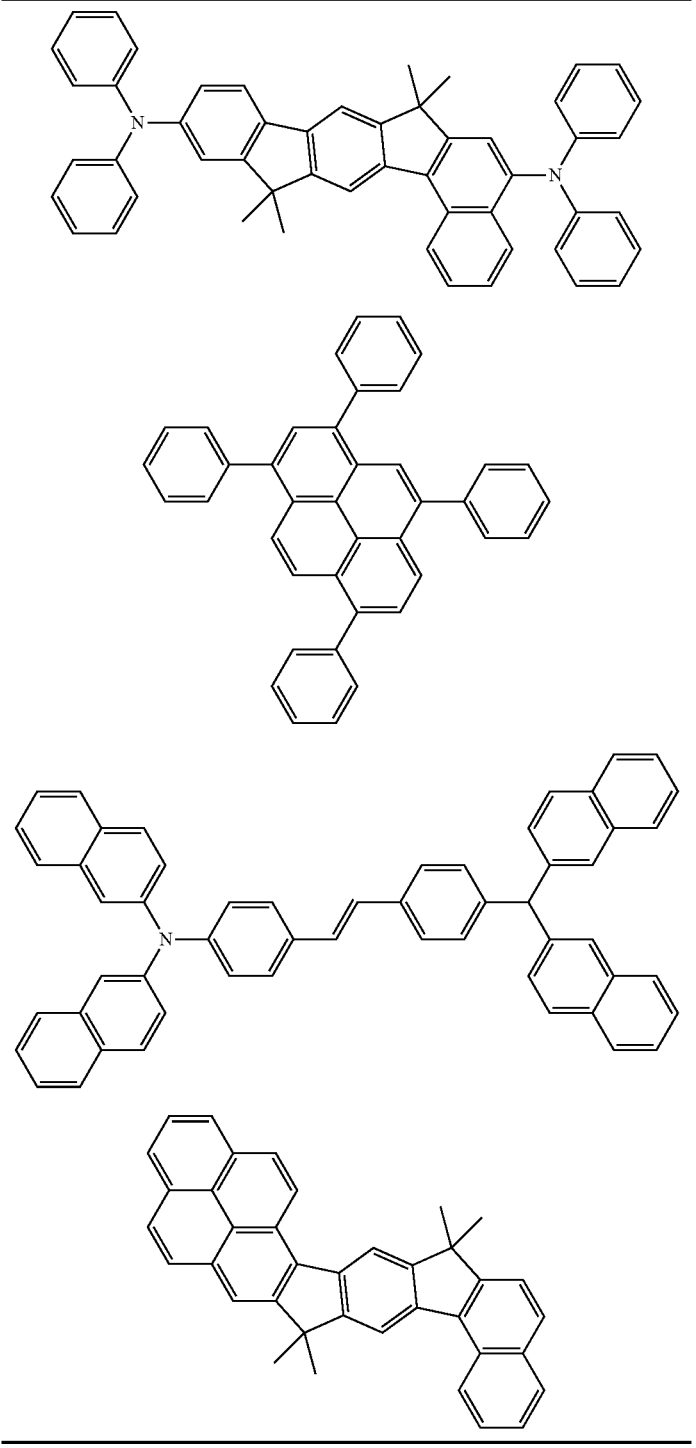

4. Thermally Activated Delayed Fluorescent Material (TADF Material)

Traditional organic fluorescent materials can only use 25% singlet exciton formed by electrical excitation to emit light, and internal quantum efficiency of the devices is relatively low (up to 25%). The phosphorescent material enhances the intersystem crossing due to the strong spin-orbit coupling of the heavy atom center, and can emit light effectively using the singlet exciton and the triplet exciton formed by the electric excitation, so that internal quantum efficiency of the device can reach 100%. However, the application of phosphorescent material in OLEDs is limited by the problems such as high cost, poor material stability and serious roll-off of the device efficiency, etc. Thermally activated delayed fluorescent materials are the third generation of organic light-emitting materials after organic fluorescent materials and organic phosphorescent materials. This type of material generally has a small singlet-triplet energy level difference (ΔEst), and triplet excitons can be converted to singlet excitons by intersystem crossing to emit light. Which can fully use singlet excitons and triplet excitons formed under electric excitation can be fully utilized. The internal quantum efficiency of the device can reach 100%. At the same time, the material is controllable in structure, stable in property, low cost, unnecessary to use precious metals, and have a promising application prospect in the OLED field.

TADF material needs to have smaller singlet-triplet energy level difference, in one embodiment ΔEst<0.3 eV, further ΔEst<0.2 eV, and still further ΔEst<0.1 eV In an embodiment, TADF material has a relatively small ΔEst, and in another embodiment, TADF has better fluorescence quantum efficiency. Some TADF materials can be found in the following patent documents: CN103483332(A), TW201309696(A), TW201309778(A), TW201343874(A), TW201350558(A), US20120217869(A1), WO2013133359 (A1), WO2013154064(A1), Adachi, et. al. Adv. Mater., 21, 2009, 4802, Adachi, et. al. Appl. Phys. Lett., 98, 2011, 083302, Adachi, et. al. Appl. Phys, Lett., 101, 2012, 093306, Adachi, et. al. Chem. Commun., 48, 2012, 11392, Adachi, et. al. Nature Photonics, 6, 2012, 253, Adachi, et. al. Nature, 492, 2012, 234, Adachi, et. al. J. Am. Chem. Sac, 134, 2012, 14706, Adachi, et. al. Angew. Chem. Int. Ed, 51, 2012, 11311, Adachi, et. al. Chem. Commun., 48, 2012, 9580, Adachi, et. al. Chem. Commun., 48, 2013, 10385, Adachi, et. al. Adv. Mater., 25, 2013, 3319, Adachi, et. al. Adv, Mater., 25, 2013, 3707, Adachi, et. al. Chem. Mater., 25, 2013, 3038, Adachi, et. al. Chem. Mater., 25, 2013, 3766, Adachi, et. al. J. Mater. Chem. C., 1, 2013, 4599, Adachi, et. al. J. Phys. Chem. A., 117, 2013, 5607, all contents of the above-listed patents or article documents are hereby incorporated herein by reference in their entirety.

Some examples of suitable TADF light-emitting materials are listed in the following table:

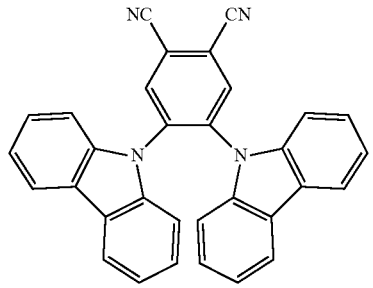 [SMILES: N#Cc1cc(-n2c3ccccc3c3ccccc32)c(-n2c3ccccc3c3ccccc32)cc1C#N]

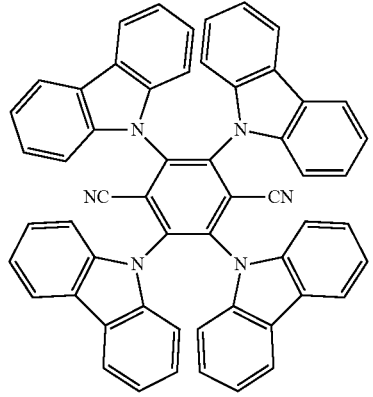 [SMILES: N#Cc1c(-n2c3ccccc3c3ccccc32)c(-n2c3ccccc3c3ccccc32)c(C#N)c(-n2c3ccccc3c3ccccc32)c1-n1c2ccccc2c2ccccc21]

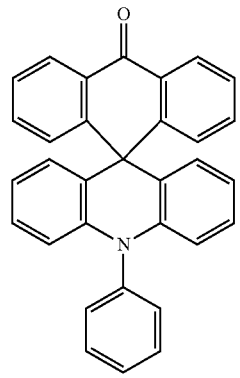 [SMILES: O=C1c2ccccc2C2(c3ccccc31)c1ccccc1N(c1ccccc1)c1ccccc12]

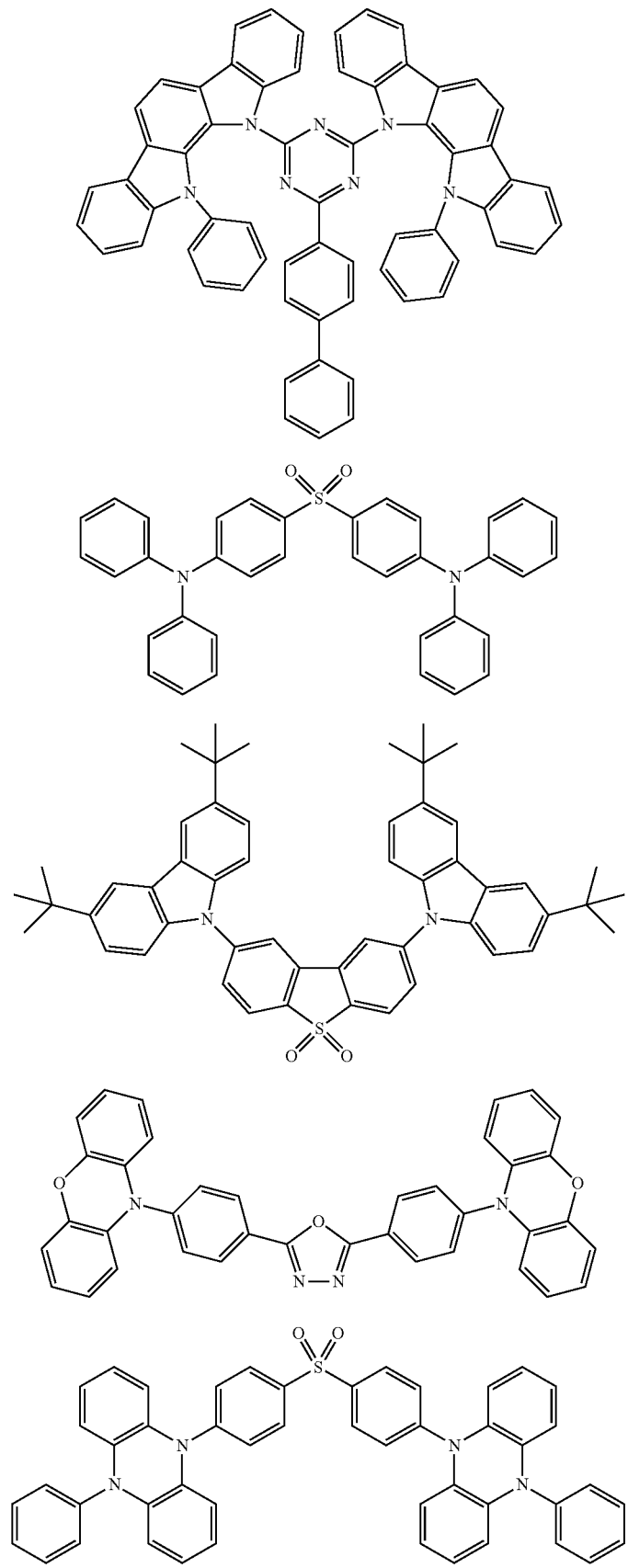

-continued
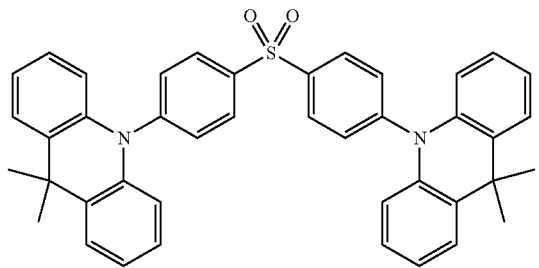
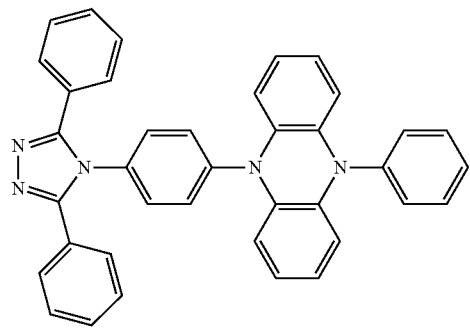 [SMILES: c1ccc(-c2nnc(-c3ccccc3)n2-c2ccc(N3c4ccccc4N(c4ccccc4)c4ccccc43)cc2)cc1]
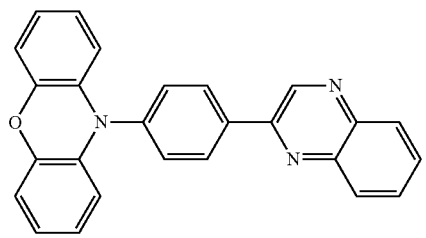 [SMILES: c1ccc2c(c1)Oc1ccccc1N2c1ccc(-c2cnc3ccccc3n2)cc1]
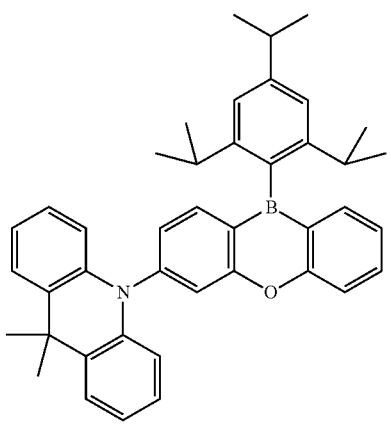 [SMILES: CC(C)c1cc(C(C)C)c(B2c3ccccc3Oc3cc(N4c5ccccc5C(C)(C)c5ccccc54)ccc32)c(C(C)C)c1]
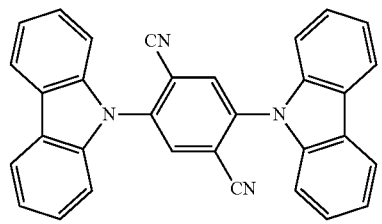 [SMILES: N#Cc1cc(-n2c3ccccc3c3ccccc32)c(C#N)cc1-n1c2ccccc2c2ccccc21]

-continued
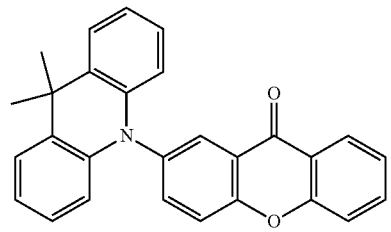 [SMILES: CC1(C)c2ccccc2N(c2ccc3oc4ccccc4c(=O)c3c2)c2ccccc21]
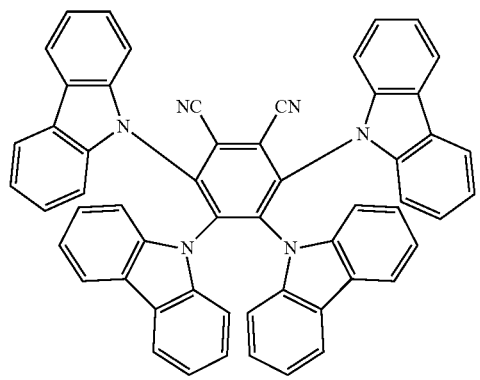 [SMILES: N#Cc1c(C#N)c(-n2c3ccccc3c3ccccc32)c(-n2c3ccccc3c3ccccc32)c(-n2c3ccccc3c3ccccc32)c1-n1c2ccccc2c2ccccc21]
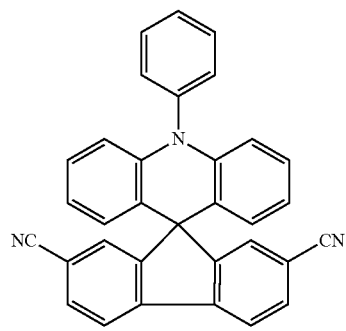 [SMILES: N#Cc1ccc2c(c1)C1(c3cc(C#N)ccc3-2)c2ccccc2N(c2ccccc2)c2ccccc21]
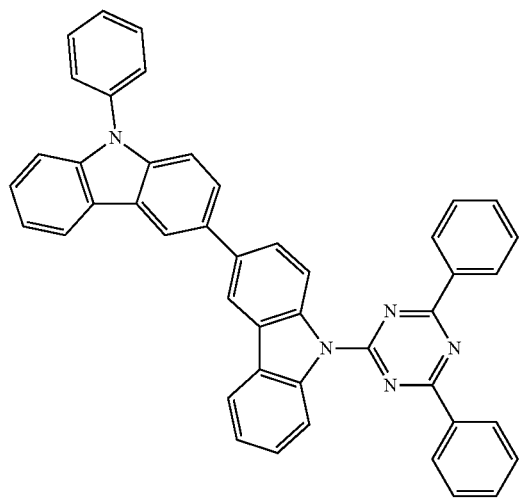 [SMILES: c1ccc(-c2nc(-c3ccccc3)nc(-n3c4ccccc4c4cc(-c5ccc6c(c5)c5ccccc5n6-c5ccccc5)ccc43)n2)cc1]

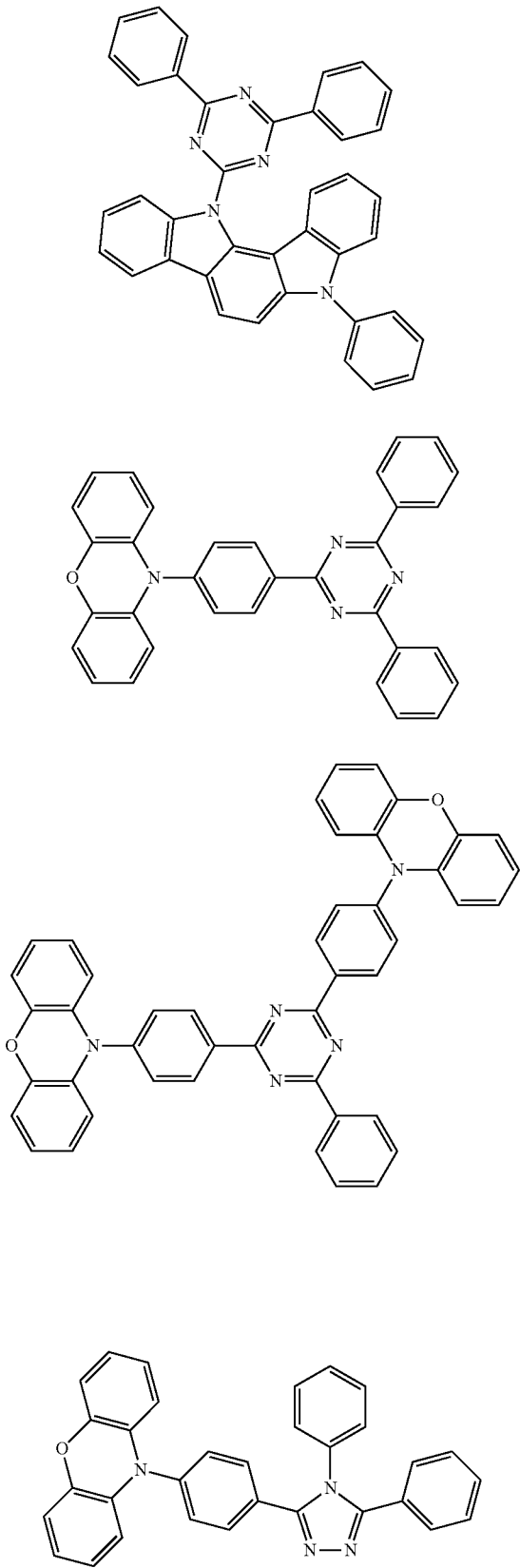

-continued
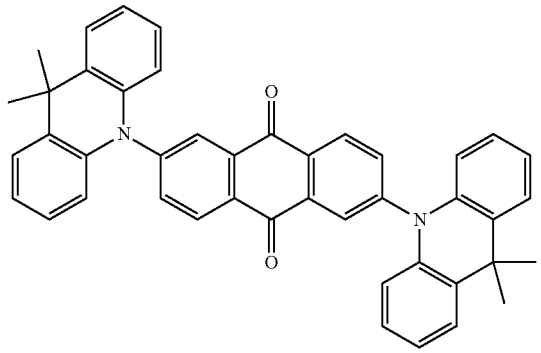
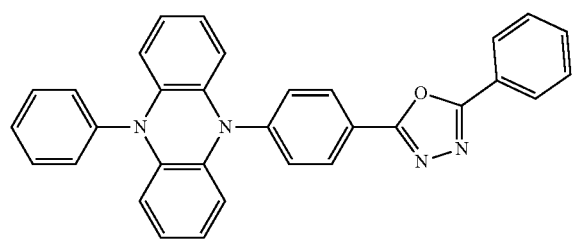 [SMILES: c1ccc(-c2nnc(-c3ccc(N4c5ccccc5N(c5ccccc5)c5ccccc54)cc3)o2)cc1]
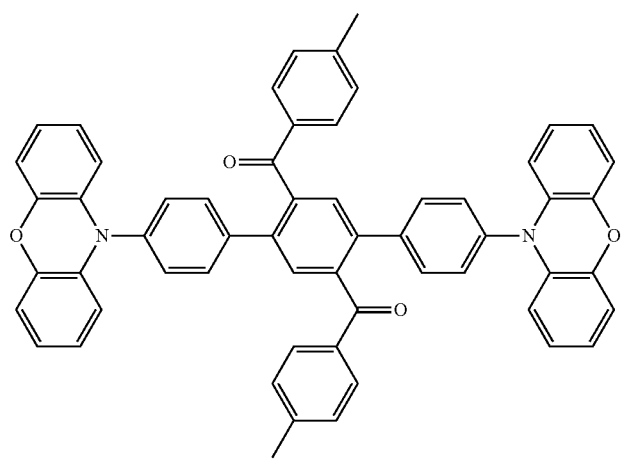 [SMILES: Cc1ccc(C(=O)c2cc(-c3ccc(N4c5ccccc5Oc5ccccc54)cc3)c(C(=O)c3ccc(C)cc3)cc2-c2ccc(N3c4ccccc4Oc4ccccc43)cc2)cc1]
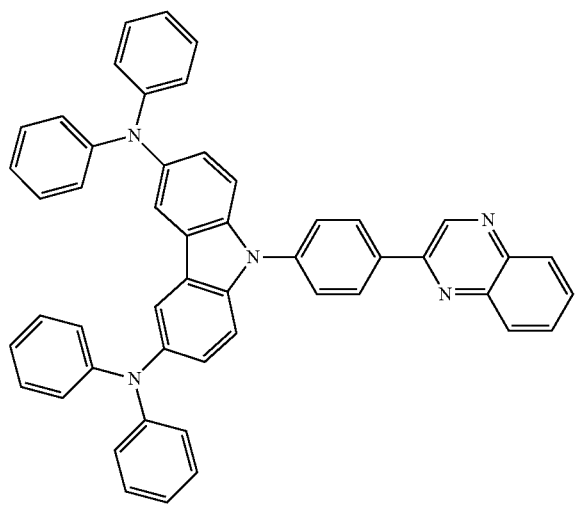 [SMILES: c1ccc(N(c2ccccc2)c2ccc3c(c2)c2cc(N(c4ccccc4)c4ccccc4)ccc2n3-c2ccc(-c3cnc4ccccc4n3)cc2)cc1]

-continued
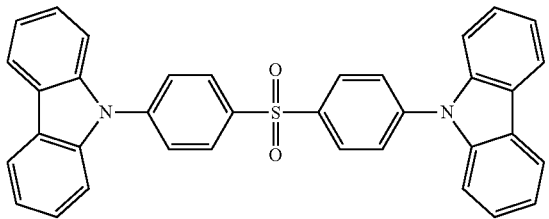 [SMILES: O=S(=O)(c1ccc(-n2c3ccccc3c3ccccc32)cc1)c1ccc(-n2c3ccccc3c3ccccc32)cc1]
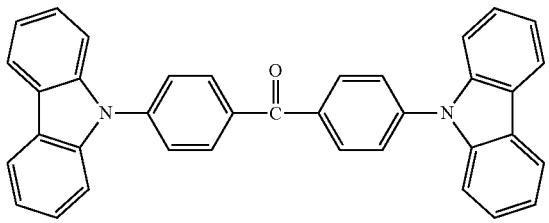 [SMILES: O=C(c1ccc(-n2c3ccccc3c3ccccc32)cc1)c1ccc(-n2c3ccccc3c3ccccc32)cc1]
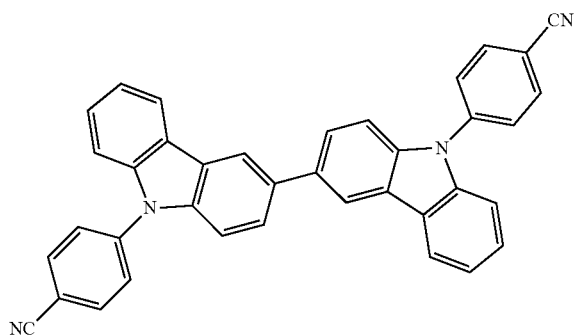 [SMILES: N#Cc1ccc(-n2c3ccccc3c3cc(-c4ccc5c(c4)c4ccccc4n5-c4ccc(C#N)cc4)ccc32)cc1]
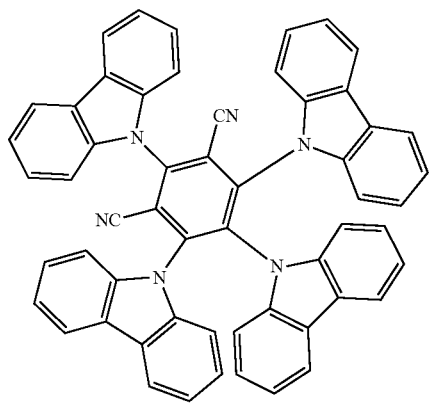 [SMILES: N#Cc1c(-n2c3ccccc3c3ccccc32)c(C#N)c(-n2c3ccccc3c3ccccc32)c(-n2c3ccccc3c3ccccc32)c1-n1c2ccccc2c2ccccc21]
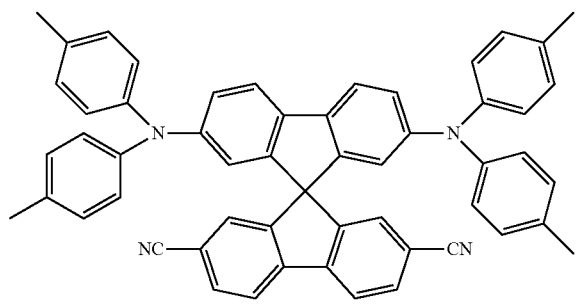

-continued
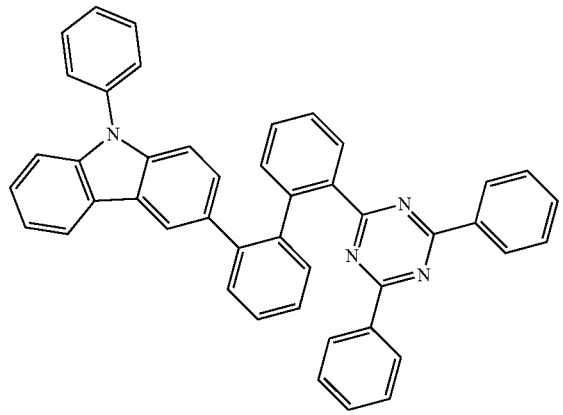 [SMILES: c1ccc(-c2nc(-c3ccccc3)nc(-c3ccccc3-c3ccccc3-c3ccc4c(c3)c3ccccc3n4-c3ccccc3)n2)cc1]
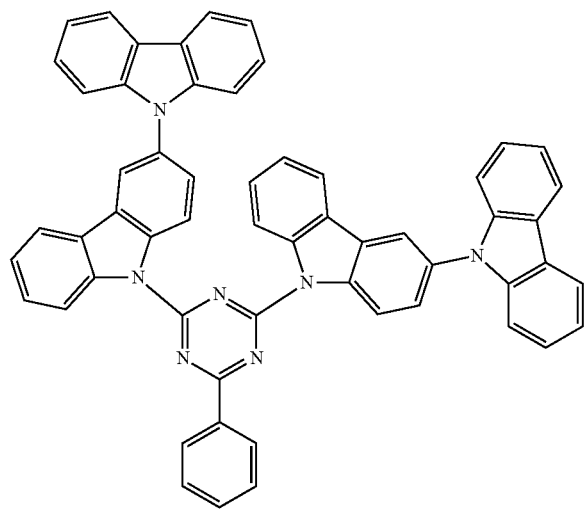 [SMILES: c1ccc(-c2nc(-n3c4ccccc4c4cc(-n5c6ccccc6c6ccccc65)ccc43)nc(-n3c4ccccc4c4cc(-n5c6ccccc6c6ccccc65)ccc43)n2)cc1]
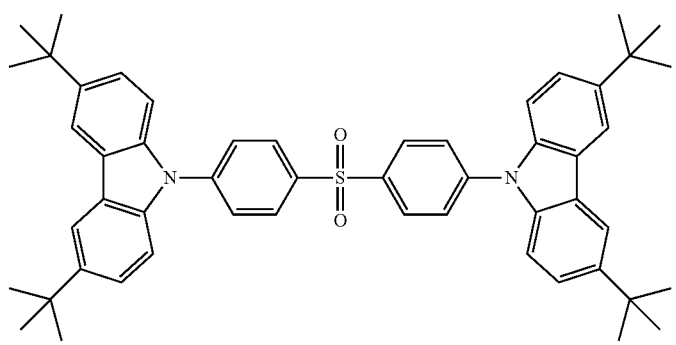 [SMILES: CC(C)(C)c1ccc2c(c1)c1cc(C(C)(C)C)ccc1n2-c1ccc(S(=O)(=O)c2ccc(-n3c4ccc(C(C)(C)C)cc4c4cc(C(C)(C)C)ccc43)cc2)cc1]
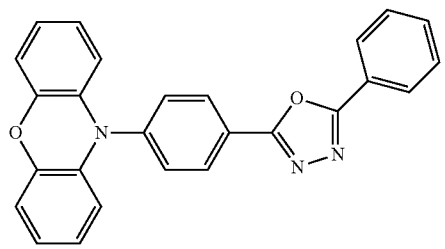 [SMILES: c1ccc(-c2nnc(-c3ccc(N4c5ccccc5Oc5ccccc54)cc3)o2)cc1]

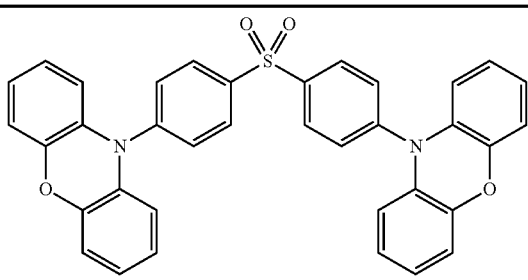
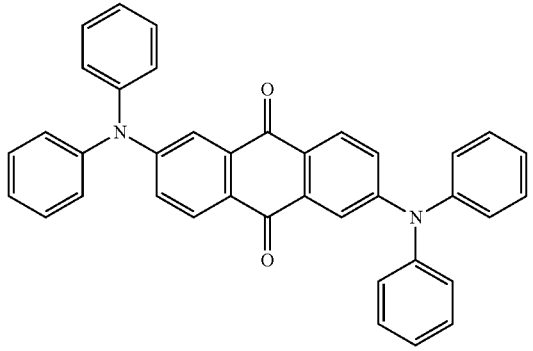 [SMILES: O=C1c2ccc(N(c3ccccc3)c3ccccc3)cc2C(=O)c2ccc(N(c3ccccc3)c3ccccc3)cc21]
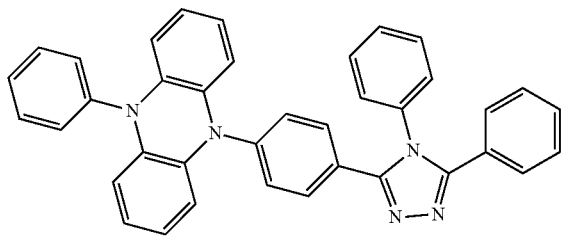 [SMILES: c1ccc(-c2nnc(-c3ccc(N4c5ccccc5N(c5ccccc5)c5ccccc54)cc3)n2-c2ccccc2)cc1]
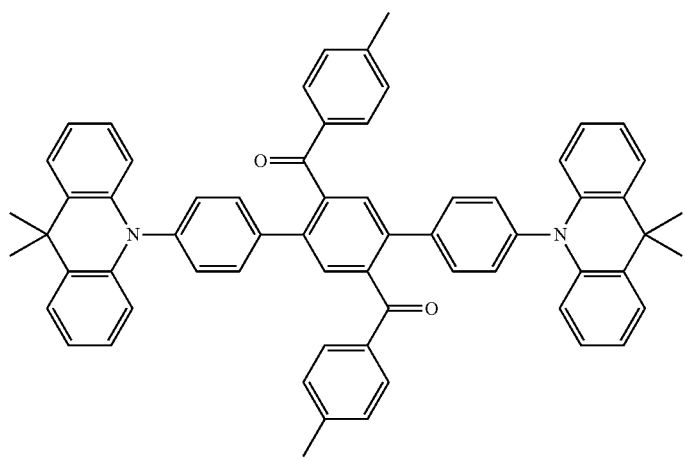
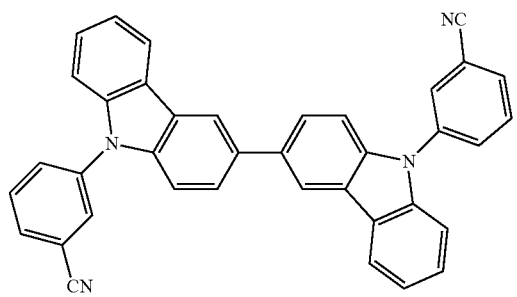 [SMILES: N#Cc1cccc(-n2c3ccccc3c3cc(-c4ccc5c(c4)c4ccccc4n5-c4cccc(C#N)c4)ccc32)c1]

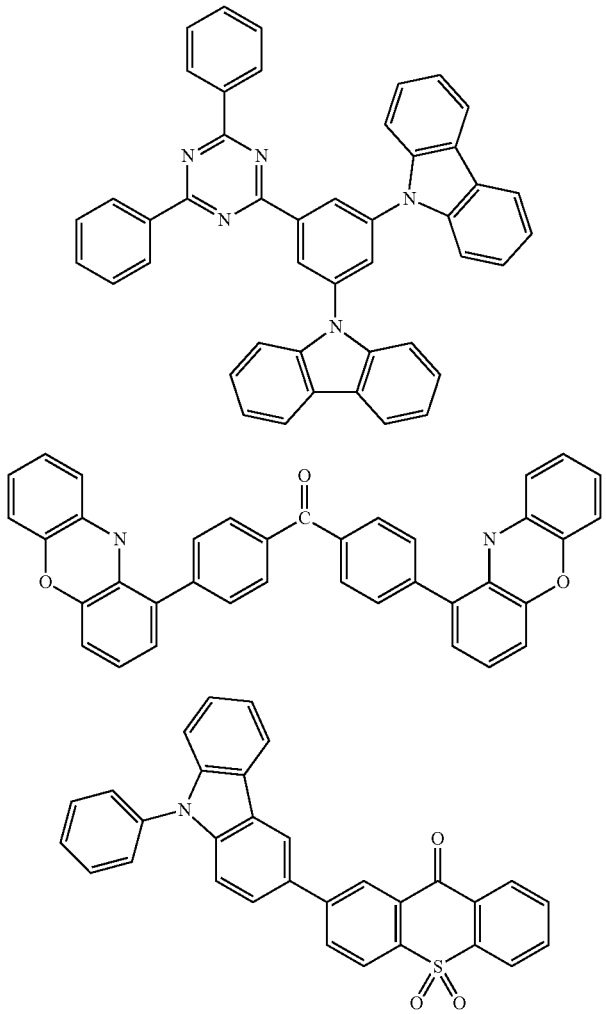

The publications of organic functional materials mentioned above are incorporated herein by reference for the purpose of disclosure.

A formulation comprises the above aromatic amine derivative or the polymer thereof or the above mixture, and organic solvent.

In some embodiments, the deuterated aromatic amine derivative is used as singlet emitter material.

In one embodiment, a formulation comprises a host material and the above aromatic amine derivative or the polymer thereof or the above mixture.

In another embodiment, a formulation comprises at least two host materials and the above aromatic amine derivative or the polymer thereof or the above mixture.

In another embodiment, a formulation comprises a host material, a thermally activated delayed fluorescent material and the above aromatic amine derivative or the polymer thereof or the above mixture.

In another embodiment, a formulation comprises a hole transport material (HTM) and the above aromatic amine derivative or the polymer thereof or the above mixture.

In another embodiment, a formulation comprises a hole transport material (HTM) comprising a crosslinkable group, and the above aromatic amine derivative or the polymer thereof or the above mixture.

In one embodiment, the formulation described above is a solution.

In another embodiment, the formulation described above is a suspension.

In one embodiment, the formulation comprises 0.01 wt % to 20 wt % of the above aromatic amine derivative or polymer thereof or the above mixture;

In one embodiment, the formulation comprises 0.1 wt % to 15 wt % of the above aromatic amine derivative or polymer thereof or the above mixture;

In one embodiment, the formulation comprises 0.2 wt % to 10 wt % of the above aromatic amine derivative or polymer thereof or the above mixture;

In one embodiment, the formulation comprises 0.25 wt % to 5 wt % of the above aromatic amine derivative or polymer thereof or the above mixture.

In one embodiment, the solvent in the formulation is selected from: aromatic or heteroaromatic, ester, aromatic ketone or aromatic ether, aliphatic ketone or aliphatic ether, alicyclic or olefinic compound, or inorganic ester compound such as borate ester or phosphate ester, or a mixture of two or more solvents.

In one embodiment, a formulation comprising at least 50 wt % of aromatic or heteroaromatic solvent;

In one embodiment, a formulation comprising at least 80 wt % of aromatic or heteroaromatic solvent;

In one embodiment, a formulation comprising at least 90 wt % of aromatic or heteroaromatic solvent;

In one embodiment, examples based on the aromatic or heteroaromatic solvent include, but are not limited to: 1-tetralone, 3-phenoxytoluene, acetophenone, 1-methoxynaphthalene, p-diisopropylbenzene, amylbenzene, tetrahydronaphthalene, cyclohexylbenzene, chloronaphthalene, 1,4-dimethylnaphthalene, 3-isopropylbiphenyl, p-methylisopropylbenzene, dipentyibenzene, o-diethylbenzene, m-diethylbenzene, p-diethylbenzene, 1,2,3,4-tetramethylbenzene, 1,2,3,5-tetramethylbenzene, 1,2,4,5-tetramethylbenzene, butylbenzene, dodecylbenzene 1-methylnaphthalene, 1,2,4-trichlorobenzene, 1,3-dipropoxybenzene, 4,4-difluorodiphenylmethane, diphenyl ether, 1,2-dimethoxy-4-(1-propenyl)benzene, diphenylmethane, 2-phenylpyridine, 3-phenylpyridine, 2-phenoxymethyl ether, 2-phenoxytetrahydrofuran, ethyl-2-naphthyl ether, N-methyldiphenylamine, 4-isopropylbiphenyl, -dichlorodiphenylmethane, 4-(3-phenylpropyl)pyridine, benzylbenzoate, 1,1-bis(3,4-dimethylphenyl)ethane, 2-isopropylnaphthalene, dibenzyl ether, and the like.

In other embodiments, the appropriate and preferred solvent is aliphatic, alicyclic or aromatic hydrocarbon, amine, thiol, amide, nitrile, ester, ether, polyether, alcohol, diol or polyol.

In other embodiments, the alcohol represents an appropriate class of the solvent. Preferred alcohol includes alkylcyclohexanol, particularly methylated aliphatic alcohol, naphthol, and the like.

The solvent may be a cycloalkane, such as decalin.

The solvent may be used alone or used as a mixture of two or more organic solvents.

In certain embodiments, the above formulation comprises the above aromatic amine derivative or polymer thereof and at least one organic solvent, may also further comprise another organic solvent whose examples include, but are not limited to, methanol, ethanol, 2-methoxyethanol, dichloromethane, trichloromethane, chlorobenzene, o-dichlorobenzene, tetrahydrofuran, anisole, morpholine, toluene, o-xylene, m-xylene, p-xylene, 1,4-dioxane, acetone, methyl ethyl ketone, 1,2-dichloroethane, 3-phenoxytoluene, 1,1,1-trichloroethane, 1,1,2,2-tetrachloroethane, ethyl acetate, butyl acetate, dimethylformamide, dimethylacetamide, dimethyl sulfoxide, tetrahydronaphthalene, decalin, indene, and/or mixtures thereof.

In one embodiment, the organic solvent in the above formulation is a solvent with Hansen solubility parameters in the following range:

$\delta_d$ (dispersion force) is in the range of 17.0~23.2 MPa$^{1/2}$, especially in the range of 18.5~21.0 MPa$^{1/2}$;

$\delta_p$ (polarity force) is in the range of 0.2~12.5 MPa$^{1/2}$, especially in the range of 2.0~6.0 MPa$^{1/2}$;

$\delta_h$ (hydrogen bonding force) is in the range of 0.9~14.2 MPa$^{1/2}$, especially in the range of 2.0~6.0 MPa$^{1/2}$.

The organic solvent of the above formulation shall be selected in consideration of boiling point parameters thereof. In one embodiment, the boiling point of the organic solvent is ≥150° C.; in one embodiment, the boiling point of the organic solvent is ≥180° C.; in one embodiment, the boiling point of the organic solvent is ≥200° C.; in one embodiment, the boiling point of the organic solvent is ≥250° C.; in one embodiment, the boiling point of the organic solvent is ≥275° C.; in an embodiment, the boiling point of the organic solvent is ≥300° C. Boiling points in these ranges are beneficial for preventing the clogging of the nozzle of the inkjet printing head. The organic solvent can be evaporated from the formulation to form a film comprising the functional material.

In one embodiment, a formulation, in which the viscosity and the surface tension of the selected solvent are described below:

1) its viscosity is in the range of 1 cPs to 100 cPs at 25° C.; and/or 2) its surface tension is in the range of 19 dyne/cm to 50 dyne/cm at 25° C.

The organic solvent of the above formulation shall be selected in consideration of surface tension thereof. The surface tension parameters of suitable ink are suitable for particular substrate and particular printing method. For example, for the inject printing, in one embodiment, the surface tension of the organic solvent at 25° C. is in the range of about 19 dyne/cm to 50 dyne/cm; in one embodiment, the surface tension of the organic solvent at 25° C. is in the range of about 22 dyne/cm to 35 Dyne/cm; in one embodiment, the surface tension of the organic solvent at 25° C. is in the range of about 25 dyne/cm to 33 dyne/cm.

In one embodiment, the surface tension of the ink at 25° C. is in the range of about 19 dyne/cm to 50 dyne/cm; in one embodiment, the surface tension of the ink at 25° C. is in the range of about 22 dyne/cm to 35 dyne/cm; in one embodiment, the surface tension of the ink at 25° C. is in the range of about 25 dyne/cm to 33 dyne/cm.

The organic solvent of the above formulation shall be selected in consideration of the viscosity parameter of the ink thereof. The viscosity can be adjusted by different methods, such as by suitable selection of organic solvent and the concentration of functional materials in the ink. In one embodiment, the viscosity of the organic solvent is less than 100 cps; in one embodiment, the viscosity of the organic solvent is less than 50 cps; in one embodiment, the viscosity of the organic solvent is from 1.5 to 20 cps. The viscosity herein refers to the viscosity during printing at the ambient temperature that is generally at 15-30° C., further 18-28° C., still further 20-25° C., even further 23-25° C. The formulation so formulated will be particularly suitable for inkjet printing.

In one embodiment, a formulation has a viscosity at 25° C. in the range of about 1 cps to 100 cps; in one embodiment, a formulation has a viscosity at 25° C. in the range of about 1 cps to 50 cps range; in one embodiment, a formulation has a viscosity at 25° C. in the range of about 1.5 cps to 20 cps.

The ink obtained from the organic solvent satisfying the above-mentioned boiling point parameter and surface tension parameter and viscosity parameter can form a functional material film with uniform thickness and composition property.

The application of the above aromatic amine derivative or polymer thereof or the formulation in organic electronic devices.

The organic electronic devices can be selected from the group consisting of organic light-emitting diode (OLED), organic photovoltaic cell (OPV), organic light-emitting electrochemical cell (OLEEC), organic field effect transistor (OFET), organic light-emitting field effect transistor, organic laser, organic spintronic device, organic sensor, and organic plasmon emitting diode.

A method for preparing the electronic device; the specific technical solution is as follows:

Forming a functional layer on a substrate by evaporation of the above aromatic amine derivative, polymer thereof or mixture, or forming a functional layer on a substrate by co-evaporation together with at least one other organic functional material, or forming a functional layer by coating the formulation described above on a substrate via printing or coating; wherein the printing or coating method can be selected from, but not limited to; inkjet printing; nozzle printing, letterpress printing, screen printing, dip coating, spin coating, blade coating, roller printing, torsion roll printing, lithography, flexographic printing, rotary printing, spray coating, brush coating, or pad printing, slot die coating, etc.

The use of the formulation described above using as printing ink in preparing organic electronic device. In one embodiment, the organic electronic device described above is prepared by printing or coating preparation method.

Wherein, suitable printing or coating techniques may be inkjet printing, letterpress printing, screen printing; dip coating, spin coating, blade coating, roller printing; torsion roll printing, lithography, flexographic printing, rotary printing, spray coating, brush coating; or pad printing, slot die coating, etc. Especially are gravure printing, screen printing and inkjet printing. Gravure printing, inkjet printing will be applied in embodiments of the disclosure. The solution or the suspension may additionally include one or more components, such as a surfactant compound, a lubricant, a wetting agent; a dispersant, a hydrophobic agent, a binder, to adjust the viscosity and the film forming property and to improve the adhesion property. For more information about printing technologies and relevant requirements thereof on related solutions, such as solvents and concentration, viscosity; etc.; please see Helmut Kipphan, et al., Handbook of Print Media: Technologies and Production Methods, ISBN 3-540-67326-1, edited by Helmut Kipphan.

In one embodiment, the functional layer formed by the preparation method described above has a thickness of 5 nm to 1000 nm.

An organic electronic device at least comprises one of the above aromatic amine derivatives or polymer thereof; or at least comprises a functional layer prepared by using the above formulation.

In one embodiment, an organic electronic device comprises: a cathode, an anode, and a functional layer located between the cathode and the anode, wherein the functional layer at least comprises the above aromatic amine derivative or polymer thereof or the above mixture or the above formulation.

In one embodiment, the organic electronic device described above is an organic electroluminescent device, particularly an OLED, as shown in FIG. 1, wherein comprising a substrate 101, an anode 102, at least one light emitting layer 104 and a cathode 106.

The substrate 101 may be opaque or transparent. A transparent substrate can be used to make a transparent light-emitting device. See, e.g., Bulovic et al. Nature 1996, 380, p 29 and Gu et al. ppl. Phys. Lett. 1996, 68, p 2606. The substrate may be rigid or elastic. The substrate may be plastic, metal, semiconductor wafer or glass. Particularly the substrate has a smooth surface. The substrate without any surface defects is a particularly desirable selection. In one embodiment, the substrate is flexible and may be selected from a polymer thin film or a plastic which has the glass transition temperature $T_g$ of larger than 150° C., further larger than 200° C., still further larger than 250° C., even further larger than 300° C. Suitable examples of the flexible substrate are poly(ethylene terephthalate) (PET) and polyethylene(2,6-naphthalate)(PEN).

The anode 102 may comprise a conductive metal or metal oxide, or a conductive polymer. The anode can inject holes easily into the hole injection layer (HIL), or the hole transport layer (HTL), or the light emitting layer. In one embodiment, the absolute value of the difference between the work function of the anode and the HOMO energy level or the valence band energy level of the emitter in the light-emitting layer or of the p-type semiconductor material of the HIL or HTL or the electron blocking layer (EBL) is less than 0.5 eV, further less than 0.3 eV, even further less than 0.2 eV Examples of anode materials comprise, but not limited to, Al, Cu, Au, Ag, Mg, Fe, Co, Ni, Mn, Pd, Pt, no, aluminum doped zinc oxide (AZO), and the like. Other suitable anode materials are known and may be easily selected by one of ordinary skilled in the art. The anode material may be deposited by any suitable technologies, such as a suitable physical vapor deposition method which includes radio frequency magnetron sputtering, vacuum thermal evaporation, electron beam (e-beam), and the like. In some embodiments, the anode is patterned and structured. Patterned ITO conductive substrates are commercially available and can be used to prepare the device according to the present disclosure.

Cathode 106 may include a conductive metal or metal oxide. The cathode can inject electrons easily into the EIL or ETL, or directly injected into the light-emitting layer. In one embodiment, the absolute value of the difference between the work function of the cathode and the LUMO energy level or the valence band energy level of the emitter in the light-emitting layer or of the n type semiconductor material as the electron injection layer (EIL) or the electron transport layer (ETL) or the hole blocking layer (HBL) is less than 0.5 eV, further less than 0.3 eV, even further less than 0.2 eV. In principle, all materials that can be used as cathodes for OLED can be used as cathode materials for the devices of the disclosure. Examples of the cathode materials comprise, but not limited to: Al, Au, Ag, Ca, Ba, Mg, LiF/Al, MgAg alloy, $BaF_2$/Al, Cu, Fe, Co, Ni, Mn, Pd, Pt, ITO, and the like. The cathode material may be deposited by any suitable technologies, such as the suitable physical vapor deposition method which includes radio frequency magnetron sputtering, vacuum thermal evaporation, electron beam (e-beam), and the like.

OLED can also comprise other functional layers such as hole injection layer (HIL) or hole transport layer (HTL) 103, electron blocking layer (EBL), electron injection layer (EIL) or electron transport layer (ETL) 105, hole blocking layer (HBL). Materials which are suitable for using in these functional layers are described in detail in WO2010135519A1, US20090134784A1 and WO2011110277A1, the entirety of which are hereby incorporated herein by reference.

In one embodiment, the light emitting layer 104 in the light emitting device is prepared by vacuum evaporation, and the evaporation source thereof comprises the above aromatic amine derivative or polymer thereof or formulation thereof or mixture thereof.

In one embodiment, the light emitting layer 104 in the light emitting device is prepared by printing the above aromatic amine derivative of the disclosure or polymer thereof or formulation thereof or mixture thereof.

In one embodiment, the electroluminescent device has an emission wavelength between 300 nm and 1000 nm; in one embodiment, the electroluminescent device has an emission wavelength between 350 nm and 900 nm; in one embodiment, the electroluminescent device has an emission wavelength between 400 nm and 800 nm.

The application of the above organic electronic device in various electronic equipments, comprises but not limited to display equipment, lighting equipment, light source, and sensor and the like.

The electronic equipments of the above organic electronic device, comprises but not limited to display equipment, lighting equipment, light source, and sensor and the like.

The present disclosure will be described below with reference to the specific embodiments, but the present disclosure is not limited to the following embodiments. It should be understood that the appended claims summarized the scope of the present disclosure. Those skilled in the art should realize that certain changes to the embodiments of the present disclosure that are made under the guidance of the concept of the present disclosure will be covered by the spirit and scope of the claims of the present disclosure.

It should be noted that a reagent or instrument of the present disclosure that does not indicate the specific source is a conventional reagent or instrument purchased from the market.

Synthesis Example 1: Synthesis of Compound 1

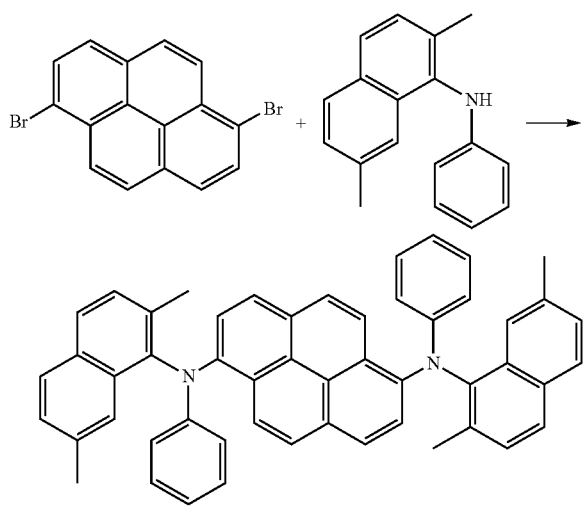

1,6-dibromopyrene (7.2 g, 20 mmol), 2,7-dimethyl-N-phenylnaphthalen-1-amine (9.9 g, 40 mmol), Pd(dba)₂ (690 mg, 1.2 mmol), NaOtBu (11.5 g, 120 mmol), (tBu)₃P (730 mg, 3.6 mmol) and 200 mL anhydrous toluene were added into a 500 mL three-necked flask with condenser under nitrogen flow, stirred at 100° C. overnight. After the reaction, the precipitated solid was filtered, washed with toluene and methanol to get pale yellow solid powder (11 g, 80%).

Synthesis Example 2: Synthesis of Compound 2

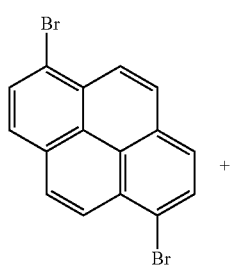

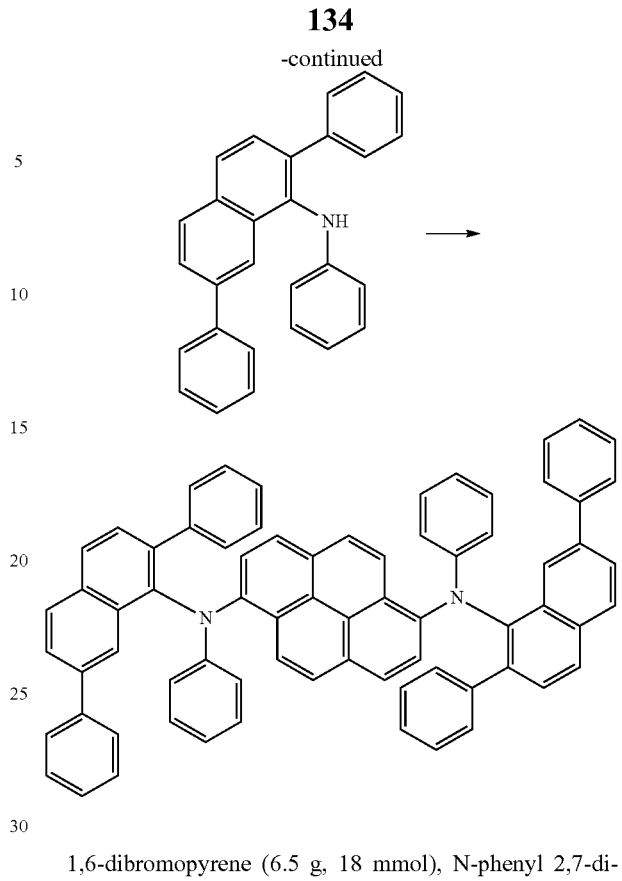

1,6-dibromopyrene (6.5 g, 18 mmol), N-phenyl 2,7-diphenylnaphthalene-1-amine (13.4 g, 36 mmol.), Pd(dba)₂ (620 mg, 1.08 mmol), NaOtBu (10.4 g, 108 mmol), (tBu)₃P (650 mg, 3.24 mmol) and 200 mL anhydrous toluene were added into a 500 mL three-necked flask with condenser under nitrogen flow, stirred at 100° C. overnight. After the reaction, the precipitated solid was filtered, washed with toluene and methanol to get pale yellow solid powder (12.7 g, 75%).

Synthesis Example 3: Synthesis of Compound 3

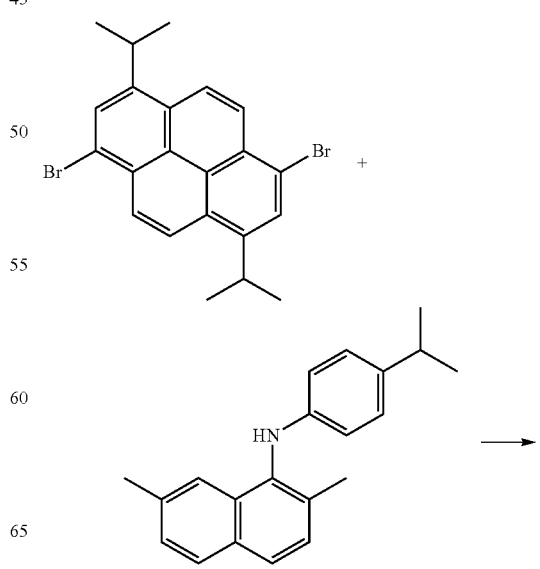

-continued

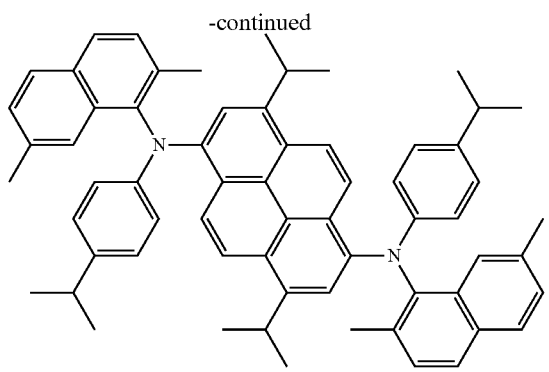

1,6-diisopropyl-3,8-dibromopyrene (6.7 g, 15 mmol), N-(4-isopropylphenyl)-2,7-dimethylnaphthalen-1-amine (8.7 g, 30 mmol), Pd(dba)$_2$ (520 mg, 0.9 mmol), NaOtBu (8.6 g, 90 mmol), (tBu)$_3$P (550 mg, 2.7 mmol) and 150 mL anhydrous toluene were added into a 500 mL three-necked flask with condenser under nitrogen flow, stirred at 100° C. overnight. After the reaction, the precipitated solid was filtered, washed with toluene and methanol to get pale yellow solid powder (10.7 g, 83%).

Synthesis Example 4: Synthesis of Compound 4

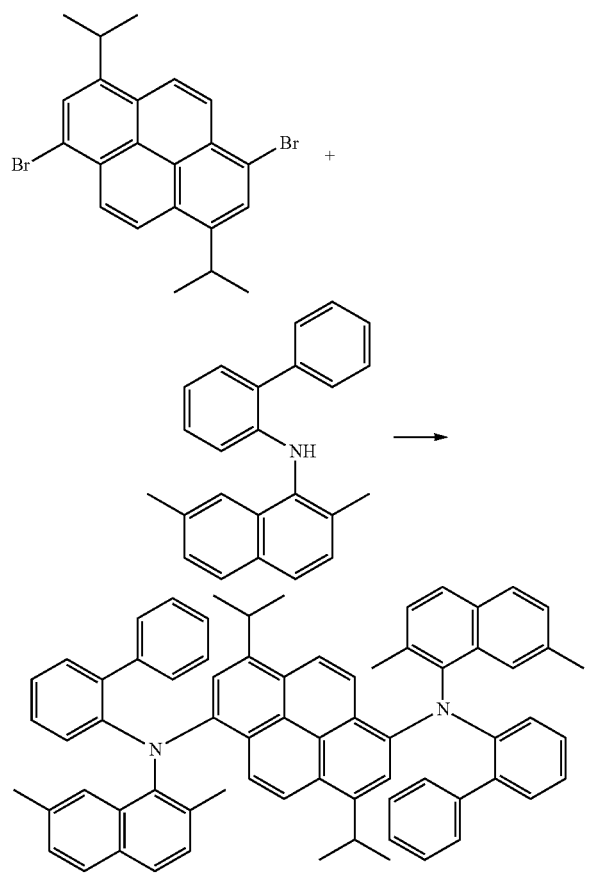

1,6-diisopropyl-3,8-dibromopyrene (8.0 g, 18 mmol), N-([1,1'-biphenyl]-2-yl)-2,7-dimethylnaphthalen-1-amine g, 36 mmol), Pd(dba)$_2$ (620 mg, 1.08 mmol), NaOtBu (10.4 g, 108 mmol), (tBu)$_3$P (650 mg, 3.24 mmol) and 200 mL anhydrous toluene were added into a 500 mL three-necked flask with condenser under nitrogen flow, stirred at 100° C. overnight. After the reaction, the precipitated solid was filtered, washed with toluene and methanol to get pale yellow solid powder (12.7 g, 77%).

Synthesis Example 5: Synthesis of Compound 5

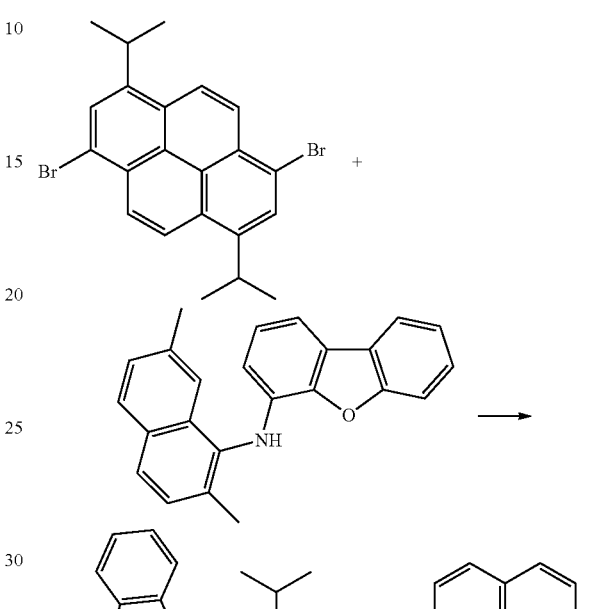

1,6-diisopropyl-3,8-dibromopyrene (4.5 g, 10 mmol), N-(2,7-dimethylnaphthalen-1-yl)-dibenzofuran-4-amine (6.7 g, 20 mmol), Pd(dba)$_2$ (345 mg, 0.6 mmol), NaOtBu (5.76 g, 60 mmol), (tBu)$_3$P (360 mg, 1.8 mmol) and 100 mL anhydrous toluene were added into a 500 mL three-necked flask with condenser under nitrogen flow, stirred at 100° C. overnight. After the reaction, the precipitated solid was filtered, washed with toluene and methanol to get pale yellow solid powder (8.3 g, 87%).

Synthesis Example 6: Synthesis of Compound 6

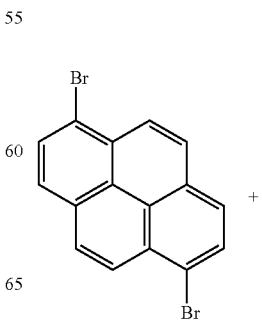

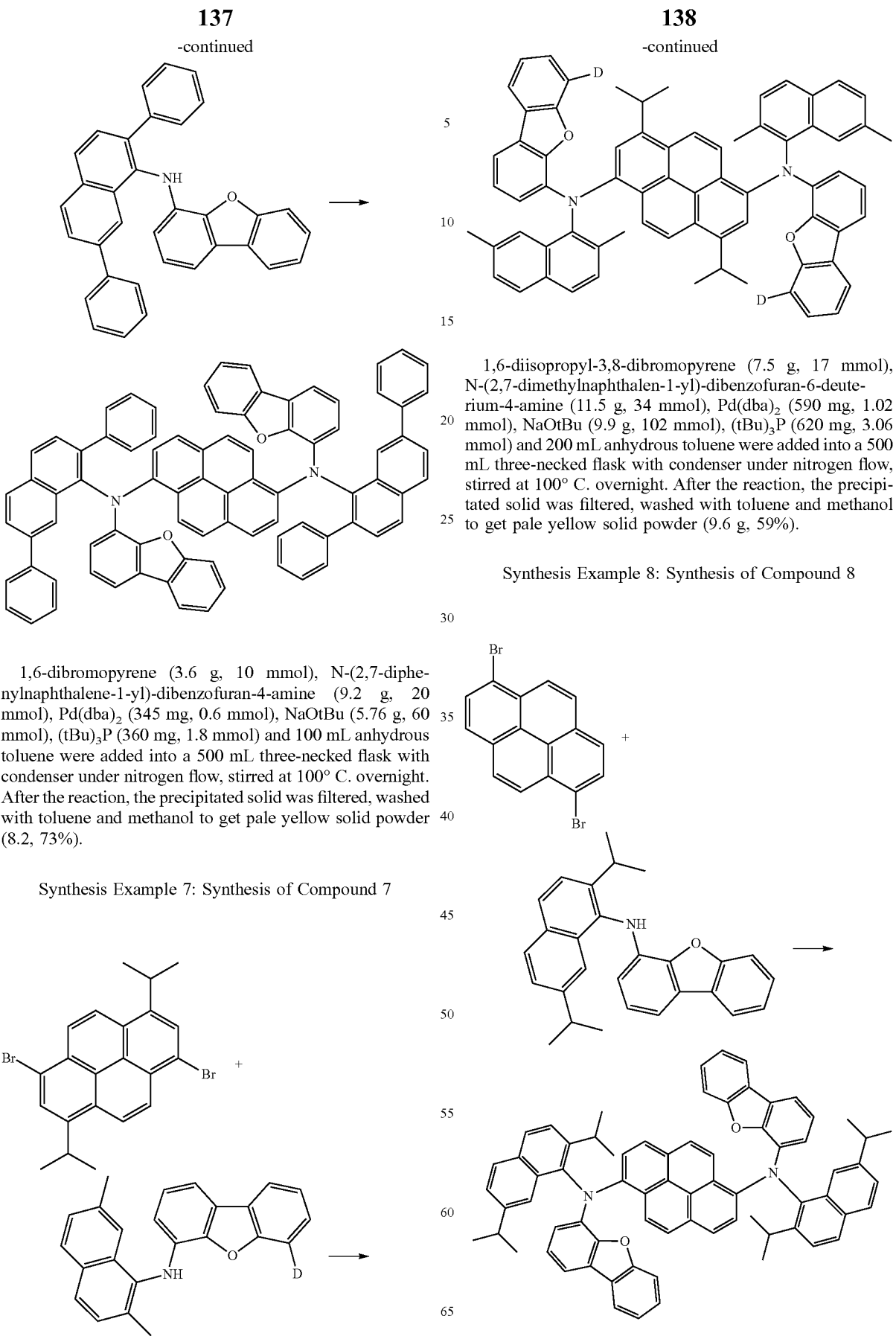

1,6-dibromopyrene (3.6 g, 10 mmol), N-(2,7-diphenylnaphthalene-1-yl)-dibenzofuran-4-amine (9.2 g, 20 mmol), Pd(dba)₂ (345 mg, 0.6 mmol), NaOtBu (5.76 g, 60 mmol), (tBu)₃P (360 mg, 1.8 mmol) and 100 mL anhydrous toluene were added into a 500 mL three-necked flask with condenser under nitrogen flow, stirred at 100° C. overnight. After the reaction, the precipitated solid was filtered, washed with toluene and methanol to get pale yellow solid powder (8.2, 73%).

Synthesis Example 7: Synthesis of Compound 7

1,6-diisopropyl-3,8-dibromopyrene (7.5 g, 17 mmol), N-(2,7-dimethylnaphthalen-1-yl)-dibenzofuran-6-deuterium-4-amine (11.5 g, 34 mmol), Pd(dba)₂ (590 mg, 1.02 mmol), NaOtBu (9.9 g, 102 mmol), (tBu)₃P (620 mg, 3.06 mmol) and 200 mL anhydrous toluene were added into a 500 mL three-necked flask with condenser under nitrogen flow, stirred at 100° C. overnight. After the reaction, the precipitated solid was filtered, washed with toluene and methanol to get pale yellow solid powder (9.6 g, 59%).

Synthesis Example 8: Synthesis of Compound 8

1,6-dibromopyrene (5.7 g, 16 mmol), N-(2,7-diisopropylnaphthalene-1-yl)-dibenzofuran-4-amine (12.6 g, 32 mmol), Pd(dba)₂ (550 mg, 0.96 mmol), NaOtBu (5.76 g, 96 mmol), (tBu)₃P (580 mg, 2.9 mmol) and 200 mL anhydrous toluene were added into a 500 mL three-necked flask with condenser under nitrogen flow, stirred at 100° C. overnight. After the reaction, the precipitated solid was filtered, washed with toluene and methanol to get pale yellow solid powder (11.7 g, 74%).

Synthesis Example 9: Synthesis of Compound 9

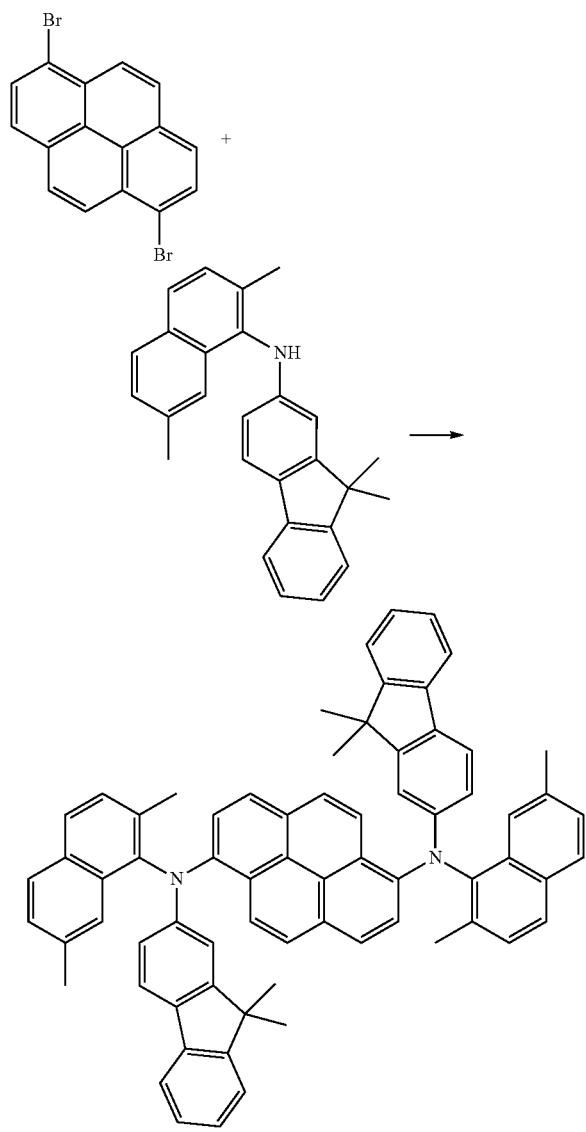

1,6-dibromopyrene (5.4 g, 15 mmol), N-(2,7-dimethylnaphthalen-1-yl)-9,9-dimethyl-fluoren-2-amine (11 g, 30 mmol), Pd(dba)₂ (520 mg, 0.9 mmol), NaOtBu (8.6 g, 90 mmol), (tBu)₃P (540 mg, 2.7 mmol) and 150 mL anhydrous toluene were added into a 500 mL three-necked flask with condenser under nitrogen flow, stirred at 100° C. overnight. After the reaction, the precipitated solid was filtered, washed with toluene and methanol to get pale yellow solid powder (8.9 g, 64%).

Synthesis Example 10: Synthesis of Compound 10

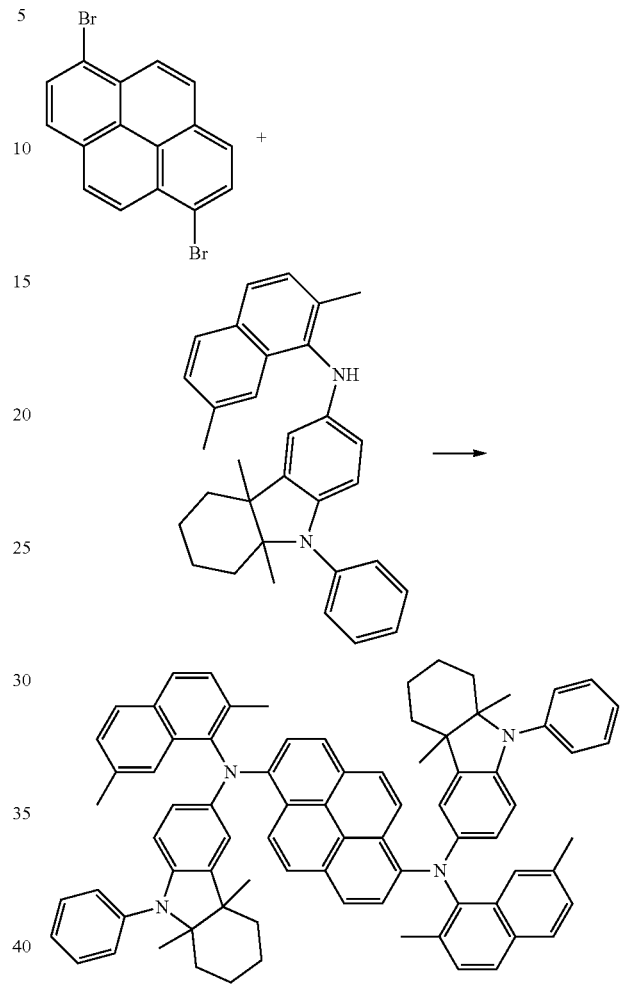

1,6-dibromopyrene (5.04 g, 14 mmol), N-(2,7-dimethylnaphthalen-1-yl)-4a,9a-dimethyl-9-phenyl-1,2,3,4,4a,9a-hexahydro-carbazol-6-amine (12.5 g, 28 mmol), Pd(dba)₂ (480 mg, 0.84 mmol), NaOtBu (8.06 g, 84 mmol), (tBu)₃P (505 mg, 2.5 mmol) and 150 mL anhydrous toluene were added into a 500 mL three-necked flask with condenser under nitrogen flow, stirred at 100° C. overnight. After the reaction, the precipitated solid was filtered, washed with toluene and methanol to get pale yellow solid powder (10.1 g, 66%).

Comparative Example 1: Synthesis of Comparative Compound 1

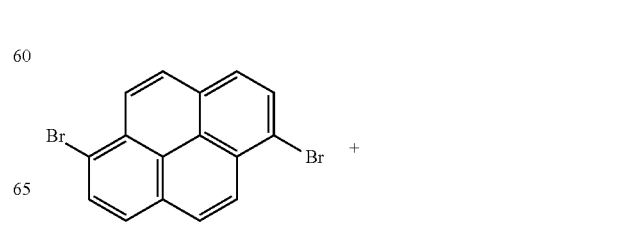

-continued

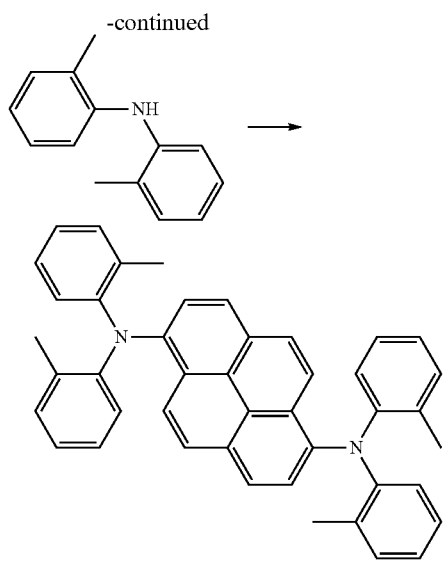

1,6-dibromopyrene (7.2 g, 20 mmol), di-o-tolylamine (7.9 g, 40 mmol), Pd(dba)$_2$ (690 mg, 1.2 mmol), NaOtBu (11.5 g, 120 mmol), (tBu)$_3$P (730 mg, 3.6 mmol) and 150 mL anhydrous toluene was added into a 500 mL three-necked flask with condenser under nitrogen flow, stirred at 100° C. overnight. After the reaction, the precipitated solid was filtered, washed with toluene and methanol to get pale yellow solid powder (10.7 g, 90%).

Example 11: Preparation and Characterization of OLED Device

Materials used for each layer of OLED devices:
HIL: a triarylamine derivative;
HTL: a triarylamine derivative;
Host: an anthracene derivative:
Dopant: compound 1-compound 10, comparative compound 1.

The preparation steps of an OLED device having ITU/HIL, (50 nm) HTL (35 nm)/Host: 5% Dopant (25 nm)/ETL (28 nm)/LiQ (1 nm)/Al (150 nm)/cathode are as follows:

a. Cleaning of conductive glass substrate: when the conductive glass substrate is used for the first time, various solvents such as chloroform, ketone, and isopropanol can be used for cleaning, then treating with UV and ozone plasma;

b. HIL (50 nm), HTL (35 nm), EML (25 nm), ETL (28 nm): formed by thermal evaporation in high vacuum (1×10$^{-6}$ mbar).

c. cathode: LiQ/Al (1 nm/150 nm) was formed by thermal evaporation in high vacuum (1×10$^{-6}$ mbar);

d. encapsulation: The device was encapsulated with ultraviolet curable resin in a nitrogen glove box

| EXAMPLE | Dopant | Luminous efficiency (cd/A) | Lifetime T95 (h) | Chromaticity coordinate |
|---|---|---|---|---|
| Synthesis Example 1: | Compound 1 | 6.9 | 1440 | 0.149, 0.090 |
| Synthesis Example 2: | Compound 2 | 7.3 | 1430 | 0.149, 0.089 |
| Synthesis Example 3: | Compound 3 | 6.9 | 1460 | 0.149, 0.089 |
| Synthesis Example 4: | Compound 4 | 7.3 | 1470 | 0.147, 0.089 |
| Synthesis Example 5: | Compound 5 | 7.7 | 1530 | 0.149, 0.084 |
| Synthesis Example 6: | Compound 6 | 7.1 | 1510 | 0.148, 0.085 |
| Synthesis Example 7: | Compound 7 | 6.9 | 1480 | 0.149, 0.088 |
| Synthesis Example 8: | Compound 8 | 7.4 | 1500 | 0.149, 0.091 |
| Synthesis Example 9: | Compound 9 | 7.1 | 1510 | 0.150, 0.086 |
| Synthesis Example 10: | Compound 10 | 7.3 | 1520 | 0.149, 0.088 |
| Comparative Example 1: | Comparative Compound 1 | 5.3 | 540 | 0.157, 0.152 |

The current-voltage (J-V) characteristic of each OLED device is characterized by, characterization equipment while recording important parameters such as efficiency, lifetime, and external quantum efficiency. It has been found that the chromaticity coordinate of the blue-emitting device prepared by using the compound 1 to compound 10 as the EML, layer emitter is much better than that of comparative compound 1. For example, the chromaticity coordinate of the device prepared by compound 5 is (0.149,0.084); In addition, the luminous efficiency of the blue-emitting device prepared by using the compound 1 to compound 10 as the EMI, layer emitter is in the range of 6-8 cd/A, showing much higher luminous efficiency than the reference. In terms of device lifetime, the lifetime of the blue-emitting device prepared by using the compound 1 to compound 10 as the EML layer emitter is much better than that of the comparative compound 1, for example, the device prepared by compound 5 has a T95 of 1530 hours at 1000 nits.

The technical features of the above-described embodiments may be combined arbitrarily. To simplify the description, all the possible combinations of the technical features in the above embodiments are not described. However, all of the combinations of these technical features should be considered as within the scope of the present disclosure, as long as such combinations do not contradict with each other.

The above-described embodiments merely represent several embodiments of the present disclosure, and the description thereof is more specific and detailed, but it should not be construed as limiting the scope of the present disclosure. It should be noted that, for those skilled in the art, several variations and improvements may be made without departing from the concept of the present disclosure, and these are all within the protection scope of the present disclosure. Therefore, the scope of protection of the present disclosure shall be subject to the appended claims.

The inventioon claimed is:
1. An aromatic amine derivative selected from the group consisting of the structures shown below:
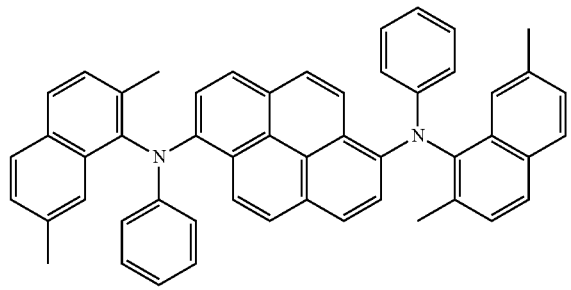
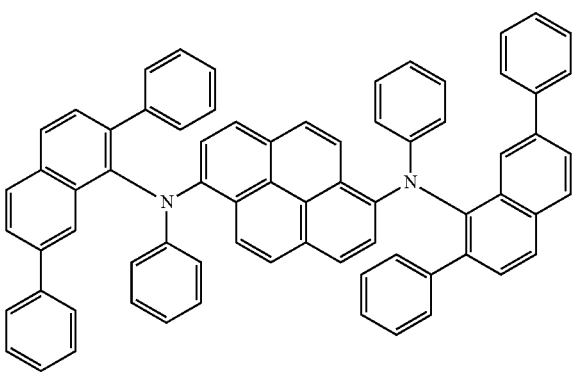
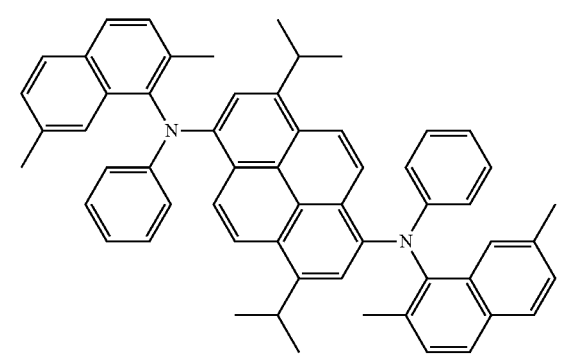
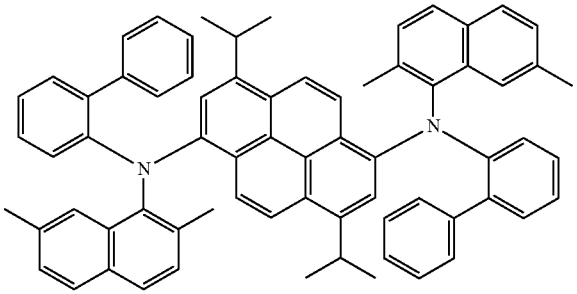
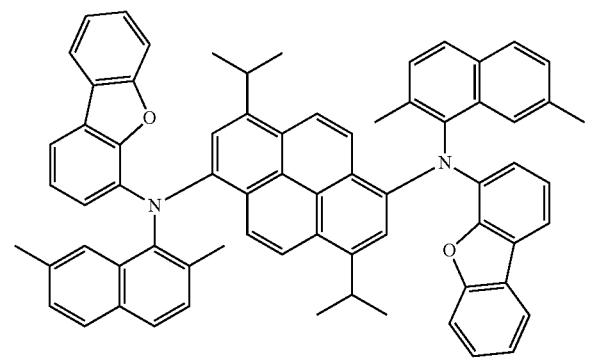
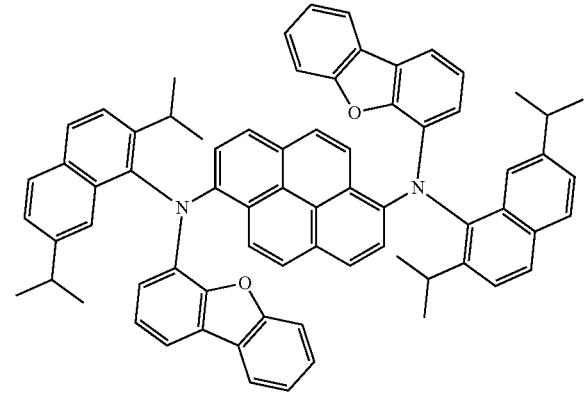

-continued

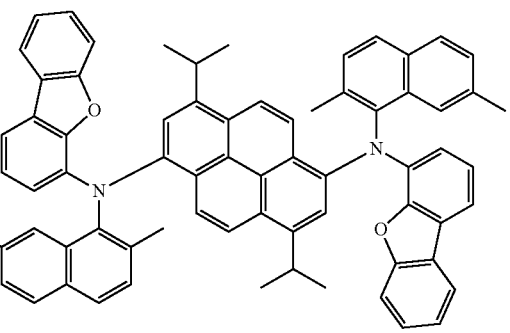

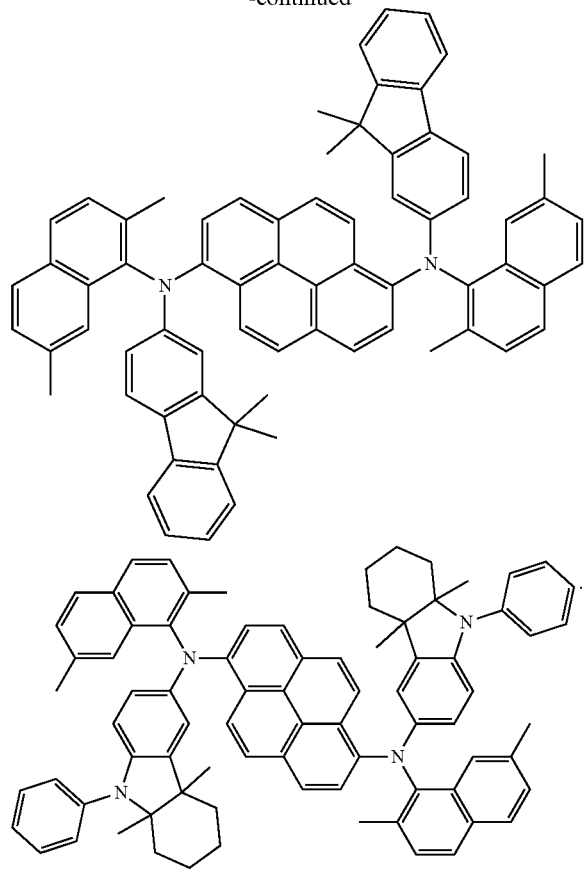

2. The aromatic amine derivative according to claim 1, wherein the aromatic amine derivative has the structure shown below:

3. A mixture comprising:
   the aromatic amine derivative of claim 1; and an organic solvent or
   at least one organic functional material selected from the group consisting of: a hole injection or transport material, a hole blocking material, an electron injection or transport material, an electron blocking material, an organic matrix material, a singlet emitter, a triplet emitter, a thermally activated delayed fluorescent material, and an organic dye.

4. An organic electronic device comprising the aromatic amine derivative of claim 1.

5. An organic electronic device according to claim 4, wherein the organic electronic device is an organic electroluminescent device comprising:
   a cathode,
   an anode, and
   an organic layer,
   wherein the organic layer comprises the aromatic amine derivative.

\* \* \* \* \*